US009566234B2

(12) United States Patent
Perkins et al.

(10) Patent No.: US 9,566,234 B2
(45) Date of Patent: Feb. 14, 2017

(54) SYSTEMS FOR TREATING PULMONARY INFECTIONS

(71) Applicant: Insmed Incorporated, Bridgewater, NJ (US)

(72) Inventors: Walter Perkins, Pennington, NJ (US); Vladimir Malinin, Plainsboro, NJ (US); Xingong Li, Robbinsville, NJ (US); Brian Miller, Hamilton, NJ (US); Dominique Seidel, München (DE); Philipp Holzmann, München (DE); Harald Schulz, Tuttlingen (DE); Michael Hahn, Krailing (DE)

(73) Assignee: Insmed Incorporated, Bridgewater, NJ (US)

( * ) Notice: Subject to any disclaimer, the term of this patent is extended or adjusted under 35 U.S.C. 154(b) by 242 days.

(21) Appl. No.: 13/899,457

(22) Filed: May 21, 2013

(65) Prior Publication Data

US 2013/0330400 A1 Dec. 12, 2013

Related U.S. Application Data

(60) Provisional application No. 61/649,830, filed on May 21, 2012.

(51) Int. Cl.

| | |
|---|---|
| *A61K 9/127* | (2006.01) |
| *A61K 31/7036* | (2006.01) |
| *A61K 9/00* | (2006.01) |
| *A61M 11/00* | (2006.01) |
| *A61M 11/02* | (2006.01) |

(52) U.S. Cl.

CPC ............. *A61K 9/0078* (2013.01); *A61K 9/127* (2013.01); *A61K 9/1271* (2013.01); *A61K 31/7036* (2013.01); *A61M 11/005* (2013.01); *A61M 11/02* (2013.01)

(58) Field of Classification Search
None
See application file for complete search history.

(56) References Cited

U.S. PATENT DOCUMENTS

| | | | |
|---|---|---|---|
| 3,091,572 | A | 5/1963 | Luedemann et al. |
| 3,136,704 | A | 6/1964 | Charney |
| 4,235,871 | A | 11/1980 | Papahadjopoulos et al. |
| 4,372,949 | A | 2/1983 | Kodama et al. |
| 4,394,448 | A | 7/1983 | Szoka, Jr. et al. |
| 4,396,630 | A | 8/1983 | Riedl et al. |
| 4,451,447 | A | 5/1984 | Kaplan et al. |
| 4,515,736 | A | 5/1985 | Deamer |
| 4,522,803 | A | 6/1985 | Lenk et al. |
| 4,547,490 | A | 10/1985 | Ecanow et al. |
| 4,588,578 | A | 5/1986 | Fountain et al. |
| 4,606,939 | A | 8/1986 | Frank et al. |
| 4,684,625 | A | 8/1987 | Eppstein et al. |
| 4,693,999 | A | 9/1987 | Axelsson et al. |
| 4,721,612 | A | 1/1988 | Janoff et al. |
| 4,767,874 | A | 8/1988 | Shima et al. |
| 4,833,134 | A | 5/1989 | Kishimoto et al. |
| 4,857,311 | A | 8/1989 | Domb et al. |
| 4,895,452 | A | 1/1990 | Yiournas et al. |
| 4,895,719 | A | 1/1990 | Radhakrishnan et al. |
| 4,897,384 | A | 1/1990 | Janoff et al. |
| 4,933,121 | A | 6/1990 | Law et al. |
| 4,952,405 | A | 8/1990 | Yau-Young |
| 4,963,367 | A | 10/1990 | Ecanow |
| 4,975,282 | A | 12/1990 | Cullis et al. |
| 4,981,692 | A | 1/1991 | Popescu et al. |
| 5,000,958 | A | 3/1991 | Fountain et al. |
| 5,006,343 | A | 4/1991 | Benson et al. |
| 5,008,050 | A | 4/1991 | Cullis et al. |
| 5,023,087 | A | 6/1991 | Yau-Young |
| 5,030,453 | A | 7/1991 | Lenk et al. |
| 5,041,278 | A | 8/1991 | Janoff et al. |
| 5,049,388 | A | 9/1991 | Knight et al. |
| 5,049,389 | A | 9/1991 | Radhakrishnan |
| 5,059,421 | A | 10/1991 | Loughrey et al. |

(Continued)

FOREIGN PATENT DOCUMENTS

| | | |
|---|---|---|
| CA | 2614764 | 1/2007 |
| CA | 2838111 | 6/2007 |

(Continued)

OTHER PUBLICATIONS

Perkins, W, Aerosolization of liposomal amikacin using different nebulizers, Poster and Oral Presentation at North American Cystic Fibrosis Conference, Oct. 31, 2007.*
Office Action for U.S. Appl. No. 12/598,830, mailed Mar. 7, 2012.
Office Action for U.S. Appl. No. 12/598,830, mailed Oct. 23, 2012.
International Search Report and Written Opinion for International Application No. PCT/US2008/062469, mailed Sep. 18, 2008.
International Preliminary Report on Patentability for International Application No. PCT/US2008/062469, dated Nov. 10, 2009.
Office Action for U.S. Appl. No. 12/250,412, mailed Dec. 2, 2011.
Office Action for U.S. Appl. No. 12/250,412, mailed Jun. 27, 2011.
International Search Report and Written Opinion for International Application No. PCT/US2008/062868, mailed Sep. 18, 2008.

(Continued)

*Primary Examiner* — Brian Gulledge
*Assistant Examiner* — Celeste A Roney
(74) *Attorney, Agent, or Firm* — Cooley LLP

(57) ABSTRACT

Provided herein are systems for treating a subject with a pulmonary infection, for example, a nontuberculous mycobacterial pulmonary infection, a *Burkholderia* pulmonary infection, a pulmonary infection associated with bronchiectasis, or a *Pseudomonas* pulmonary infection. The system includes a pharmaceutical formulation comprising a liposomal aminoglycoside dispersion, and the lipid component of the liposomes consist essentially of electrically neutral lipids. The system also includes a nebulizer which generates an aerosol of the pharmaceutical formulation at a rate greater than about 0.53 gram per minute. The aerosol is delivered to the subject via inhalation for the treatment of the pulmonary infection.

25 Claims, 14 Drawing Sheets

(56) References Cited

U.S. PATENT DOCUMENTS

| | | |
|---|---|---|
| 5,059,591 A | 10/1991 | Janoff et al. |
| 5,077,056 A | 12/1991 | Bally et al. |
| 5,169,637 A | 12/1992 | Lenk et al. |
| 5,178,876 A | 1/1993 | Khokhar et al. |
| 5,192,549 A | 3/1993 | Barenolz et al. |
| 5,211,955 A | 5/1993 | Legros et al. |
| 5,252,339 A | 10/1993 | Cristofori et al. |
| 5,264,618 A | 11/1993 | Felgner et al. |
| 5,269,979 A | 12/1993 | Fountain |
| 5,279,833 A | 1/1994 | Rose |
| 5,316,771 A | 5/1994 | Barenholz et al. |
| 5,320,906 A | 6/1994 | Eley et al. |
| 5,334,761 A | 8/1994 | Gebeyehu et al. |
| 5,409,704 A | 4/1995 | Bally et al. |
| 5,459,127 A | 10/1995 | Felgner et al. |
| 5,508,269 A | 4/1996 | Smith et al. |
| 5,540,936 A | 7/1996 | Coe et al. |
| 5,543,152 A | 8/1996 | Webb et al. |
| 5,549,102 A | 8/1996 | Lintl et al. |
| 5,569,464 A | 10/1996 | Endo et al. |
| 5,578,320 A | 11/1996 | Janoff et al. |
| 5,596,982 A | 1/1997 | Blaha-Schnabel |
| 5,610,198 A | 3/1997 | Barry, III et al. |
| 5,614,216 A | 3/1997 | Janoff |
| 5,616,334 A | 4/1997 | Janoff et al. |
| 5,631,018 A | 5/1997 | Zalipsky et al. |
| 5,641,662 A | 6/1997 | Debs et al. |
| 5,643,599 A | 7/1997 | Lee et al. |
| 5,662,929 A | 9/1997 | Lagace et al. |
| 5,665,383 A | 9/1997 | Grinstaff et al. |
| 5,723,147 A | 3/1998 | Kim et al. |
| 5,736,155 A | 4/1998 | Bally et al. |
| 5,740,966 A | 4/1998 | Blaha-Schnabel |
| 5,741,516 A | 4/1998 | Webb et al. |
| 5,753,613 A | 5/1998 | Ansell et al. |
| 5,756,120 A | 5/1998 | Hersch et al. |
| 5,756,121 A | 5/1998 | Bracken |
| 5,756,353 A | 5/1998 | Debs |
| 5,759,571 A | 6/1998 | Hersch et al. |
| 5,766,627 A | 6/1998 | Sankaram et al. |
| 5,785,987 A | 7/1998 | Hope et al. |
| 5,795,589 A | 8/1998 | Mayer et al. |
| 5,814,335 A | 9/1998 | Webb et al. |
| 5,820,848 A | 10/1998 | Boni et al. |
| 5,837,279 A | 11/1998 | Janoff et al. |
| 5,837,282 A | 11/1998 | Fenske et al. |
| 5,840,702 A | 11/1998 | Bedwell |
| 5,843,473 A | 12/1998 | Woodle et al. |
| 5,849,490 A | 12/1998 | Schonwetter et al. |
| 5,861,159 A | 1/1999 | Pardoll et al. |
| 5,871,710 A | 2/1999 | Bogdanov et al. |
| 5,875,776 A | 3/1999 | Vaghefi |
| 5,922,350 A | 7/1999 | Janoff et al. |
| 5,945,122 A | 8/1999 | Abra et al. |
| 5,957,389 A | 9/1999 | Wunderlich et al. |
| 5,958,449 A | 9/1999 | Hersch et al. |
| 5,972,379 A | 10/1999 | Guo et al. |
| 5,993,850 A | 11/1999 | Sankaram et al. |
| 6,000,394 A | 12/1999 | Blaha-Schnabel et al. |
| 6,045,828 A | 4/2000 | Bystrom et al. |
| 6,051,251 A | 4/2000 | Zalipsky et al. |
| 6,051,549 A | 4/2000 | Roberts et al. |
| 6,085,741 A | 7/2000 | Becker |
| 6,086,851 A | 7/2000 | Boni et al. |
| 6,090,407 A | 7/2000 | Knight et al. |
| 6,106,479 A | 8/2000 | Wunderlich et al. |
| 6,106,858 A | 8/2000 | Ye et al. |
| 6,124,273 A | 9/2000 | Drohan et al. |
| 6,147,060 A | 11/2000 | Zasloff et al. |
| 6,162,462 A | 12/2000 | Bolotin et al. |
| 6,176,237 B1 | 1/2001 | Wunderlich et al. |
| 6,211,162 B1 | 4/2001 | Dale et al. |
| 6,221,388 B1 | 4/2001 | Hersch et al. |
| 6,228,346 B1 | 5/2001 | Zhang et al. |
| 6,228,393 B1 | 5/2001 | DiCosmo et al. |
| 6,235,177 B1 | 5/2001 | Borland et al. |
| 6,274,175 B1 | 8/2001 | Gombotz et al. |
| 6,338,859 B1 | 1/2002 | Leroux et al. |
| 6,348,069 B1 | 2/2002 | Vacanti et al. |
| 6,352,996 B1 | 3/2002 | Cao et al. |
| 6,387,886 B1 | 5/2002 | Montgomery et al. |
| 6,419,901 B2 | 7/2002 | Placke et al. |
| 6,440,393 B1 | 8/2002 | Waldrep et al. |
| 6,443,898 B1 | 9/2002 | Unger et al. |
| 6,447,753 B2 | 9/2002 | Edwards et al. |
| 6,451,784 B1 | 9/2002 | Placke et al. |
| 6,458,373 B1 | 10/2002 | Lambert et al. |
| 6,468,532 B1 | 10/2002 | Hsei et al. |
| 6,475,779 B2 | 11/2002 | Mathiowitz et al. |
| 6,481,438 B1 | 11/2002 | Gallem et al. |
| 6,492,560 B2 | 12/2002 | Wilbur et al. |
| 6,497,901 B1 | 12/2002 | Royer |
| 6,509,323 B1 | 1/2003 | Davis et al. |
| 6,511,676 B1 | 1/2003 | Boulikas |
| 6,513,727 B1 | 2/2003 | Jaser et al. |
| 6,521,211 B1 | 2/2003 | Unger et al. |
| 6,521,736 B2 | 2/2003 | Watterson et al. |
| 6,546,927 B2 | 4/2003 | Litherland et al. |
| 6,554,201 B2 | 4/2003 | Klimowicz et al. |
| 6,596,305 B1 | 7/2003 | Edgerly-Plug |
| 6,599,912 B1 | 7/2003 | Au et al. |
| 6,606,990 B2 | 8/2003 | Stapleton et al. |
| 6,613,352 B2 | 9/2003 | Lagace et al. |
| 6,615,824 B2 | 9/2003 | Power |
| 6,629,646 B1 | 10/2003 | Ivri |
| 6,676,034 B2 | 1/2004 | Tanaka et al. |
| 6,679,251 B1 | 1/2004 | Gallem et al. |
| 6,843,942 B2 | 1/2005 | Katinger et al. |
| 6,845,770 B2 | 1/2005 | Klimowicz et al. |
| 6,855,296 B1 | 2/2005 | Baker et al. |
| 6,900,184 B2 | 5/2005 | Cohen et al. |
| 6,915,962 B2 | 7/2005 | Power et al. |
| 6,916,490 B1 | 7/2005 | Garver et al. |
| 6,948,491 B2 | 9/2005 | Loeffler et al. |
| 6,962,151 B1 | 11/2005 | Knoch et al. |
| 6,983,747 B2 | 1/2006 | Gallem et al. |
| 6,991,809 B2 | 1/2006 | Anderson |
| 7,059,320 B2 | 6/2006 | Feiner et al. |
| 7,063,860 B2 | 6/2006 | Chancellor et al. |
| 7,077,126 B2 | 7/2006 | Kummer et al. |
| 7,100,600 B2 | 9/2006 | Loeffler et al. |
| 7,104,463 B2 | 9/2006 | Litherland et al. |
| 7,131,440 B2 | 11/2006 | Sonntag |
| 7,252,085 B2 | 8/2007 | Kunschir |
| 7,255,106 B2 | 8/2007 | Gallem et al. |
| 7,331,339 B2 | 2/2008 | Smith et al. |
| 7,368,102 B2 | 5/2008 | Tarara et al. |
| D583,928 S | 12/2008 | Knoch |
| 7,458,372 B2 | 12/2008 | Feiner et al. |
| 7,472,701 B2 | 1/2009 | Pfichner et al. |
| 7,544,369 B2 | 6/2009 | Boni et al. |
| 7,600,511 B2 | 10/2009 | Power et al. |
| 7,686,014 B2 | 3/2010 | Boehm et al. |
| 7,718,189 B2 | 5/2010 | Boni et al. |
| 7,748,377 B2 | 7/2010 | Smith et al. |
| 7,758,886 B2 | 7/2010 | Jauernig et al. |
| 7,771,642 B2 | 8/2010 | Power et al. |
| 7,779,838 B2 | 8/2010 | Hetzer et al. |
| 7,879,351 B2 | 2/2011 | Li et al. |
| 7,891,352 B2 | 2/2011 | Gallem et al. |
| 7,931,212 B2 | 4/2011 | Urich et al. |
| D638,117 S | 5/2011 | Eckstein et al. |
| 7,958,887 B2 | 6/2011 | Kelliher et al. |
| 7,971,588 B2 | 7/2011 | Fink et al. |
| 7,980,247 B2 | 7/2011 | Boehm et al. |
| 8,006,698 B2 | 8/2011 | Boehm et al. |
| D652,908 S | 1/2012 | Eckstein et al. |
| 8,100,162 B2 | 1/2012 | Joern et al. |
| 8,113,194 B2 | 2/2012 | Boehm et al. |
| D656,604 S | 3/2012 | Eckstein et al. |
| 8,226,975 B2 | 7/2012 | Weers |
| 8,263,645 B2 | 9/2012 | Keller |
| 8,333,187 B2 | 12/2012 | Gallem et al. |
| 8,342,171 B2 | 1/2013 | Boehm et al. |

(56) References Cited

U.S. PATENT DOCUMENTS

| | | |
|---|---|---|
| 8,347,878 B2 | 1/2013 | Schuschnig et al. |
| 8,387,895 B2 | 3/2013 | Stangl |
| 8,398,001 B2 | 3/2013 | Borland et al. |
| D680,214 S | 4/2013 | Eckstein et al. |
| 8,459,252 B2 | 6/2013 | Gallem et al. |
| 8,511,581 B2 | 8/2013 | Urich et al. |
| 8,596,264 B2 | 12/2013 | Sommer |
| 8,616,195 B2 | 12/2013 | Power et al. |
| 8,632,804 B2 | 1/2014 | Weers |
| 8,642,075 B2 | 2/2014 | Weers |
| 8,671,933 B2 | 3/2014 | Boehm et al. |
| 8,673,348 B2 | 3/2014 | Weers |
| 8,673,349 B2 | 3/2014 | Weers |
| 8,679,532 B2 | 3/2014 | Weers |
| 8,720,432 B2 | 5/2014 | Borgschulte et al. |
| 8,720,435 B2 | 5/2014 | Gallem et al. |
| 8,739,777 B2 | 6/2014 | Kreutzmann et al. |
| 8,802,137 B2 | 8/2014 | Boni et al. |
| 8,852,557 B2 | 10/2014 | Keller et al. |
| 8,985,100 B2 | 3/2015 | Minocchieri et al. |
| 9,016,272 B2 | 4/2015 | Gallem et al. |
| 9,027,548 B2 | 5/2015 | Borgschulte et al. |
| 9,046,092 B2 | 6/2015 | Boehm et al. |
| 9,061,303 B2 | 6/2015 | Waldner et al. |
| 9,072,464 B2 | 7/2015 | Haartsen et al. |
| 9,084,862 B2 | 7/2015 | Blakey et al. |
| 9,095,676 B2 | 8/2015 | Gallem et al. |
| 9,108,211 B2 | 8/2015 | Ivri |
| 9,114,081 B2 | 8/2015 | Gupta |
| 9,119,783 B2 | 9/2015 | Gupta |
| 9,119,930 B2 | 9/2015 | Kreutzmann et al. |
| 9,149,588 B2 | 10/2015 | Gordon et al. |
| 9,161,963 B2 | 10/2015 | Keller et al. |
| 9,168,556 B2 | 10/2015 | Pumm et al. |
| 9,198,859 B2 | 12/2015 | Keller et al. |
| 9,265,900 B2 | 2/2016 | Loenner et al. |
| 9,333,214 B2 | 5/2016 | Gupta |
| 9,402,845 B2 | 8/2016 | Weers |
| 2001/0006660 A1 | 7/2001 | Lagace et al. |
| 2002/0035061 A1 | 3/2002 | Krieger et al. |
| 2002/0052390 A1 | 5/2002 | Ponikau |
| 2002/0086852 A1 | 7/2002 | Cantor et al. |
| 2002/0187105 A1 | 12/2002 | Zou et al. |
| 2003/0059375 A1 | 3/2003 | Perez-Soler et al. |
| 2003/0099697 A1 | 5/2003 | Panzner et al. |
| 2003/0118636 A1 | 6/2003 | Friesen et al. |
| 2003/0138481 A1 | 7/2003 | Zadi |
| 2003/0224039 A1 | 12/2003 | Boni et al. |
| 2004/0009126 A1 | 1/2004 | Pilkiewicz et al. |
| 2004/0032037 A1 | 2/2004 | Katinger et al. |
| 2004/0101553 A1 | 5/2004 | Lee et al. |
| 2004/0142025 A1 | 7/2004 | MacLachlan et al. |
| 2004/0142026 A1 | 7/2004 | Boni et al. |
| 2004/0180082 A1 | 9/2004 | Kang et al. |
| 2005/0019926 A1 | 1/2005 | Gonda et al. |
| 2005/0025822 A1 | 2/2005 | Wong et al. |
| 2005/0042341 A1 | 2/2005 | Thomas et al. |
| 2005/0113337 A1 | 5/2005 | Taneja et al. |
| 2005/0214224 A1 | 9/2005 | Weers et al. |
| 2005/0220752 A1 | 10/2005 | Charmot et al. |
| 2005/0249795 A1 | 11/2005 | Zhang et al. |
| 2006/0062738 A1* | 3/2006 | Hofmann et al. ............ 424/45 |
| 2006/0067998 A1 | 3/2006 | Kurzrock et al. |
| 2006/0073198 A1* | 4/2006 | Boni et al. ................. 424/450 |
| 2006/0217603 A1 | 9/2006 | Nagai et al. |
| 2007/0077290 A1 | 4/2007 | Li et al. |
| 2007/0081963 A1 | 4/2007 | Oh et al. |
| 2007/0196461 A1 | 8/2007 | Weers |
| 2007/0267010 A1 | 11/2007 | Fink et al. |
| 2008/0089927 A1 | 4/2008 | Malinin |
| 2008/0131497 A1 | 6/2008 | Perkins et al. |
| 2008/0246472 A1 | 10/2008 | Igney et al. |
| 2009/0104256 A1 | 4/2009 | Gupta |
| 2009/0269396 A1 | 10/2009 | Cipolla et al. |
| 2009/0274754 A1 | 11/2009 | Cipolla et al. |
| 2010/0068257 A1 | 3/2010 | Boni et al. |
| 2010/0196455 A1 | 8/2010 | Malinin |
| 2010/0260829 A1 | 10/2010 | Boni et al. |
| 2011/0064796 A1 | 3/2011 | Cipolla et al. |
| 2011/0159079 A1 | 6/2011 | Li et al. |
| 2012/0010162 A1 | 1/2012 | Norling |
| 2012/0244206 A1 | 9/2012 | Cipolla et al. |
| 2013/0028960 A1 | 1/2013 | Weers |
| 2013/0052260 A1 | 2/2013 | Weers |
| 2013/0064883 A1 | 3/2013 | Weers |
| 2013/0071468 A1 | 3/2013 | Weers |
| 2013/0071469 A1 | 3/2013 | Weers |
| 2013/0089598 A1 | 4/2013 | Gupta |
| 2013/0136788 A1 | 5/2013 | Gupta |
| 2014/0072620 A1 | 3/2014 | Weers |
| 2014/0248335 A1 | 9/2014 | Malinin |
| 2014/0314835 A1 | 10/2014 | Boni et al. |
| 2015/0272880 A1 | 10/2015 | Seidel et al. |
| 2016/0113927 A1 | 4/2016 | Weers |
| 2016/0143849 A1 | 5/2016 | Gupta |
| 2016/0151402 A1 | 6/2016 | Gupta |
| 2016/0184301 A1 | 6/2016 | Weers |
| 2016/0184302 A1 | 6/2016 | Weers |

FOREIGN PATENT DOCUMENTS

| | | |
|---|---|---|
| EP | 0069307 | 1/1983 |
| EP | 0274431 | 5/1994 |
| EP | 2457609 | 5/2012 |
| GB | 2145107 | 3/1985 |
| JP | 63-500175 | 1/1988 |
| JP | 63-239213 | 5/1988 |
| JP | 10-511363 | 11/1998 |
| JP | 2006-028069 | 2/2006 |
| UA | 27298 | 10/2007 |
| UA | 27804 | 11/2007 |
| WO | WO 85/00968 | 3/1985 |
| WO | WO 86/06959 | 12/1986 |
| WO | WO 87/00043 | 1/1987 |
| WO | WO 87/02219 | 4/1987 |
| WO | WO 88/04573 | 6/1988 |
| WO | WO 91/16882 | 11/1991 |
| WO | WO 93/12240 | 6/1993 |
| WO | WO 94/12155 | 6/1994 |
| WO | WO 94/12156 | 6/1994 |
| WO | WO 94/22430 | 10/1994 |
| WO | WO 96/08235 | 3/1996 |
| WO | WO 96/19199 | 6/1996 |
| WO | WO 96/19972 | 7/1996 |
| WO | WO 97/29851 | 8/1997 |
| WO | WO 99/30686 | 6/1999 |
| WO | WO 99/61003 | 12/1999 |
| WO | WO 99/65466 | 12/1999 |
| WO | WO 00/27359 | 5/2000 |
| WO | WO 00/29103 | 5/2000 |
| WO | WO 00/45791 | 8/2000 |
| WO | WO 01/05373 | 1/2001 |
| WO | WO 01/18280 | 3/2001 |
| WO | WO 01/32246 | 5/2001 |
| WO | WO 02/32400 | 4/2002 |
| WO | WO 02/43699 | 6/2002 |
| WO | WO 03/045965 | 6/2003 |
| WO | WO 03/075889 | 9/2003 |
| WO | WO 03/075890 | 9/2003 |
| WO | WO 2004/002453 | 1/2004 |
| WO | WO 2004/047802 | 6/2004 |
| WO | WO 2004/054499 | 7/2004 |
| WO | WO 2004/110346 | 12/2004 |
| WO | WO 2006/108556 | 10/2006 |
| WO | WO 2007/011940 | 1/2007 |
| WO | WO 2007/012191 | 2/2007 |
| WO | WO 2007/067520 | 6/2007 |
| WO | WO 2007/117509 | 10/2007 |
| WO | WO 2007/117550 | 10/2007 |
| WO | WO 2008/039989 | 4/2008 |
| WO | WO 2008/137717 | 11/2008 |
| WO | WO 2008/137917 | 11/2008 |
| WO | WO 2010/045209 | 4/2010 |

(56) References Cited

FOREIGN PATENT DOCUMENTS

| WO | WO 2012/069531 | 5/2012 |
|----|----------------|--------|
| WO | WO 2013/177226 | 11/2013 |
| WO | WO 2015/017807 | 2/2015 |

OTHER PUBLICATIONS

International Preliminary Report on Patentability for International Application No. PCT/US2008/062868, dated Nov. 10, 2009.
Examination Report for Australian Patent Application No. 2009303542, dated Jun. 20, 2012.
Office Action for Chinese Patent Application No. 200980140740.2, dated Jul. 3, 2012.
Office Action for Chinese Patent Application No. 200980140740.2, dated Jun. 4, 2013.
Office Action for New Zealand Patent Application No. 592217, mailed Sep. 1, 2011.
Office Action for New Zealand Patent Application No. 592217, mailed Feb. 5, 2013.
Search Report and Written Opinion for Singapore Application No. 201102419-7, mailed Sep. 7, 2012.
Written Opinion for International Application No. PCT/US2009/060468, mailed Jun. 24, 2010.
International Preliminary Report on Patentability for International Application No. PCT/US2009/060468, dated Apr. 19, 2011.
First Examination Report for New Zealand Patent Application No. 606383, dated Feb. 5, 2013.
Office Action for U.S. Appl. No. 13/480,246, mailed Jan. 10, 2013.
Office Action for Australian Patent Application No. 2003304204, mailed Jun. 25, 2008.
Office Action for Canadian Patent Application No. 2504317, dated Jan. 27, 2011.
Office Action for Canadian Patent Application No. 2504317, dated Jun. 16, 2010.
First Office Action for Chinese Patent Application No. 200380106534.2, dated Aug. 11, 2006.
Second Office Action for Chinese Patent Application No. 200380106534.2 [no date].
Third Office Action for Chinese Patent Application No. 200380106534.2, dated May 22, 2009.
Supplementary European Search Report for European Application No. 03816990.0, mailed Jan. 12, 2009.
Summons to Attend Oral Hearing for European Application No. 03816990.0, mailed Dec. 21, 2011.
Office Action for European Application No. 03816990.0, mailed Jun. 17, 2011.
Office Action for European Application No. 03816990.0, mailed Apr. 24, 2009.
Office Action for European Application No. 03816990.0, mailed Jun. 5, 2012.
Office Action for Israel Patent Application No. 168279, dated Nov. 3, 2010.
Office Action for Israel Patent Application No. 168279, dated Aug. 17, 2009.
Office Action for Israel Patent Application No. 168279, dated Jun. 23, 2008.
Office Action for Israel Application No. 168279, dated Jun. 6, 2012.
Office Action for Indian Patent Application No. 2219/DELNP/2005, dated Jan. 3, 2007.
Decision of Refusal for Japanese Patent Application No. 2005-500829, dated Feb. 14, 2012.
Notification of Reasons for Refusal for Japanese Patent Application No. 2005-500829, dated Feb. 15, 2011.
Notification of Reasons for Refusal for Japanese Patent Application No. 2005-500829, dated Jul. 6, 2010.
Office Action for Korean Patent Application No. 10-2005-7007679, dated Dec. 26, 2011.
Office Action for Korean Patent Application No. 10-2005-7007679, dated Jan. 18, 2011.
Office Action for Korean Patent Application No. 10-2005-7007679, dated Dec. 26, 2012.
Office Action for Mexican Patent Application No. PA/a/2005/004580, mailed Aug. 25, 2009.
Third Office Action for Mexican Patent Application No. PA/a/2005/004580, mailed Dec. 10, 2008.
Second Office Action for Mexican Patent Application No. PA/a/2005/004580, mailed May 9, 2008.
First Office Action for Mexican Patent Application No. PA/a/2005/004580, mailed Jan. 30, 2008.
Office Action for New Zealand Patent Application No. 540087, dated Jan. 4, 2008.
Office Action for New Zealand Patent Application No. 540087, dated Sep. 14, 2006.
Office Action for U.S. Appl. No. 10/696,389, mailed Nov. 14, 2008.
Office Action for U.S. Appl. No. 10/696,389, mailed Mar. 28, 2008.
Office Action for U.S. Appl. No. 10/696,389, mailed Oct. 10, 2007.
Office Action for U.S. Appl. No. 10/696,389, mailed Apr. 2, 2007.
International Search Report for International Application No. PCT/US2003/034240, mailed Jul. 12, 2005.
International Preliminary Report on Patentability for International Application No. PCT/US2003/034240, mailed May 6, 2013.
Office Action for Japanese Patent Application No. 2011-001318, mailed Feb. 12, 2013.
Office Action for Mexican Patent Application No. MX/a/2010/000195, mailed Feb. 1, 2012.
Office Action for Mexican Patent Application No. MX/a/2010/000195, mailed Jul. 27, 2011.
Office Action for Mexican Patent Application No. MX/a/2010/000195, mailed Oct. 2, 2012.
Office Action for New Zealand Patent Application No. 564543, mailed Jan. 4, 2008.
Examiner's First Report for Australian Patent Application No. 2006270008, dated Dec. 10, 2010.
Office Action for Canadian Patent Application No. 2,614,764, dated Nov. 14, 2012.
Second Office Action for Chinese Patent Application No. 200680034397.X, dated Feb. 9, 2011.
First Office Action for Chinese Patent Application No. 200680034397.X, dated Jan. 22, 2010.
Third Office Action for Chinese Patent Application No. 200680034397.X, dated Mar. 12, 2012.
Fourth Office Action for Chinese Patent Application No. 200680034397.X, dated Dec. 4, 2012.
Office Action for Columbian Patent Application No. 08016117, dated Jun. 26, 2012.
Office Action for Columbian Patent Application No. 08016117, dated Jan. 14, 2013.
Office Action for Costa Rican Patent Application No. 9736, dated Apr. 22, 2013.
Office Action for Egyptian Patent Application No. PCT 84/2008, mailed Oct. 24, 2012.
Supplementary European Search Report for European Application No. 06787716.7, mailed Dec. 29, 2011.
Office Action for European Application No. 06787716.7, dated Oct. 26, 2012.
Office Action for Israel Patent Application No. 188406, dated Jun. 13, 2011.
Office Action for Israel Patent Application No. 188406, dated Apr. 26, 2010.
Office Action for Israel Patent Application No. 188406, dated Jan. 6, 2013.
Office Action for Japanese Patent Application No. 2008-522895, dated Apr. 17, 2012.
Office Action for Korean Patent Application No. 10-2008-7002031, dated Dec. 21, 2012.
Office Action for Mexican Patent Application No. MX/a/2008/000425, dated Jun. 2, 2010.
Office Action for New Zealand Patent Application No. 565300, dated Feb. 24, 2011.
Office Action for New Zealand Patent Application No. 565300, dated Nov. 11, 2009.

(56) References Cited

OTHER PUBLICATIONS

Office Action for New Zealand Patent Application No. 565300, dated May 31, 2011.
Office Action for U.S. Appl. No. 11/185,448, mailed Dec. 17, 2009.
Office Action for U.S. Appl. No. 11/185,448, mailed Jun. 30, 2009.
International Search Report and Written Opinion for International Application No. PCT/US2006/027859, mailed Aug. 14, 2007.
International Preliminary Report on Patentability for International Application No. PCT/US2006/027859, dated Jan. 22, 2008.
Office Action for Canadian Patent Application No. 2,646,255, dated Feb. 4, 2013.
Supplementary European Search Report for European Application No. 07754853, mailed Jan. 16, 2013.
Office Action for Japanese Application No. 2009-504281, dated Sep. 4, 2012.
Office Action for Mexican Patent Application No. MX/a/2008/012684, dated Jul. 8, 2011.
Office Action for Mexican Patent Application No. MX/a/2008/012684, dated Apr. 5, 2011.
Office Action for U.S. Appl. No. 11/398,859, mailed Jun. 4, 2010.
Office Action for U.S. Appl. No. 11/398,859, mailed Sep. 11, 2009.
International Search Report and Written Opinion for International Application No. PCT/US2007/008404, mailed Sep. 26, 2008.
International Preliminary Report on Patentability for International Application No. PCT/US2007/008404, dated Oct. 21, 2008.
European Search Report for European Patent Application No. 11159754, mailed Jun. 22, 2011.
Office Action for U.S. Appl. No. 12/424,177, mailed Mar. 16, 2012.
Office Action for U.S. Appl. No. 12/424,177, mailed Aug. 31, 2011.
Office Action for U.S. Appl. No. 12/748,756, mailed Jan. 27, 2012.
Office Action for U.S. Appl. No. 12/748,756, mailed Aug. 23, 2012.
Office Action for Australian Patent Application No. 2006322076, mailed Sep. 23, 2011.
Office Action for Canadian Patent Application No. 2,631,872, dated Dec. 7, 2012.
Supplementary European Search Report for European Application No. 06847502, mailed Dec. 5, 2012.
Office Action for Japanese Patent Application No. 2008-544430, mailed May 26, 2012.
Office Action for U.S. Appl. No. 11/634,343, mailed Jan. 17, 2012.
Office Action for U.S. Appl. No. 11/634,343, mailed Aug. 4, 2011.
Office Action for U.S. Appl. No. 11/634,343, mailed Apr. 5, 2011.
Office Action for U.S. Appl. No. 11/634,343, mailed Sep. 14, 2010.
Office Action for U.S. Appl. No. 11/634,343, mailed Feb. 23, 2010.
Office Action for U.S. Appl. No. 11/634,343, mailed Jun. 19, 2009.
International Search Report and Written Opinion for International Application No. PCT/US2006/046360, mailed Oct. 17, 2007.
International Preliminary Report on Patentability for International Application No. PCT/US2006/046360, dated Jun. 11, 2008.
Office Action for U.S. Appl. No. 13/527,213, mailed Mar. 11, 2013.
Office Action for U.S. Appl. No. 13/664,181, mailed Feb. 12, 2013.
Office Action for U.S. Appl. No. 13/666,420, mailed Mar. 5, 2013.
Office Action for U.S. Appl. No. 13/675,559, mailed Mar. 19, 2013.
Office Action for U.S. Appl. No. 13/675,587, mailed Apr. 4, 2013.
Supplementary European Search Report and Written Opinion for European Application No. 07754936, mailed Jan. 18, 2013.
Office Action for Japanese Application No. 2009-504301, dated Sep. 4, 2012.
Office Action for U.S. Appl. No. 11/696,343, mailed Oct. 21, 2011.
Office Action for U.S. Appl. No. 11/696,343, mailed May 10, 2011.
International Search Report and Written Opinion for International Application No. PCT/US2007/008500, mailed Sep. 26, 2008.
International Preliminary Report on Patentability for International Application No. PCT/US2007/008500, dated Oct. 21, 2008.
Allen, T. M. et al., "Effect of liposome size and drug release properties of pharmacokinetics of encapsulated drug to rats," The Journal of Pharmacology and Experimental Therapeutics, 226(2):539-544 (1983).

Alton et al., "Cationic lipid-mediated CFTR gene transfer to the lungs and nose of patients with cystic fibrosis: a double-blind placebo-controlled trial," The Lancet, 353(9157):947-954 (1999).
Andrews, J. M., "Determination of minimum inhibitory concentrations," Journal of Antimicrobial Chemotherapy, 48(S1):5-14 (2001).
Antos, M. et al., "Antibacterial activity of liposomal amikacin against Pseudomonas aeruginosa in vitro," Pharmacological Research, 32(1/2):84-87 (1995).
Bakker-Woudenberg, I. et al., "Efficacy of gentamicin or ceftazidine entrapped in liposomes with prolonged blood circulation and enhanced localization in Klebsiella pneumoniae-infected lung tissue," The Journal Infectious Diseases, 171:938-947 (1995).
Ball, V. et al., "Complexation mechanism of bovine serum albumin and poly(allylamine hydrochloride)," J. Phys. Chem. B., 106(9):2357-2364 (2002).
Bangham, A. D. et al., "Diffusion of univalent ions across the lamellae of swollen phospholipids," J. Mol. Biol., 13:238-252 (1965).
Bangham, A. D., Introduction, "Liposomes: An Historical Perspective," in: Liposomes, Ostro, M. J. (ed.), pp. 1-25, Marcel Dekker, Inc., New York (1983).
Bargoni, A. et al., "Transmucosal transport of tobramycin incorporated in solid lipid nanoparticles (SLN) after duodenal administration to rats. Part II—Tissue distribution," Pharmacological Research, 43(5):497-502 (2001).
Beaulac, C. et al., "Eradication of Mucoid Pseudomonas aeruginosa with Fluid Liposome-Encapsulated Tobramycin in an Animal Model of Chronic Pulmonary Infection," Antimicrobial Agents and Chemotherapy, 40(3):665-669 (1996).
Beaulac, C. et al., "In-vitro bactericidal efficacy of sub-MIC concentrations of liposome-encapsulated antibiotic against Gram-negative and Gram-positive bacteria," Journal of Antimicrobial Chemotherapy, 41:35-41 (1998).
Beaulac, C. et al., "Aerolization of low phase transition temperature liposomal tobramycin as a dry powder in an animal model of chronic pulmonary infection caused by Pseudomonas aeruginosa," Journal Drug Targeting, 7(1):33-41 (1999).
Beaulac, C. et al., "In vitro kinetics of drug release and pulmonary retention of microencapsulated antibiotic in liposomal formulations in relation to the lipid composition," Journal Microencapsulation 14(3):335-348 (1997).
Bermudez, L. E. et al., "Treatment of disseminated Mycobacterium avium complex infection of beige mice with liposome-encapsulated aminoglycosides," The Journal of Infectious Diseases, 161(16):1262-1268 (1990).
Bucke, W. E. et al., "Surface-modified amikacin-liposomes: organ distribution and interaction with plasma proteins," Journal of Drug Targeting, 5(2):99-108 (1997).
Bunderberg de Jong, H. G. et al., Koazevation (Entmischung in Kolloidalen Systemen), Koll, Zeitsch, 50(10):39-48 (1930).
Carlier, M. B. et al., "Inhibition of lysosomal phospholipases by aminoglycoside antibiotics: in vitro comparative studies," Antimicrobial Agents and Chemotherapy, 23(3):440-449 (1983).
Cantin, A. M. et al., "Aerosolized prolastin suppresses bacterial proliferation in a model of chronic pseudomonas aeruginosa lung infection," Am. J. Respir. Crit. Care Med., 160:1130-1135 (1999).
Cash, H. A. et al., "A rat model of chronic respiratory infection with Pseudomonas aeruginosa," American Review of Respiratory Disease, 119(3):453-459 (1979).
Challoner, P. B. et al., "Gamma Scintigraphy Lung Deposition Comparison of TOBI in the PARI LC PLUS Nebulizer and the Aerodose Inhaler," American Thoracic Society 97th International Conference, San Francisco, California, Aerogen, Inc. (2001).
Chambless, J. D. et al., "A three-dimensional computer model of four hypothetical mechanisms protecting biofilms from antimicrobials," Appl. Environ. Microbiol., 72(3):2005-2013 (2006).
Chapman, D., "Physicochemical Properties of Phospholipids and Lipid-Water Systems," In: Liposome Technology, Chapter 1, vol. I, Preparation of Liposomes, Gregoriadis G. (ed.), CRC Press, Inc., Boca Raton, Florida, pp. 1-18 (1984).
Chmiel, J. F. et al., "State of the art: why do the lungs of patients with cystic fibrosis become infected and why can't they clear the infection?", Respiratory Research, 4:8-20 (2003).

(56) References Cited

OTHER PUBLICATIONS

Clay. M. M. et al., "Assessment of jet nebulisers for lung aerosol therapy," Lancet, 2:592-594 (1983).

Comis, R. L., "Carboplatin in the treatment of non-small cell lung cancer: a review," Oncology, 50(2):37-41 (1993).

Costerton, J. W. et al., "Bacterial biofilms: A common cause of persistent infections," Science, 284:1318-1322 (1999).

Couvreur, P. et al., "Liposomes and nanoparticles in the treatment of intracellular bacterial infections," Pharmaceutical Research, 8(9):1079-1085 (1991).

Cynamon, M. H. et al., "Liposome-Encapsulated-Amikacin Therapy of *Mycobacterium avium* Complex Infection in Geige Mice," Antimicrobial Agents and Chemotherapy, 33(8):1179-1183 (1989).

Damaso, D. et al., "Susceptibility of current clinical isolates of Pseudomonas aeruginosa and enteric gram-negative bacilli to amikacin and other aminoglycoside antibiotics," The Journal of Infectious Diseases, 134:S394-S390 (1976).

Deamer, D. W. et al., "Liposome Preparation: Methods and Mechanisms," Chapter 1 in: Liposomes, Ostro, M. J. (ed.), Marcel Dekker, Inc., New York (1983), 27 pages.

Dees, C. et al., "The mechanism of enhanced intraphagocytic killing of bacteria by liposomes containing antibiotics," Veterinary Immunology and Immunopathology, 24:135-146 (1990).

Demaeyer, P. et al., "Disposition of liposomal gentamicin following intrabronchial administration in rabbits," Journal Microencapsulation, 10(1):77-88 (1993).

Deol, P. et al., "Lung specific stealth liposomes: stability, biodistribution and toxicity of liposomal antitubular drugs in mice," Biochemica et Biophysica Acta, 1334:161-172 (1997).

Dong, C. et al., "Acacia-gelatin microencapsulated liposomes: preparation, stability and release of acetylsalicylic acid," Pharmaceutical Research, 10(1):141-146 (1993).

Doring, G. et al., "Antibiotic therapy against Pseudomonas aeruginosa in cystic fibrosis: a European consensus," Eur Respir J., 16(4):749-767 (2000).

Drenkard, E. et al., "Pseudomonas biofilm formation and antibiotic resistance are linked to phenotypic variation," Nature, 416:740-743 (2002).

Ehlers, S. et al., "Liposomal amikacin for treatment of *M. avium* Infections in clinically relevant experimental settings," Zbl. Bakt., 284:218-231 (1996).

Fielding, R. M. et al., "Pharmacokinetics and Urinary Excretion of Amikacin in Low-Clearance Unilamellar Liposomes after a Single or Repeated Intravenous Administration in the Rhesus Monkey," Antimicrobial Agents and Chemotherapy, 43(3):503-509 (1999).

Fountain, M. W. et al., "Treatment of *Brucella canis* and *Brucella abortus* In vitro and in vivo by stable plurilamellar vesicle-encapsulated aminoolycosides," The Journal of Infectious Diseases, 152(3):529-535 (1985).

Geller, D. E. et al., "Pharmacokinetics and bioavailability of aerosolized tobramycin in cystic fibrosis," Chest, 122(1):219-226 (2002).

Gibson, R. L. et al., "Pathophysiology and management of pulmonary infections in cystic fibrosis," American Journal of Respiratory and Critical Care Medicine, 168(8):918-951 (2003).

Gibson, R. L. et al., "Significant microbiological effect of inhaled tobramycin in young children with cystic fibrosis," American Journal of Respiratory and Critical Care Medicine, 167(6):841-849 (2003).

Gilbert, B. E. et al., "Tolerance of volunteers to cyclosporine A-dilauroylphosphatidylcholine liposome aerosol," American Journal of Respiratory and Critical Care Medicine, 156(6):1789-1793 (1997).

Gleiser, C. A. et al., "Pathology of experimental respiratory anthrax in Macaca mulatta," Brit. J. Exp. Path., 44:416-426 (1963).

Gonzales-Rothi, R. J. et al., "Liposomes and pulmonary alveolar macrophages: functional and morphologic interactions," Experimental Lung Research, 17:687-705 (1991).

Goss, C. H. et al., "Update on cystic fibrosis epidemiology," Current Opinion in Pulmonary Medicine, 10(6):510-514 (2004).

Gunther, A. et al., "Surfactant alteration and replacement in acute respiratory distress syndrome," Respiratory Research, 2(6): 353-364 (2001).

Hagwood, S. et al., "Structure and properties of surfactant protein B," Biochimica et Biophysica Acta., 1408:150-160 (1998).

Hansen, C. R. et al., "Long-term azithromycin treatment of cystic fibrosis patients with chronic pseudomonas aeruginosa infection: an observational cohort study," Journal of Cystic Fibrosis, 4(1):35-40 (2005).

Hess, D. et al., "Medication nebulizer performance. Effects of diluent volume, nebulizer flow, and nebulizer brand," Chest, 110:498-505 (1996).

Hess, D. R., "Nebulizers: Principles and Performance," Respiratory Care, 45(6):609-622 (2000).

Hoffman, L. R. et al., "Aminoglycoside antibiotics induce bacterial biofilm formation," Nature, 436:1171-1175 (2005).

Howell, S. B., "Clinical applications of a novel sustained-release injectable drug delivery system: Depofoam Technology," Cancer Journal, 7:219-227 (2001).

Hrkach, J. S. et al., "Synthesis of poly(L-lactic acid-co-L-lysine) graft copolymers," Macromolecules, 28:4736-4739 (1995).

Hrkach, J. S. et al., "Poly(L-Lactic acid-co-amino acid) graft copolymers: A class of functional biodegradable biomaterials," In: Hydrogels and Biodegradable Polymers for Bioapplications, Chapter 8, ACS Symposium Series No. 627, Ottenbrite, R. M. et al. (eds.), American Chemical Society, pp. 93-102 (1996).

Huang, L. et al., "Progress of liposome's applications in biomedicine," International Journal of Biologicals, 29(3):130-132 and 137 (2006).

Hung, O. R. et al., "Pharmacokinetics of inhaled liposome-encapsulated fentanyl," Anesthesiology, 83(2): 277-284 (1995).

Hunt, B. E. et al., "Macromolecular mechanisms of sputum inhibition of tobramycin activity," Antimicrobial Agents and Chemotherapy, 39(1):34-39 (1995).

Ikegami, M. et al., "Surfactant protein metabolism in vivo," Biochimica et Biophysica Acta, 1408:218-225 (1998).

Ishii, F. et al., "Procedure for Preparation of Lipid Vesicles (Liposomes) Using the Coacervation (Phase Separation) Technique," Langmuir, 11(2):483-486 (1995).

Janoff, A. S. et al., "Unusual lipid structures selectively reduce the toxicity of amphotericin B," Proc. Nat. Acad. Sci. USA, 85:6122-6126 (1988).

Johansson, J., "Structure and properties of surfactant protein C," Biochimica et Biophysica Acta, 1408:161-172 (1998).

Katare, O. P. et al., "Enhanced in vivo Performance of LiposomalIndomethacin Derived From Effervescent Granule Based Proliposomes," J. Microencapsulation, 12(5):487-493 (1995).

Kesavalu, L. et al., "Differential effects of free and liposome encapsulated amikacin on the survival of *Mycobacterium avium* complex in mouse peritoneal macrophages," Tubercle, 71:215-218 (1990).

Kim, E. K. et al., "Pharmacokinetics of intravitreally injected liposomes encapsulated tobramycin in normal rabbits," Yonsei Medical Journal, 31(4):308-314 (1990).

Klemens, S. P. et al., "Liposome-encapsulated-gentamicin therapy of *Mycobacterium avium* complex infection in beige mice," Antimicrobial Agents and Chemotherapy, 34(6):967-970 (1990).

Knoch, M. et al., "The customised electronic nebuliser: a new category of liquid aerosol drug delivery systems," Expert Opin. Drug Deliv., 2(2):377-390 (2005).

Lagace, J. et al., "Liposome-encapsulated antibiotics: preparation, drug release and antimicrobial activity against Pseudomona aeruginosa," Journal Microencapsulation, 8(1) 53-61 (1991).

Landyshev, Y. S. et al., "Clinical and experimental aspects of liposomal hydrocortisone treatment of bronchial asthma," Ter. Arkh., 74(8):45-48 (2002).

Lass, J. S. et al., "New advances in aerosolised drug delivery: vibrating membrane nebuliser technology," Expert Opin Drug Deliv., 3(5):693-702 (2006).

Le Brun, P. P. H. et al., "A review of the technical aspects of drug nebulization," Pharmacy World & Science, 22(3):75-81 (2000).

(56) References Cited

OTHER PUBLICATIONS

Le Brun, P. P. H. et al., "Inhalation of tobramycin in cystic fibrosis part 1: The choice of a nebulizer," International Journal of Pharmaceutics, 189:205-214 (1999).
Le Brun, P. P. H. et al., "Inhalation of tobramycin in cystic fibrosis part 2: Optimization of the tobramycin solution for a jet and ultrasonic nebulizer," International Journal of Pharmaceutics, 189:215-225 (1999).
Le Brun, P. P. H. et al., "Dry powder inhalation of antibiotics in cystic fibrosis therapy: part 2. Inhalation of a novel colistin dry powder formulation: a feasibility study in healthy volunteers and patients," European Journal of Pharmaceutics and Biopharmaceutics, 54:25-32 (2002).
Lutwyche, P. et al., "Intracellular delivery and antibacterial activity of gentamicin encapsulated in pH-sensitive liposomes," Antimicrobial Agents and Chemotherapy, 42(10):2511-2520 (1998).
Marier, J. F. et al., "Liposomal tobramycin against pulmonary infections of Pseudomonas aeruginosa: a pharmacokinetic and efficacy study following single and multiple intratracheal administrations in rats," Journal Antimicrobial Chemotherapy, 52:247-252 (2003).
Marier, J-F. et al., "Pharmacokinetics and efficacies of liposomal and conventional formulations of tobramycin after intratracheal administration in rats with pulmonary burkholderia cepacia infection," Antimicrobial Agents and Chemotherapy, 46(12):3776-3781 (2002).
Martini, W. Z. et al., "Lung surfactant kinetics in conscious pigs," Am J Physiol., 277(1 Pt 1): E187-E195 (1999).
McAllister, S. M. et al., "Antimicrobial properties of liposomal polymyxin B," Journal of Antimicrobial Chemotherapy, 43:203-210 (1999).
Mendelman, P. M. et al., "Aminoglycoside penetration, inactivation, and efficacy in cystic fibrosis sputum," American Review of Respiratory Disease, 132(4):761-765 (1985).
Mohanty, B. et al., "Systematic of alcohol-induced simple coacervation in aqueous gelatin solutions," Biomacromolecules, 4:1080-1086 (2003).
Morgan, J. R. et al., "Preparation and properties of liposome-associated gentamicin," Antimicrobial Agents and Chemotherapy, 17(4):544-548 (1980).
Myers, M. A. et al., "Pulmonary effects of chronic exposure to liposome aerosols in mice," Experimental Lung Research, 19:1-19 (1993).
Nasu, M. et al., "Appropriate use of antimicrobial agents," Selection of Anti-infective, Clinic in Japan (Special Number) Infection Disease Study in New Era (first volume), 2003, 61st issue, pp. 718-723.
Newton, D. W. et al., Chapter 4: "Coacervation: Principles and Applications," In: Polymers for Controlled Drug Delivery, Tarcha, P. J. (ed.), CRC Press, Boca Raton, pp. 67-81 (1991).
Nightingale, S. D. et al., "Liposome-encapsulated gentamicin treatment of *Mycobacterium avium-Mycobacterium intracellulare* complex bacteremia in AIDS patients," Antimicrobial Agents and Chemotherapy, 37(9):1869-1872 (1993).
Niven, R. W. et al., "Nebulization of liposomes. I. Effects of lipid composition,"Pharmaceutical Research, 7(11):1127-1133 (1990).
Niven, R. W. et al., "Nebulization of liposomes. II. The effects of size and modeling of solute release profiles," Pharmaceutical Research, 8(2):217-221 (1991).
Niven, R. W. et al., "Nebulization of liposomes. III. The effects of operating conditions and local environment," Pharmaceutical Research, 9(4):515-520 (1992).
Omri, A. et al., "Incorporation, release and in-vitro antibacterial activity of liposomal aminoglycosides against Pseudomonas aeruginosa," Journal Antimicrobial Chemotherapy, 36(4):631-639 (1995).
Omri, A. et al., "Comparison of the bactericidal action of amikacin, netilmicin and tobramtcin in free and liposomal formulation against pseudomonas aeruginosa," Chemotherapy, 42:170-176 (1996).
Omri, A. et al., "Pulmonary retention of free and liposome-encapsulated tobramycin after intratracheal administration in uninfected rats and rats infected with Pseudomonas aeruginosa," Antimicrobial Agents and Chemotherapy, 38(5):1090-1095 (1994).
Pai, V. B. et al., "Efficacy and safety of aerosolized tobramycin in cystic fibrosis," Pediatric Pulmonology, 32(4):314-327 (2001).
Papahadjopoulos, D. et al., "Phospholipid model membranes. I. Structrual characteristics of hydrated liquid crystals," Biochimica et Biophysica Acta, 135:624-638 (1967).
Parsek, M. R. et al., "Acyl-homoserine lactone quorum sensing gram-negative bacteria: a signaling mechanism involved in associations with higher organisms," Proc. Nat. Acad. Sci., 97(16):6789-6793 (2000).
Patton, J. S. et al., "The lungs as a portal of entry for systemic drug delivery," Proc. Am. Thor. Soc., 1:338-344 (2004).
Petersen, E. A. et al., "Liposomal amikacin: improved treatment of *Mycibacterium avium* complex infection in the beige mouse model," Journal Antimicrobial Chemotherapy, 38:819-828 (1996).
Petkowicz, J. et al., "Hypoglycemic Effect of Liposome-Entrapped Insulin Administered by Various Routes into Normal Rats," Pol. J. Pharmacal. Pharrn., 41:299-304 (1989).
Pilewski, J. M. et al., "Role of CFTR in airway disease," Physiological Reviews, 79(1):5215-5255 (1999).
Poyner, E. A. et al., "A comparative study on the pulmonary delivery of tobramycin encapsulated into liposomes and PLA microspheres following intravenous and endotracheal delivery," Journal of Controlled Release, 35(1):41-48 (1995).
Poyner, E. A. et al., "Preparation, properties and the effects of free and liposomal tobramycin on siderophore production by Pseudomonas aeruginosa," Journal of Antimicrobial Chemotherapy, 34:43-52 (1993).
Price, C. I. et al., "Liposome delivery of aminoglycosides in burn wounds," Surgery, Gynecolooy & Obstetrics, 174:414-418 (1992).
Price, C. I. et al., "Liposome encapsulation: a method for enhancing the effectiveness of local antibiotics," Surgery, 115(4):480-487 (1994).
Price, C. I. et al., "Enhanced effectiveness of intraperitoneal antibiotics administered via liposomal carrier," Arch Surgery, 124:1411-1415 (1989).
Price, K. E. et al., "Amikacin, an aminoglycoside with marked activity against antibiotic-resistant clinical isolates," The Journal of Infectious Diseases, 134:S249-S261 (1976).
Ramsammy, L. S. et al., "The effect of gentamicin on the biophysical properties of phosphatidic acid liposomes is influenced by the O—C=O group of the lipid," Biochemistry, 27:8249-8254 (1988).
Ramsey, B. W. et al., "Intermittent administration of inhaled tobramycin in patients with cystic fibrosis. Cystic Fibrosis Inhaled Tobramycin Study Group," The New England Journal of Medicine, 340(1):23-30 (1999).
Ramsey, B. W. et al., "Efficacy of aerosolized tobramycin in patients with cystic fibrosis," The New England Journal of Medicine, 328:1740-1746 (1993).
Roehrborn, A. A. et al., "Lipid-based slow-release formulation of amikacin sulfate reduces foreign body-associated infections in mice," Antimicrobial Agents and Chemotherapy, 39(8):1752-1755 (1995).
Sabra, W. et al., "Physiological responses of pseudomonas aeruginosa PAO1 to oxidative stress in controlled microaerobic and aerobic cultures," Microbiology, 148:3195-3202 (2002).
Schentag, J. J., Antimicrobial action and pharmacokinetics/pharmacodynamics: the use of AUIC to improve efficacy and avoid resistance, Journal of Chemotherapy, 11(6):426-439 (1999).
Schiffelers, R. M. et al., "Therapeutic efficacy of liposomal gentamicin in clinically relevant rat models," International Journal of Pharmaceutics, 214:103-105 (2001).
Schiffelers, R. M. et al., "In vivo synergistic interaction of liposomecoencapsulated gentamicin and ceftazidime," Journal Pharmacology Experimental Therapeutics, 298(1):369-375 (2001).
Schreier, H. et al., "Pulmonary delivery of amikacin liposomes and acute liposome toxicity in the sheep," International Journal of Pharmaceutics, 87(1-3):183-193 (1992).
Schreier, H. et al., "Pulmonary delivery of liposomes," Journal of Controlled Release, 24(1):209-223 (1993).

(56) References Cited

OTHER PUBLICATIONS

Stott, P. W. et al., "Characterization of complex coacervates of some tricyclic antidepressants and evaluation of their potential for enhancing transdermal flux," Journal of Controlled Release, 41(3):215-227 (1996).
Sermet-Gaudelus, I. et al., "Nebulized antibiotics in cystic fibrosis," Paediatric Drugs, 4(7):455-467 (2002).
Shah, S. P. et al., "Liposomal amikacin dry powder inhaler: effect of fines on in vitro performance," AAPS PharmSciTech, 5(4):e65:1-7 (2004).
Singh, P. K. et al., "Quorum-sensing signals indicate that cystic fibrosis lungs are infected with bacterial biofilms," Nature, 407:762-764 (2000).
Skubitz, K. M. et al., "Inhalational interleukin-2 liposomes for pulmonary metastases: a phase I clinical trial," Anti-Cancer Drugs, 11(7): 555-563 (2000).
Swenson, K. A. et al., "Pharmacokinetics and in vivo activity of liposome-encapsulated gentamicin," Antimicrobial Agents and Chemotherapy, 34(2)235-240 (1990).
Swenson, C. E. et al., "Liposomal aminoglycosides and TLC G-65," Aids Patient Care, pp. 290-296 (1991).
Szoka, F. Jr. et al., "Comparative properties and methods of preparation of lipid vesicles (liposomes)," Ann. Rev. Biophys. Bioeng., 9:467-508 (1980).
Taylor, K. M. G. et al., "The influence of liposomal encapsulation on sodium cromoglycate pharmacokinetics in man," Pharmaceutical Research, 6(7):633-636 (1989).
Ten, R. M. et al., "Interleukin-2 liposomes for primary immune deficiency using the aerosol route," International Immunopharmacology, 2(2-3):333-344 (2002).
Thomas, D. A. et al., "Acute effects of liposome aerosol inhalation on pulmonary function in healthy human volunteers," Chest, 99(5):1268-1270 (1991).
Thomasin, C. et al., "Drug microencapsulation by PLA/PLGA coacervation in the light of thermodynamics. 2. Parameters determining microsphere formation," Journal of Pharmaceutical Sciences, 87(3):269-275 (1998).
Trafny, E. A. et al., "Effects of free and liposome-encapsulated antibiotics on adherence of Pseudomonas aeruginosa to collagen type I," Antimicrobial Agents and Chemotherapy, 39(12):2645-2649 (1995).
Vecellio, L., "The mesh nebuliser: a recent technical innovation for aerosol delivery," Breathe, 2(3):253-260 (2006).
Veldhuizen, R. et al., "The role of lipids in pulmonary surfactant," Biochimica et Biophysica Acta, 1408:90-108 (1998).
Vidgren, M. et al., "A study of $^{99m}$ technetium-labelled beclomethasone dipropionate dilauroylphosphatidylcholine liposome aerosol in normal volunteers," International Journal of Pharmaceutics, 115:209-216 (1995).
Vitas, A. I. et al., "Effect of composition and method of preparation of liposomes on their stability and interaction with murine monocytes infected with *Brucella abortus*," Antimicrobial Agents and Chemotherapy, 40(1):146-151 (1996).
Wang, W. et al., "Research progress in pulmonary administration of liposome," Journal of Shenyang Pharmaceutical University, 17(3):226-229 (2000).
Westerman, E. M. et al., "Effect of nebulized colistin sulphate and colistin sulphomethate on lung function in patients with cystic fibrosis: a pilot study," Journal of Cystic Fibrosis, 3(1):23-28 (2004).
Whitehead, T. C. et al., "Kinetics and Toxicity of Liposomal and Conventional Amikacin in a Patient with Multidrug-Resistant Tuberculosis," Eur J Clin Microbiol. Infect. Dis., 17:794-797 (1998).
Wichert, B. V. et al., "Amikacin liposomes: characterization, aerosolization, and in vitro activity against *Mycobacterium avium*-intracellulare in alveolar macrophages," International Journal of Pharmaceutics, 78(2-3):227-235 (1992).
Wolff, R. K. et al., "Toxicologic testing of inhaled pharmaceutical aerosols," Critical Reviews in Toxicology, 23(4):343-369 (1993).
Worlitzsch, D. et al., "Effects of reduced mucus oxygen concentration in airway pseudomonas infections of cystic fibrosis patients," J. Clin. Invest., 109:317-325 (2002).
Xiu, L. et al., "Drug Resistant Analysis of Pseudomonas aeruginosa in Patients with Mechanical Ventilation," Med. J. Chin. PLA, 27(6):544-545 (2002).
Yanagihara, K. et al., "Design of anti-bacterial drug and anti-Mycobacterial drug for drug delivery system," Current Pharmaceutical Design, 8:475-482 (2002).
Zeng, S. et al., "Intravitreal Pharmacokinetics of Liposome-encapsulated Amikacin in a Rabbit Model," Opthamology, 100:1640-1644 (1993).
Zhang, J. H. et al., "A Novel Method to Prepare Liposomes Containing Amikacin," Journal Microencapsulation, 16(4):511-516 (1999).
Zhang, X. et al., "Antibacterial drug treatment of community acquired pneumonia," Chinese Journal of Respiratory and Critical Care Medicine, 4(4):258-260 (2005).
Office Action for U.S. Appl. No. 12/598,830, mailed Apr. 18, 2014.
Office Action for U.S. Appl. No. 12/250,412, mailed Mar. 24, 2014.
Office Action for Chilean Application No. 814-2011, dated Apr. 8, 2014.
Office Action for Chinese Patent Application No. 200980140740.2, dated Mar. 5, 2014.
Office Action for Israel Patent Application No. 212268, dated Dec. 9, 2013.
Office Action for Japanese Patent Application No. 2011-532180, dated May 1, 2014.
Office Action for Japanese Patent Application No. 2011-532180, dated Jan. 23, 2014.
Office Action for Russia Patent Application No. 2011119018, dated Mar. 5, 2014.
Office Action for Ukraine Patent Application No. 201105955, dated Jun. 7, 2013.
Office Action for U.S. Appl. No. 13/480,246, mailed Apr. 10, 2014.
Office Action for Israel Patent Application No. 168279, dated Mar. 19, 2014.
Official Action for Korean Patent Application No. 10-2013-7010499, dated Sep. 2, 2013.
Office Action for Mexican Patent Application No. MX/a/2010/000195, mailed May 31, 2013.
Office Action for Indian Patent Application No. 353/DELNP/2008, dated Jul. 26, 2013.
Office Action for Japanese Patent Application No. 2008-522895, dated Aug. 27, 2013.
Office Action for Chinese Application No. 201310149581.0, mailed Apr. 21, 2014.
Office Action for European Application No. 07754853, mailed Feb. 3, 2014.
Office Action for Japanese Patent Application No. 2009-504281, mailed Nov. 1, 2013.
Office Action for Korean Patent Application No. 10-2013-7031379, dated Feb. 25, 2014.
Office Action for Japanese Application No. 2013-146934, mailed May 26, 2014.
Office Action for Korean Application No. 10-2014-7005780, Jun. 26, 2014.
Office Action for U.S. Appl. No. 12/424,177, mailed Jul. 21, 2014.
Office Action for U.S. Appl. No. 12/424,177, mailed Dec. 24, 2013.
European Search Report for European Patent Application No. 13175824, mailed Sep. 16, 2013.
Office Action for Japanese Application No. 2013-167610, dated Aug. 8, 2014.
Office Action for U.S. Appl. No. 12/983,659, mailed Dec. 2, 2013.
Office Action for U.S. Appl. No. 12/983,659, mailed Jun. 17, 2014.
Office Action for European Patent Application No. 06847502.9, mailed Oct. 14, 2013.
Office Action for European Patent Application No. 06847502.9, mailed Jul. 16, 2014.
Office Action for U.S. Appl. No. 14/080,922, mailed Jun. 12, 2014.
Office Action for Japanese Patent Application No. 2009-504301, mailed Oct. 31, 2013.
Office Action for U.S. Appl. No. 11/696,343, mailed May 23, 2014.

(56) References Cited

OTHER PUBLICATIONS

International Search Report and Written Opinion for International Application No. PCT/US2013/042113, mailed Sep. 4, 2013.
Dequin, P. F. et al., "Urinary excretion reflects lung deposition of aminoglycoside aerosols in cystic fibrosis," Eur. Respir. J., 18(2):316-322 (2001).
Meers, P. et al., "Biofilm penetration, triggered release and in vivo activity of inhaled liposomal amikacin in chronic Pseudomonas aeruginosa lung infections," Journal of Antimicrobial Chemotherapy, 61(4):859-868 (2008).
Schiffelers, R. et al., "Liposome-encapsulated aminoglycosides in pre-clinical and clinical studies," Journal of Antimicrobial Chemotherapy, 48:333-344 (2001).
Office Action for U.S. Appl. No. 12/598,830, mailed Nov. 28, 2014, 8 pages.
Office Action for Chilean Application No. 814-2011, dated Nov. 4, 2014, 5 pages.
Office Action for Indonesian Application No. W00201101412, dated Feb. 28, 2014, 1 page.
Office Action for Philippine Application No. 12011500726, mailed Apr. 24, 2014, 1 page.
Second Written Opinion for Singapore Application No. 201102419-7, mailed Sep. 4, 2014, 13 pages.
Office Action for Japanese Application No. 2014-075240, dated Mar. 9, 2015, 2 pages.
Office Action for Israel Application No. 168279, dated Aug. 25, 2014, 2 pages.
Generics [UK] Ltd.'s Notice of Opposition for European Application No. 06787716.7, filed Jun. 4, 2014, 17 pages.
Patentee's Response to Notice of Opposition and Declaration of Lee Leserman for European Application No. 06787716.7, filed Jan. 16, 2015, 58 pages.
Office Action for Israel Application No. 188406, dated Aug. 25, 2014, 2 pages.
Office Action for Chinese Application No. 201310149581.0, mailed Oct. 17, 2014, 7 pages.
Office Action for Israel Application No. 216401, dated May 27, 2014, 2 pages.
Office Action for Canadian Application No. 2,838,108, mailed Jan. 6, 2015, 3 pages.
Office Action for Canadian Application No. 2,853,611, mailed Jul. 9, 2014, 3 pages.
Office Action for Canadian Application No. 2,853,611, mailed Mar. 5, 2015, 3 pages.
Office Action for Japanese Application No. 2014-040222, dated Feb. 10, 2015, 1 page.
European Search Report for European Application No. 14183066.1, mailed Dec. 16, 2014, 11 pages.
Office Action for Canadian Application No. 2,838,111, dated Nov. 27, 2014, 4 pages.
Office Action for U.S. Appl. No. 14/080,922, mailed Sep. 18, 2014, 10 pages.
Office Action for U.S. Appl. No. 14/080,922, mailed Mar. 3, 2015, 16 pages.
Office Action for European Application No. 07754936.8, mailed Sep. 2, 2014, 7 pages.
Office Action for U.S. Appl. No. 11/696,343, mailed Feb. 3, 2015, 11 pages.
International Preliminary Report on Patentability for International Application No. PCT/US2013/042113, dated Nov. 25, 2014, 9 pages.
Bakker-Woudenberg, I. A. J. M. et al., "Long-Circulating Sterically Stabilized Liposomes in the Treatment of Infections," Method in Enzymology, Available online Feb. 21, 2005, 391:228-260 (2005).
Cooksey, R. C. et al., "Antimicrobial susceptibility patterns of *Streptococcus pneumoniae*," Antimicrobial Agents and Chemotherapy, 13(4):645-648 (1978).
Del Porto, P. et al., "Dysfunctional CFTR alters the bactericidal activity of human macrophages against Pseudomonas aeruginosa," PLoS ONE, 6(5):e19970 (2011).

Johnston, M. J. W. et al., "Therapeutically optimized rates of drug release can be achieved by varying the drug-to-lipid ratio in liposomal vincristine formulations," Biochimica et Biophysica Acta, 1758:55-64 (2006).
Li, Z. et al., "Characterization of nebulized liposomal amikacin (Arikace) as a function of droplet size," Journal of Aerosol Medicine and Pulmonary Drug Delivery, 21(3):245-253 (2008).
Press Release, "Transave Announces Positive Phase II Results for Once-Daily Arikace in the Treatment of Cystic Fibrosis Patients Who Have Pseudomonas Lung Infections," Presented at the European Cystic Fibrosis Society Conference, Monmouth Junction, NJ, Jun. 13, 2008, 3 pages.
Schlegel, L. et al., "In-vitro killing activity of combinations of beta-lactam agents with aminoglycosides against penicillin-resistant pneumococci," The Journal of Antimicrobial Chemotherapy, 39(1):95-98 (1997).
Tateda, K. et al., "Efficacy of beta-lactam antibiotics combined with gentamicin against penicillin-resistant pneumococcal pneumonia in CBA/J mice," The Journal of Antimicrobial Chemotherapy, 43(3):367-371 (1999).
Bilodeau, M. et al.,"Kanamycin aerosol therapy in 200 cases of bronchopulmonary suppurations," Can. Med. Assoc. J., 89:537-541 (1963) (with English Abstract).
Chan, C. H. S. et al., "Mycobacteria as a cause of infective exacerbation in bronchiectasis," Postgrad. Med. J., 68:896-899 (1992).
Colardyn, F., "The efficacy and safety of isepamicin and ceftazidime compared with amikacin and ceftazidime in acute lower respiratory tract infection," Journal of Chemotherapy, 7(2):129-135 (1995).
Coleman, L. T. et al., "Bronchiectasis in children," Journal of Thoracic Imaging, 10(4)268-279 (1995).
Cremades, M. J. et al., "Repeated pulmonary infection by Nocardia asteroides complex in a patient with bronchiectasis," Respiration, 65:211-213 (1998).
Crowther, N. R. et al., "Inhaled aminoglycoside (gentamicin) in bronchiectasis: Dry powder vs. nebulization vs. intravenous therapy," Clinical and Investigative Medicine, Annual Meeting of the Canadian Society for Clinical Investigation, The Royal College of Physicians and Surgeons of Canada and Participating Societies, Toronto, Canada, Abstract 530 (Sep. 24-27, 1998).
Currie, D. C., "Nebulisers for bronchiectasis," Thorax, 52(Suppl. 2):S72-S74 (1997).
Dally, M. B. et al., "Ventilatory effects of aerosol gentamicin," Thorax, 33:54-56 (1978).
Dickie, K. J. et al., "Ventilatory effects of aerosolized kanamycin and polymyxin," Chest, 63(5):694-697 (1973).
El-Din, M. A. T. et al., "Nebulizer therapy with antibiotics in chronic suppurative lung disease," Journal of Aerosol Medicine, 7(4):345-350 (1994).
Eller, J. M. et al., "The therapy of bronchiectasis," Deutsche Medizinische Wochenschrift, 118(44):1608-1610 (1993).
Farber, J. E. et al., "The use of aerosol penicillin and streptomycin in bronchopulmonary infections," California Medicine, 73(3):214-217 (1950).
Finke, W., "Long-term antibiotic therapy in chronic bronchitis and infectious asthma. Control and prevention of bronchopulmonary disease." Antibiotics and Chemotherapy, 4(3):319-329 (1954).
Garcia, A. T., "Efficacy of amikacin sulfate in lower respiratory infections," Investigacion Medica Internacional, 9(3):235-240 (1982) (with English Abstract).
Goldman, J. M. et al., "Inhaled micronised gentamicin poweder: a new delivery system," Thorax, 45:939-940 (1990).
Graczyk, J. et al., "*Staphylococcal pneumonia*—analysis of material of patients treated in lung diseases hospital in years 1981-1994," Pneumonologia I Alergologia Polska, 65(11-12):767-774 (1997) (with English Abstract).
Greene, K. E. et al., "Radiographic changes in acute exacerbations of cystic fibrosis in adults: A pilot study," AJR, 163:557-562 (1994).
Helbich, T. et al., "High-resolution computed tomography of the lung in young patients with cystic fibrosis," Radiologe, 33(3):142-146 (1993) (English Abstract).
Hewitt, W. L. et al., "Antibiotic therapy of abscess of the lung and bronchiectasis," California Medicine, 76(5):319-324 (1952).

(56) References Cited

OTHER PUBLICATIONS

Hubble, D., "Discussion on respiratory catarrh in children," Proceedings of the Royal Society of Medicine, 52(9):701-710 (1959).
Ikemoto, H. et al., "Susceptibility of bacteria isolated from the patients with lower respiratory tract infections to antibiotics," The Japanese Journal of Antibiotics, 42(11):2350-2353 (1989).
IP, M. S. M. et al., "Bronchiectasis and related disorders," Respirology, 1:107-114 (1996).
Knox, K. et al., "Chronic bronchitis. An attempt to control chronic infection with Haemophilus influenzae by aerosol therapy," The Lancet, pp. 120-122 (1955).
Lin, H.-C. et al., "Inhaled gentamicin reduces airway neutrophil activity and mucus secretion in bronchiectasis," Am. J. Respir. Crit. Care Med., 155:2024-2029 (1997).
Marcotte, G. V. et al., "Chronic productive cough and bronchiectasis in a 40-year-old woman," Annals of Allergy, Asthma & Immunology, 78(6):559-564 (1997).
Mariotti, A. B. et al., "Aerosol therapy with tobramycin in exacerbations of chronic obstructive lung disease (7 cases)," 66(2):198-202 (1996) (with English Abstract).
Marwah, O. S. et al., "Bronchiectasis. How to identify, treat and prevent," Postgrad. Med., 97(2):149-150, 153-156, 159 (1995) (Abstract).
Mombelli, G. et al., "Anti-pseudomonas activity in bronchial secretions of patients receiving amikacin or tobramycin as a continuous infusion," Antimicrobial Agents and Chemotherapy, 19(1):72-75 (1981).
Nakazawa, S. et al., "Studies on a new aminoglycoside antibiotic, amikacin (BB-K8) in pediatrics," The Japanese Journal of Antibiotics, 27(4):438-445 (1974).
Oizumi, K. et al., "Therapeutic effect of amikacin for infections with gram-negative bacilli, especially for stubborn respiratory infections," The Japanese Journal of Antibiotics, 31(1):15-23 (1978).
Olsen, A. M., "Streptomycin aerosol in the treatment of chronic bronchiectasis: preliminary report," Staff Meetings of the Mayo Clinic, pp. 53-54 (1946).
Olsen, A. M., "Nebulization therapy in bronchiectasis: The use of penicillin and streptomycin aerosols," In: Collected Papers of The Mayo Clinic and The Mayo Foundation, Hewitt, R. M. et al. (eds.), 38:579-586 (1946).
Olsen, A. M., "Nebulization therapy in bronchiectasis: The use of penicillin and streptomycin aerosols," J.A.M.A., 134(11):947-953 (1947).
Paradisi, F. et al, "Acute and chronic bronchopulmonary infections and aminoglycoside antibiotics," Chemioterapia Antimicrobica, 1(2):224-227 (1978).
Pines, A. et al., "Treatment of severe pseudomonas infections of the bronchi," British Medical Journal, 1:663-665 (1970).
Pines, A. et al., "Gentamicin and colistin in chronic purulent bronchial infections," British Medical Journal, 2:543-545 (1967).
Potter, B. P., "Aerosol antibiotic therapy in suppurative diseases of the lung and bronchi," Aerosol Antibiotic Therapy, 25:436-448 (1949).
Shima, K. et al., "A study of amikacin (BB-K8) on the clinical effects on the respiratory infection," Chemotherapy, 23(6):2128-2130 (1975) (with English Abstract).
Smith, A. L. et al., "Safety of aerosol tobramycin administration for 3 months to patients with cystic fibrosis," Pediatric Pulmonology, 7:265-271 (1989).
Takamoto, M. et al., "Imipenem/cilastatin sodium alone or combined with amikacin sulfate in respiratory infections," The Japanese Journal of Antibiotics, 47(9):1131-1144 (1994) (with English Abstract).
Terzano, C. et al., "Tobramycin aerosol: could the delivery system influence the particle size and deposition in the lower airways?" Recenti. Prog. Med., 89(5):245-249 (1998) (English Abstract).
Van Der Straeten, M. et al., "Amikacin in the treatment of gram-negative bronchopulmonary infections," The Journal of Infectious Diseases, 134:S391-S393 (1976).
Zlatanov, Zi. et al., "Gentamycin-pharmachim. Aerosol inhalation treatment of patients with chronic bronchitis," Medico Biologic Information 2, pp. 5-8 (1976).
Office Action for U.S. Appl. No. 13/664,181, mailed Aug. 22, 2013, 9 pages.
Office Action for U.S. Appl. No. 13/675,559, mailed Aug. 20, 2013, 9 pages.
Office Action for U.S. Appl. No. 13/675,587, mailed Aug. 21, 2013, 9 pages.
Office Action for U.S. Appl. No. 14/198,724, mailed May 11, 2015, 7 pages.
Office Action for Canadian Application No. 2,739,954, mailed Apr. 28, 2015, 4 pages.
Supplementary European Search Report for European Application No. 09821103.0, mailed Aug. 12, 2015, 10 pages.
Office Action for Israel Application No. 212268, dated Apr. 28, 2015, 2 pages.
Office Action for Philippine Application No. 12011500726, mailed May 29, 2015, 2 pages.
Office Action for Australian Application No. 2014201765, dated Apr. 9, 2015, 3 pages.
Office Action for U.S. Appl. No. 13/566,707, mailed May 27, 2015, 11 pages.
Office Action for Japanese Application No. 2009-504281, mailed Aug. 3, 2015, 4 pages.
Office Action for Japanese Application No. 2013-146934, mailed Mar. 5, 2015, 4 pages.
Office Action for U.S. Appl. No. 12/424,177, mailed Apr. 17, 2015, 8 pages.
Office Action for U.S. Appl. No. 12/983,659, mailed Apr. 6, 2015, 7 pages.
Office Action for Japanese Application No. 2014-093375, dated Apr. 7, 2015, 2 pages.
Office Action for New Zealand Application No. 700983, mailed Oct. 5, 2015, 4 pages.
Clancy, J. P. et al., "Phase II studies of nebulised Arikace in CF patients with Pseudomonas aeruginosa infection," Thorax, 68(9):818-825 (2013).
Li, Z. et al., "Nebulization of liposomal amikacin formulations: SLIT Amikacin," Respiratory Drug Delivery, 3:801-804 (2006).
Perkins, W. R. et al., "Aerosolization of liposomal amikacin (Arikace) using different nebulizers: Selection of the eflow nebulizer," Poster and Oral Presentation at North American Cystic Fibrosis Conference (Oct. 2007), Pediatric Pulmonology, 42(30):356-357, abs. 434, 12 pages.
Notification of Reexamination for Chinese Application No. 200980140740.2, dated Aug. 26, 2015, 11 pages.
Notice of Grounds for Rejection for Korean Application No. 2011-7008430, dated Sep. 3, 2015, 3 pages.
Office Action for U.S. Appl. No. 12/424,177, mailed Oct. 29, 2015, 7 pages.
Office Action for U.S. Appl. No. 12/983,659, mailed Oct. 29, 2015, 9 pages.
Office Action for Japanese Application No. 2014-196130, mailed Jul. 14, 2015, 4 pages.
Office Action for U.S. Appl. No. 14/080,922, mailed Aug. 10, 2015, 17 pages.
Office Action for Japanese Application No. 2014-165736, mailed Jul. 9, 2015, 10 pages.
Office Action for U.S. Appl. No. 14/198,724, mailed Mar. 11, 2016, 9 pages.
Office Action for Canadian Application No. 2,739,954, mailed Mar. 4, 2016, 7 pages.
Decision of Reexamination for Chinese Application No. 200980140740.2, dated Feb. 14, 2016, 25 pages.
First Examination Report for Indian Application No. 2600/DELNP/2011, dated Aug. 24, 2015, 2 pages.
Office Action for Philippine Application No. 12011500726, mailed Nov. 27, 2015, 3 pages.
Office Action for Japanese Application No. 2014-075240, mailed Dec. 10, 2015, 5 pages.
Office Action for Israel Patent Application No. 188406, dated Aug. 3, 2015, 2 pages.

(56) References Cited

OTHER PUBLICATIONS

Office Action for Chinese Application No. 201310149581.0, mailed Jun. 23, 2015, 8 pages.
Office Action for Israel Application No. 216401, dated Aug. 3, 2015, 3 pages.
Office Action for U.S. Appl. No. 14/987,508, mailed Apr. 1, 2016, 12 pages.
First Office Action for Chinese Application No. 201380030763.4, issued Jan. 6, 2016, 7 pages.
Supplementary European Search Report for European Application No. 13793204.2, mailed Sep. 25, 2015, 5 pages.
Blaser, J. et al., "Once daily dosing of aminoglycosides," Eur. Clin. Microbiol. Infect. Dis., 14(12):1029-1038 (1995).
Labiris, N. R. et al., "Pulmonary drug delivery. Part II: The role of inhalant delivery devices and drug formulations in Therapeutic effectiveness of aerosolized medications," Br.J.Clin.Pharmacol., 56(6):600-612 (2003).
Majumdar, S. et al., "Efficacies of Liposome-Encapsulated Streptomycin and Ciprofloxacin against *Mycobacterium avium-M. intracellulare* Complex Infections in Human Peripheral Blood Monocyte/Macrophages," Antimicrobial Agents and Chemotherapy, 36(12):2808-2815 (Dec. 1992).
Maurer, N. et al., "Anomalous solubility behavior of the antibiotic ciprofloxacin encapsulated in liposomes: a $^1$H-NMR study," Biochimica et Biophysica Acta, 1374:9-20 (1998).
Perkins, W. R. et al., "Role of lipid polymorphism in pulmonary surfactant," Science, 273:330-332 (Jul. 1996).
Ulrich, A. S., "Biophysical aspects of using liposomes as delivery vehicles," Bioscience Reports, 22(2):129-150 (Apr. 2002).
Notice of Grounds for Rejection for Korean Application No. 2011-7008430, dated Jul. 21, 2016, 4 pages.
Office Action for U.S. Appl. No. 14/809,127, mailed Jun. 16, 2016, 10 pages.
Office Action for U.S. Appl. No. 14/809,128, mailed Jun. 17, 2016, 10 pages.
Office Action for U.S. Appl. No. 12/424,177, mailed May 20, 2016, 5 pages.
Office Action for U.S. Appl. No. 12/983,659, mailed May 20, 2016, 6 pages.
Notice of Reasons for Rejection for Japanese Application No. 2014-222230, mailed Aug. 1, 2016, 6 pages.
Office Action for U.S. Appl. No. 15/093,180, mailed Jun. 24, 2016, 8 pages.
Supplementary European Search Report for European Application No. 16156099.0, mailed Jul. 25, 2016, 7 pages.
Office Action for Canadian Application No. 2,896,083, mailed Jun. 3, 2016, 6 pages.
Office Action for U.S. Appl. No. 15/066,346, mailed Jul. 21, 2016, 9 pages.
Office Action for U.S. Appl. No. 15/066,360, mailed Jul. 20, 2016, 10 pages.
Office Action for U.S. Appl. No. 11/696,343, mailed Jun. 10, 2016, 11 pages.
Office Action for European Application No. 13793204.2, mailed Jul. 15, 2016, 8 pages.
Office Action for New Zealand Application No. 700983, mailed Jun. 2, 2016, 2 pages.
Ciofu, O. et al., "Occurrence of Hypermutable Pseudomonas aeruginosa in Cystic Fibrosis Patients is Associated with the Oxidative Stress Caused by Chronic Lung Inflammation," Antimicrobial Agents and Chemotherapy, 49(6):2276-2282 (Jun. 2005).
ClinicalTrials.gov, "Safety and Efficacy Study of Ciprofloxacin for Inhalation in Patients With Non-Cystic Fibrosis Bronchiectasis 'ORBIT-1'", Identifier: NCT00889967, First Received: Apr. 27, 2009, 3 pages.
Cymbala, A. A. et al., "The Disease-Modifying Effects of Twice-Weekly Oral Azithromycin in Patients with Bronchiectasis," Treat Respir. Med. 2005;4(2):117-122.
Desai, T. R. et al., "Determination of surface free energy of interactive dry powder liposome formulations using capillary penetration technique," Colloids and Surfaces B: Biointerfaces, 22:107-113 (2001).
Jayaraman, S. et al., "Noninvasive in vivo fluorescence measurement of airway-surface liquid depth, salt concentration, and pH," J. Clin. Invest. 107:317-324 (2001).
Mercer, R. R. et al., "Cell Number and Distribution in Human and Rat Airways," Am. J. Respir. Cell Mol. Biol., 10:613-624 (1994).
Oh, Y-K et al., "Formulation and Efficacy of Liposome-Encapsulated Antibiotics for Therapy of Intracellular *Mycobacterium avium* Infection," Antimicrobial Agents and Chemotherapy, 39(9):2104-2111 (Sep. 1995).
Rau, J. L. et al., "Performance Comparison of Nebulizer Designs: Constant-Output, Breath-Enhanced, and Dosimetric," Respir. Care 2004;49(2):174-179.
Schaad, U. B. et al., "Efficacy of inhaled amikacin as adjunct to intravenous combination therapy (ceftazidime and amikacin) in cystic fibrosis," Journal of Pediatrics, 111(4):599-605 (Oct. 1987).
Tarran, R., "Regulation of Airway Surface Liquid Volume and Mucus Transport by Active Ion Transport," Proc. Am. Thorac. Soc., 1:42-46 (2004).
Webb, M. S. et al., "Antibacterial Efficacy against an In Vivo *Salmonella typhimurium* Infection Model and Pharmacokinetics of a Liposomal Ciprofloxacin Formulation," Antimicrobial Agents and Chemotherapy, 42(1):45-52 (Jan. 1998).
Yim, D. et al., "The Development of Inhaled Liposome-Encapsulated Ciprofloxacin to Treat Cystic Fibrosis," Respiratory Drug Delivery, pp. 425-428 (2006).

* cited by examiner

SYSTEMS FOR TREATING PULMONARY INFECTIONS

CROSS REFERENCE TO RELATED APPLICATIONS

This application claims the benefit of priority from U.S. Provisional Application No. 61/649,830, filed May 21, 2012, hereby incorporated by reference in its entirety.

BACKGROUND OF THE INVENTION

Certain technologies suitable for administration by inhalation employ liposomes and lipid complexes supply a prolonged therapeutic effect of drug in the lung. These technologies also provide the drug with sustained activities, and the ability to target and enhance the uptake of the drug into sites of disease.

Inhalation delivery of liposomes is complicated by their sensitivity to shear-induced stress during nebulization, which can lead to change in physical characteristics (e.g., entrapment, size). However, as long as the changes in characteristics are reproducible and meet acceptability criteria, they need not be prohibitive to pharmaceutical development.

Cystic fibrosis (CF) patients have thick mucus and/or sputum secretions in the lungs, frequent consequential infections, and biofilms resulting from bacterial colonizations. All these fluids and materials create barriers to effectively targeting infections with aminoglycosides. Liposomal aminoglycoside formulations may be useful in combating the bacterial biofilms.

SUMMARY OF THE INVENTION

The present invention provides methods for treating various pulmonary infections, including mycobacterial infections (e.g., pulmonary infections caused by nontuberculous mycobacterium, also referred to herein as nontuberculous mycobacterial (NTM) infections), by providing systems for delivery of aerosolized liposomal formulations via inhalation. For example, the systems and methods provided herein can be used to treat a pulmonary nontuberculous mycobacterial infection such as pulmonary M. avium, M. avium subsp. hominissuis (MAH), M. abscessus, M. chelonae, M. bolletii, M. kansasii, M. ulcerans, M. avium, M. avium complex (MAC) (M. avium and M. intracellulare), M. conspicuum, M. kansasii, M. peregrinum, M. immunogenum, M. xenopi, M. marinum, M. malmoense, M. marinum, M. mucogenicum, M. nonchromogenicum, M. scrofulaceum, M. simiae, M. smegmatis, M. szulgai, M. terrae, M. terrae complex, M. haemophilum, M. genavense, M. gordonae, M. ulcerans, M. fortuitum or M. fortuitum complex (M. fortuitum and M. chelonae) infection.

In one aspect, the present invention provides a system for treating or providing prophylaxis against a pulmonary infection. In one embodiment, the system comprises a pharmaceutical formulation comprising a liposomal complexed aminoglycoside, wherein the formulation is a dispersion (e.g., a liposomal solution or suspension), the lipid component of the liposome consists of electrically neutral lipids, and a nebulizer which generates an aerosol of the pharmaceutical formulation at a rate greater than about 0.53 g per minute. In one embodiment, the mass median aerodynamic diameter (MMAD) of the aerosol is less than about 4.2 µm, as measured by the Anderson Cascade Impactor (ACI), about 3.2 µm to about 4.2 µm, as measured by the ACI, or less than about 4.9 µm, as measured by the Next Generation Impactor (NGI), or about 4.4 µm to about 4.9 µm, as measured by the NGI.

In another embodiment, the system for treating or providing prophylaxis against a pulmonary infection comprises a pharmaceutical formulation comprising a liposomal complexed aminoglycoside, wherein the formulation is a dispersion (e.g., a liposomal solution or suspension), the lipid component of the liposome consists of electrically neutral lipids, and a nebulizer which generates an aerosol of the pharmaceutical formulation at a rate greater than about 0.53 g per minute. The fine particle fraction (FPF) of the aerosol is greater than or equal to about 64%, as measured by the Anderson Cascade Impactor (ACI), or greater than or equal to about 51%, as measured by the Next Generation Impactor (NGI).

In one embodiment, the system provided herein comprises a pharmaceutical formulation comprising an aminoglycoside. In a further embodiment, the aminoglycoside is amikacin, apramycin, arbekacin, astromicin, capreomycin, dibekacin, framycetin, gentamicin, hygromycin B, isepamicin, kanamycin, neomycin, netilmicin, paromomycin, rhodestreptomycin, ribostamycin, sisomicin, spectinomycin, streptomycin, tobramycin, verdamicin or a combination thereof. In even a further embodiment, the aminoglycoside is amikacin. In another embodiment, the aminoglycoside is selected from an aminoglycoside set forth in Table A, below, or a combination thereof

TABLE A

| AC4437 | dibekacin | K-4619 | sisomicin |
|---|---|---|---|
| amikacin | dactimicin | isepamicin | rhodestreptomycin |
| apramycin | etimicin | KA-5685 | sorbistin |
| arbekacin | framycetin | kanamycin | spectinomycin |
| astromicin | gentamicin | neomycin | sporaricin |
| bekanamycin | H107 | netilmicin | streptomycin |
| boholmycin | hygromycin | paromomycin | tobramycin |
| brulamycin | hygromycin B | plazomicin | verdamicin |
| capreomycin | inosamycin | ribostamycin | vertilmicin |

The pharmaceutical formulations provided herein are dispersions of liposomes (i.e., liposomal dispersions or aqueous liposomal dispersions which can be either liposomal solutions or liposomal suspensions). In one embodiment, the lipid component of the liposomes consists essentially of one or more electrically neutral lipids. In a further embodiment, the electrically neutral lipid comprises a phospholipid and a sterol. In a further embodiment, the phospholipid is dipalmitoylphosphatidylcholine (DPPC) and the sterol is cholesterol.

In one embodiment, the lipid to drug ratio in the aminoglycoside pharmaceutical formulation (aminoglycoside liposomal solution or suspension) is about 2:1, about 2:1 or less, about 1:1, about 1:1 or less, or about 0.7:1.

In one embodiment, the aerosolized aminoglycoside formulation, upon nebulization, has an aerosol droplet size of about 1 µm to about 3.8 µm, about 1.0 µm to about 4.8 µm, about 3.8 µm to about 4.8 µm, or about 4.0 µm to about 4.5 µm. In a further embodiment, the aminoglycoside is amikacin. In even a further embodiment, the amikacin is amikacin sulfate.

In one embodiment, about 70% to about 100% of the aminoglycoside present in the formulation is liposomal complexed, e.g., encapsulated in a plurality of liposomes, prior to nebulization. In a further embodiment, the aminoglycoside is selected from an aminoglycoside provided in Table A. In further embodiment, the aminoglycoside is an amikacin. In even a further embodiment, about 80% to about 100% of the amikacin is liposomal complexed, or about 80% to about 100% of the amikacin is encapsulated in a plurality of liposomes. In another embodiment, prior to nebulization, about 80% to about 100%, about 80% to about 99%, about 90% to about 100%, 90% to about 99%, or about 95% to about 99% of the aminoglycoside present in the formulation is liposomal complexed prior to nebulization.

In one embodiment, the percent liposomal complexed (also referred to herein as "liposomal associated") aminoglycoside post-nebulization is from about 50% to about 80%, from about 50% to about 75%, from about 50% to about 70%, from about 55% to about 75%, or from about 60% to about 70%. In a further embodiment, the aminoglycoside is selected from an aminoglycoside provided in Table A. In a further embodiment, the aminoglycoside is amikacin. In even a further embodiment, the amikacin is amikacin sulfate.

In another aspect, the present invention provides methods for treating or providing prophylaxis against a pulmonary infection. In one embodiment, the pulmonary infection is a pulmonary infection caused by a gram negative bacterium (also referred to herein as a gram negative bacterial infection). In one embodiment, the pulmonary infection is a *Pseudomonas* infection, e.g., a *Pseudomonas aeruginosa* infection. In another embodiment, the pulmonary infection is caused by one of the *Pseudomonas* species provided in Table B, below. In one embodiment, a patient is treated for mycobacterial lung infection with one of the systems provided herein. In a further embodiment, the mycobacterial pulmonary infection is a nontuberculous mycobacterial pulmonary infection, a *Mycobacterium abscessus* pulmonary infection or a *Mycobacterium avium* complex pulmonary infection. In one or more of the preceding embodiments, the patient is a cystic fibrosis patient.

In one embodiment, a patient with cystic fibrosis is treated for a pulmonary infection with one of the systems provided herein. In a further embodiment, the pulmonary infection is caused by *Mycobacterium abscessus, Mycobacterium avium* complex, or *P. aeruginosa*. In another embodiment, the pulmonary infection is caused by a nontuberculous *mycobacterium* selected from *M. avium, M. avium* subsp. *hominissuis* (MAH), *M. abscessus, M. chelonae, M. bolletii, M. kansasii, M. ulcerans, M. avium, M. avium* complex (MAC) (*M. avium* and *M. intracellulare*), *M. conspicuum, M. kansasii, M. peregrinum, M. immunogenum, M. xenopi, M. marinum, M. malmoense, M. marinum, M. mucogenicum, M. nonchromogenicum, M. scrofulaceum, M. simiae, M. smegmatis, M. szulgai, M. terrae, M. terrae* complex, *M. haemophilum, M. genavense, M. asiaticum, M. shimoidei, M. gordonae, M. nonchromogenicum, M. triplex, M. lentiflavum, M. celatum, M. fortuitum, M. fortuitum* complex (*M. fortuitum* and *M. chelonae*) or a combination thereof.

In another aspect, a method for treating or providing prophylaxis against a pulmonary infection in a patient is provided. In one embodiment, the method comprises aerosolizing a pharmaceutical formulation comprising a liposomal complexed aminoglycoside, wherein the pharmaceutical formulation is an aqueous dispersion of liposomes (e.g., a liposomal solution or liposomal suspension), and is aerosolized at a rate greater than about 0.53 gram per minute. The method further comprises administering the aerosolized pharmaceutical formulation to the lungs of the patient; wherein the aerosolized pharmaceutical formulation comprises a mixture of free aminoglycoside and liposomal complexed aminoglycoside, and the lipid component of the liposome consists of electrically neutral lipids. In a further embodiment, the mass median aerodynamic diameter (MMAD) of the aerosol is about 1.0 µm to about 4.2 µm as measured by the ACI. In any one of the proceeding embodiments, the MMAD of the aerosol is about 3.2 µm to about 4.2 µm as measured by the ACI. In any one of the proceeding embodiments, the MMAD of the aerosol is about 1.0 µm to about 4.9 µm as measured by the NGI. In any one of the proceeding embodiments, the MMAD of the aerosol is about 4.4 µm to about 4.9 µm as measured by the NGI.

In one embodiment, the method comprises aerosolizing a pharmaceutical formulation comprising a liposomal complexed aminoglycoside, wherein the pharmaceutical formulation is an aqueous dispersion and is aerosolized at a rate greater than about 0.53 gram per minute. The method further comprises administering the aerosolized pharmaceutical formulation to the lungs of the patient; wherein the aerosolized pharmaceutical formulation comprises a mixture of free aminoglycoside and liposomal complexed aminoglycoside (e.g., aminoglycoside encapsulated in a liposome), and the liposome component of the formulation consists of electrically neutral lipids. In even a further embodiment, fine particle fraction (FPF) of the aerosol is greater than or equal to about 64%, as measured by the ACI, or greater than or equal to about 51%, as measured by the NGI.

In another aspect, a liposomal complexed aminoglycoside aerosol (e.g., a liposomal complexed aminoglycoside) is provided. In one embodiment, the aerosol comprises an aminoglycoside and a plurality of liposomes comprising DPPC and cholesterol, wherein about 65% to about 75% of the aminoglycoside is liposomal complexed and the aerosol is generated at a rate greater than about 0.53 gram per minute. In a further embodiment, about 65% to about 75% of the aminoglycoside is liposomal complexed, and the aerosol is generated at a rate greater than about 0.53 gram per minute. In any one of the proceeding embodiments, the aerosol is generated at a rate greater than about 0.54 gram per minute. In any one of the proceeding embodiments, the aerosol is generated at a rate greater than about 0.55 gram per minute. In any one of the preceding embodiments, the aminoglycoside is selected from an aminoglycoside provided in Table A.

In one embodiment, the MMAD of the liposomal complexed aminoglycoside aerosol is about 3.2 µm to about 4.2 µm, as measured by the ACI, or about 4.4 µm to about 4.9 µm, as measured by the NGI. In a further embodiment, the aerosol comprises an aminoglycoside and a plurality of liposomes comprising DPPC and cholesterol, wherein about 65% to about 75% of the aminoglycoside is liposomal complexed (e.g., encapsulated in the plurality of the liposomes), and the liposomal aminoglycoside aerosol is generated at a rate greater than about 0.53 gram per minute. In a further embodiment, the aminoglycoside is selected from an aminoglycoside provided in Table A.

In one embodiment, the FPF of the lipid-complexed aminoglycoside aerosol is greater than or equal to about 64%, as measured by the Anderson Cascade Impactor (ACI), or greater than or equal to about 51%, as measured by the Next Generation Impactor (NGI). In a further embodiment, the aerosol comprises an aminoglycoside and a plurality of liposomes comprising DPPC and cholesterol, wherein about 65% to about 75% of the aminoglycoside is liposomal complexed, for example, encapsulated in the plurality of the liposomes, and the liposomal aminoglycoside aerosol is generated at a rate greater than about 0.53 gram per minute. In any one of the proceeding embodiments, the aerosol is generated at a rate greater than about 0.54 gram per minute. In any one of the proceeding embodiments, the aerosol is generated at a rate or greater than about 0.55 gram per minute. In any of the preceding embodiments, the aminoglycoside is selected from an aminoglycoside provided in Table A.

In one embodiment, the aerosol comprises an aminoglycoside and a plurality of liposomes comprising DPPC and cholesterol, wherein about 65% to about 75% of the aminoglycoside is liposomal complexed. In a further embodiment, about 65% to about 75% of the aminoglycoside is encapsulated in the plurality of liposomes. In a further embodiment, the aerosol is generated at a rate greater than about 0.53 gram per minute, greater than about 0.54 gram per minute, or greater than about 0.55 gram per minute. In a further embodiment, the aminoglycoside is amikacin (e.g., amikacin sulfate).

In one embodiment, the concentration of the aminoglycoside in the liposomal complexed aminoglycoside is about 50 mg/mL or greater. In a further embodiment, the concentration of the aminoglycoside in the liposomal complexed aminoglycoside is about 60 mg/mL or greater. In a further embodiment, the concentration of the aminoglycoside in the liposomal complexed aminoglycoside is about 70 mg/mL or greater, for example about 70 mg/mL to about 75 mg/mL. In a further embodiment, the aminoglycoside is selected from an aminoglycoside provided in Table A. In even a further embodiment, the aminoglycoside is amikacin (e.g., amikacin sulfate).

DETAILED DESCRIPTION OF THE INVENTION

Figure 1:
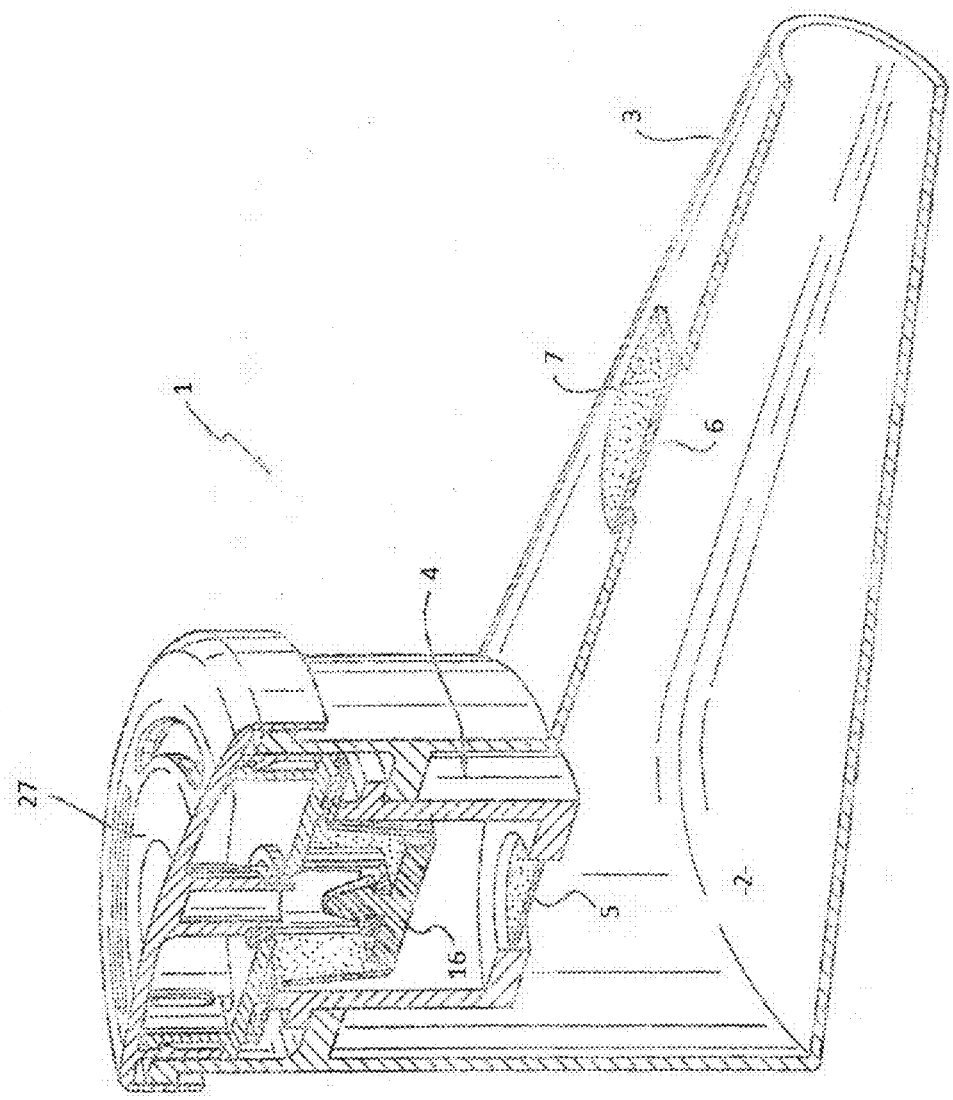
FIG. 1 shows a diagram of a nebulizer (aerosol generator) in which the present invention may be implemented.

The invention described herein is directed, in part, to systems for administering an aminoglycoside pharmaceutical formulation to the lungs of a subject, for example, to treat a pulmonary disorder.

The term "treating" includes: (1) preventing or delaying the appearance of clinical symptoms of the state, disorder or condition developing in the subject that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a subject to be treated is either statistically significant or at least perceptible to the subject or to the physician.

In one embodiment, pulmonary infections caused by the following bacteria are treatable with the systems and formulations provided herein: *Pseudomonas* (e.g., *P. aeruginosa, P. paucimobilis, P. putida, P. fluorescens*, and *P. acidovorans*), *Burkholderia* (e.g., *B. pseudomallei, B. cepacia, B. cepacia complex, B. dolosa, B. fungorum, B. gladioli, B. multivorans, B. vietnamiensis, B. pseudomallei, B. ambifaria, B. andropogonis, B. anthina, B. brasilensis, B. calcdonica, B. caribensis, B. caryophylli*), *Staphylococcus* (e.g., *S. aureus, S. auricularis, S. carnosus, S. epidermidis, S. lugdunensis*), Methicillin-resistant *Staphylococcus aureus* (MRSA), *Streptococcus* (e.g., *Streptococcus pneumoniae*), *Escherichia coli, Klebsiella, Enterobacter, Serratia, Haemophilus, Yersinia pestis, Mycobacterium* (e.g., nontuberculous *mycobacterium*).

In one embodiment, a patient is treated for a nontuberculous mycobacterial lung infection with one of the systems provided herein. In a further embodiment, the nontuberculous mycobacterial lung infection is a recalcitrant nontuberculous mycobacterial lung infection.

In one embodiment, the systems provided herein are used to treat a patient having a pulmonary infection caused by *Pseudomonas*. In a further embodiment, the pulmonary infection is caused by a *Pseudomonas* species selected from a species provided in Table B, below.

TABLE B

| P. abietaniphila | P. aeruginosa | P. agarici | P. alcaligenes | P. alcaliphila | P. amygdale |
| P. anguilliseptica | P. antarctica | P. argentinensis | P. asplenii | P. aurantiaca | P. aureofaciens |
| P. avellanae | P. azotifigens | P. azotoformans | P. balearica | P. borbori | P. brassicacearum |

TABLE B-continued

| | | | | | |
|---|---|---|---|---|---|
| P. brenneri | P. cannabina | P. caricapapayae | P. cedrina | P. chlororaphis | P. cichorii |
| P. citronellolis | P. coenobios | P. congelans | P. coronofaciens | P. corrugate | P. costantinii |
| P. cremoricolorata | P. cruciviae | P. delhiensis | P. denitrificans | P. excibis | P. extremorientalis |
| P. ficuseructae | P. flavescens | P. fluorescens | P. fragi | P. frederiksbergensis | P. fulva |
| P. fuscovaginae | P. gelidicola | P. gessardii | P. grimontii | P. indica | P. jessenii |
| P. jinjuensis | P. kilonensis | P. knackmussii | P. koreensis | P. libanensis | P. lini |
| P. lundensis | P. lutea | P. luteola | P. mandelii | P. marginalis | P. mediterranea |
| P. meliae | P. mendocina | P. meridiana | P. migulae | P. monteilii | P. moraviensis |
| P. mosselii | P. mucidolens | P. nitroreducens | P. oleovorans | P. orientalis | P. oryzihabitans |
| P. otitidis | P. pachastrellae | P. palleroniana | P. panacis | P. papaveris | P. parafulva |
| P. peli | P. perolens | P. pertucinogena | P. plecoglossicida | P. poae | P. pohangensis |
| P. proteolytica | P. pseudoakaligenes | P. psychrophila | P. psychrotolerans | P. putida | P. rathonis |
| P. reptilivora | P. resiniphila | P. resinovorans | P. rhizosphaerae | P. rhodesiae | P. rubescens |
| P. salomonii | P. savastanoi | P. segitis | P. septic | P. simiae | P. straminea |
| P. stutzeri | P. suis | P. synxantha | P. syringae | P. taetrolens | P. thermotolerans |
| P. thivervalensis | P. tolaasii | P. tremae | P. trivialis | P. turbinellae | P. tuticorinensis |
| P. umsongensis | P. vancouverensis | P. veronii | P. viridiflava | P. vranovensis | P. xanthomarina |

The nontuberculous mycobacterial lung infection, in one embodiment, is selected from *M. avium*, *M. avium* subsp. *hominissuis* (MAH), *M. abscessus*, *M. chelonae*, *M. bolletii*, *M. kansasii*, *M. ulcerans*, *M. avium*, *M. avium* complex (MAC) (*M. avium* and *M. intracellulare*), *M. conspicuum*, *M. kansasii*, *M. peregrinum*, *M. immunogenum*, *M. xenopi*, *M. marinum*, *M. malmoense*, *M. marinum*, *M. mucogenicum*, *M. nonchromogenicum*, *M. scrofulaceum*, *M. simiae*, *M. smegmatis*, *M. szulgai*, *M. terrae*, *M. terrae* complex, *M. haemophilum*, *M. genavense*, *M. asiaticum*, *M. shimoidei*, *M. gordonae*, *M. nonchromogenicum*, *M. triplex*, *M. lentiflavum*, *M. celatum*, *M. fortuitum*, *M. fortuitum* complex (*M. fortuitum* and *M. chelonae*) or a combination thereof. In a further embodiment, the nontuberculous mycobacterial lung infection is *M. abscessus* or *M. avium*. In a further embodiment, the *M. avium* infection is *M. avium* subsp. *hominissuis*. In one embodiment, the nontuberculous mycobacterial lung infection is a recalcitrant nontuberculous mycobacterial lung infection.

In another embodiment, a cystic fibrosis patient is treated for a bacterial infection with one of the systems provided herein. In a further embodiment, the bacterial infection is a lung infection due to *Pseudomonas aeruginosa*. In yet another embodiment, a patient is treated for a pulmonary infection associated with bronchiectasis with one of the systems provided herein.

"Prophylaxis," as used herein, can mean complete prevention of an infection or disease, or prevention of the development of symptoms of that infection or disease; a delay in the onset of an infection or disease or its symptoms; or a decrease in the severity of a subsequently developed infection or disease or its symptoms.

The term "antibacterial" is art-recognized and refers to the ability of the compounds of the present invention to prevent, inhibit or destroy the growth of microbes of bacteria. Examples of bacteria are provided above.

The term "antimicrobial" is art-recognized and refers to the ability of the aminoglycoside compounds of the present invention to prevent, inhibit, delay or destroy the growth of microbes such as bacteria, fungi, protozoa and viruses.

"Effective amount" means an amount of an aminoglycoside (e.g., amikacin) used in the present invention sufficient to result in the desired therapeutic response. The effective amount of the formulation provided herein comprises both free and liposomal complexed aminoglycoside. For example, the liposomal complexed aminoglycoside, in one embodiment, comprises aminoglycoside encapsulated in a liposome, or complexed with a liposome, or a combination thereof.

In one embodiment, the aminoglycoside is selected from amikacin, apramycin, arbekacin, astromicin, capreomycin, dibekacin, framycetin, gentamicin, hygromycin B, isepamicin, kanamycin, neomycin, netilmicin, paromomycin, rhodestreptomycin, ribostamycin, sisomicin, spectinomycin, streptomycin, tobramycin or verdamicin. In another embodiment, the aminoglycoside is selected from an aminoglycoside set forth in Table C, below.

TABLE C

| | | | |
|---|---|---|---|
| AC4437 | dibekacin | K-4619 | sisomicin |
| amikacin | dactimicin | isepamicin | rhodestreptomycin |
| arbekacin | etimicin | KA-5685 | sorbistin |
| apramycin | framycetin | kanamycin | spectinomycin |
| astromicin | gentamicin | neomycin | sporaricin |
| bekanamycin | H107 | netilmicin | streptomycin |
| boholmycin | hygromycin | paromomycin | tobramycin |
| brulamycin | hygromycin B | plazomicin | verdamicin |
| capreomycin | inosamycin | ribostamycin | vertilmicin |

In one embodiment, the aminoglycoside is an aminoglycoside free base, or its salt, solvate, or other non-covalent derivative. In a further embodiment, the aminoglycoside is amikacin. Included as suitable aminoglycosides used in the drug formulations of the present invention are pharmaceutically acceptable addition salts and complexes of drugs. In cases where the compounds may have one or more chiral centers, unless specified, the present invention comprises each unique racemic compound, as well as each unique nonracemic compound. In cases in which the active agents have unsaturated carbon-carbon double bonds, both the cis (Z) and trans (E) isomers are within the scope of this invention. In cases where the active agents exist in tautomeric forms, such as keto-enol tautomers, each tautomeric form is contemplated as being included within the invention. Amikacin, in one embodiment, is present in the pharmaceutical formulation as amikacin base, or amikacin salt, for example, amikacin sulfate or amikacin disulfate. In one embodiment, a combination of one or more of the above aminoglycosides is used in the formulations, systems and methods described herein. In a further embodiment, the combination comprises amikacin.

The therapeutic response can be any response that a user (e.g., a clinician) will recognize as an effective response to the therapy. The therapeutic response will generally be a reduction, inhibition, delay or prevention in growth of or reproduction of one or more bacterium, or the killing of one or more bacterium, as described above. A therapeutic response may also be reflected in an improvement in pulmonary function, for example forced expiratory volume in one second ($FEV_1$). It is further within the skill of one of ordinary skill in the art to determine appropriate treatment duration, appropriate doses, and any potential combination treatments, based upon an evaluation of therapeutic response.

"Liposomal dispersion" refers to a solution or suspension comprising a plurality of liposomes.

An "aerosol", as used herein, is a gaseous suspension of liquid particles. The aerosol provided herein comprises particles of the liposomal dispersion.

A "nebulizer" or an "aerosol generator" is a device that converts a liquid into an aerosol of a size that can be inhaled into the respiratory tract. Pneumonic, ultrasonic, electronic nebulizers, e.g., passive electronic mesh nebulizers, active electronic mesh nebulizers and vibrating mesh nebulizers are amenable for use with the invention if the particular nebulizer emits an aerosol with the required properties, and at the required output rate.

The process of pneumatically converting a bulk liquid into small droplets is called atomization. The operation of a pneumatic nebulizer requires a pressurized gas supply as the driving force for liquid atomization. Ultrasonic nebulizers use electricity introduced by a piezoelectric element in the liquid reservoir to convert a liquid into respirable droplets. Various types of nebulizers are described in Respiratory Care, Vol. 45, No. 6, pp. 609-622 (2000), the disclosure of which is incorporated herein by reference in its entirety. The terms "nebulizer" and "aerosol generator" are used interchangeably throughout the specification. "Inhalation device", "inhalation system" and "atomizer" are also used in the literature interchangeably with the terms "nebulizer" and "aerosol generator".

"Fine particle fraction" or "FPF", as used herein, refers to the fraction of the aerosol having a particle size less than 5 μm in diameter, as measured by cascade impaction. FPF is usually expressed as a percentage.

"Mass median diameter" or "MMD" is determined by laser diffraction or impactor measurements, and is the average particle diameter by mass.

"Mass median aerodynamic diameter" or "MMAD" is normalized regarding the aerodynamic separation of aqua aerosol droplets and is determined impactor measurements, e.g., the Anderson Cascade Impactor (ACI) or the Next Generation Impactor (NGI). The gas flow rate, in one embodiment, is 28 Liter per minute by the Anderson Cascade Impactor (ACI) and 15 Liter per minute by the Next Generation Impactor (NGI). "Geometric standard deviation" or "GSD" is a measure of the spread of an aerodynamic particle size distribution.

In one embodiment, the present invention provides a system for treating a pulmonary infection or providing prophylaxis against a pulmonary infection. Treatment is achieved via delivery of the aminoglycoside formulation by inhalation via nebulization. In one embodiment, the pharmaceutical formulation comprises an aminoglycoside agent, e.g., an aminoglycoside.

The pharmaceutical formulation, as provided herein, is a liposomal dispersion. Specifically, the pharmaceutical formulation is a dispersion comprising a "liposomal complexed aminoglycoside" or an "aminoglycoside encapsulated in a liposome". A "liposomal complexed aminoglycoside" includes embodiments where the aminoglycoside (or combination of aminoglycosides) is encapsulated in a liposome, and includes any form of aminoglycoside composition where at least about 1% by weight of the aminoglycoside is associated with the liposome either as part of a complex with a liposome, or as a liposome where the aminoglycoside may be in the aqueous phase or the hydrophobic bilayer phase or at the interfacial headgroup region of the liposomal bilayer.

In one embodiment, the lipid component of the liposome comprises electrically neutral lipids, positively charged lipids, negatively charged lipids, or a combination thereof. In another embodiment, the lipid component comprises electrically neutral lipids. In a further embodiment, the lipid component consists essentially of electrically neutral lipids. In even a further embodiment, the lipid component consists of electrically neutral lipids, e.g., a sterol and a phospholipid.

As provided above, liposomal complexed aminoglycoside embodiments include embodiments where the aminoglycoside is encapsulated in a liposome. In addition, the liposomal complexed aminoglycoside describes any composition, solution or suspension where at least about 1% by weight of the aminoglycoside is associated with the lipid either as part of a complex with the liposome, or as a liposome where the aminoglycoside may be in the aqueous phase or the hydrophobic bilayer phase or at the interfacial headgroup region of the liposomal bilayer. In one embodiment, prior to nebulization, at least about 5%, at least about 10%, at least about 20%, at least about 25%, at least about 50%, at least about 75%, at least about 80%, at least about 85%, at least about 90% or at least about 95% of the aminoglycoside in the formulation is so associated. Association, in one embodiment, is measured by separation through a filter where lipid and lipid-associated drug is retained (i.e., in the retentate) and free drug is in the filtrate.

The formulations, systems and methods provided herein comprise a lipid-encapsulated or lipid-associated aminoglycoside agent. The lipids used in the pharmaceutical formulations of the present invention can be synthetic, semi-synthetic or naturally-occurring lipids, including phospholipids, tocopherols, sterols, fatty acids, negatively-charged lipids and cationic lipids.

In one embodiment, at least one phospholipid is present in the pharmaceutical formulation. In one embodiment, the phospholipid is selected from: phosphatidylcholine (EPC), phosphatidylglycerol (PG), phosphatidylinositol (PI), phosphatidylserine (PS), phosphatidylethanolamine (PE), and phosphatidic acid (PA); the soya counterparts, soy phosphatidylcholine (SPC); SPG, SPS, SPI, SPE, and SPA; the hydrogenated egg and soya counterparts (e.g., HEPC, HSPC), phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The carbon chains on these fatty acids can be saturated or unsaturated, and the phospholipid may be made up of fatty acids of different chain lengths and different degrees of unsaturation.

In one embodiment, the pharmaceutical formulation includes dipalmitoylphosphatidylcholine (DPPC), a major constituent of naturally-occurring lung surfactant. In one embodiment, the lipid component of the pharmaceutical formulation comprises DPPC and cholesterol, or consists essentially of DPPC and cholesterol, or consists of DPPC and cholesterol. In a further embodiment, the DPPC and cholesterol have a mole ratio in the range of from about 19:1 to about 1:1, or about 9:1 to about 1:1, or about 4:1 to about 1:1, or about 2:1 to about 1:1, or about 1.86:1 to about 1:1. In even a further embodiment, the DPPC and cholesterol have a mole ratio of about 2:1 or about 1:1. In one embodiment, DPPC and cholesterol are provided in an aminoglycoside formulation, e.g., an aminoglycoside formulation.

Other examples of lipids for use with the invention include, but are not limited to, dimyristoylphosphatidycholine (DMPC), dimyristoylphosphatidylglycerol (DMPG), dipalmitoylphosphatidcholine (DPPC), dipalmitoylphosphatidylglycerol (DPPG), distearoylphosphatidylcholine (DSPC), distearoylphosphatidylglycerol (DSPG), dioleylphosphatidyl-ethanolamine (DOPE), mixed phospholipids such as palmitoylstearoylphosphatidyl-choline (PSPC), and single acylated phospholipids, for example, mono-oleoyl-phosphatidylethanolamine (MOPE).

In one embodiment, the at least one lipid component comprises a sterol. In a further embodiment, the at least one lipid component comprises a sterol and a phospholipid, or consists essentially of a sterol and a phospholipid, or consists of a sterol and a phospholipid. Sterols for use with the invention include, but are not limited to, cholesterol, esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate, lanosterol sulfate and tocopherols. The tocopherols can include tocopherols, esters of tocopherols including tocopherol hemi-succinates, salts of tocopherols including tocopherol hydrogen sulfates and tocopherol sulfates. The term "sterol compound" includes sterols, tocopherols and the like.

In one embodiment, at least one cationic lipid (positively charged lipid) is provided in the systems described herein. The cationic lipids used can include ammonium salts of fatty acids, phospholids and glycerides. The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA) and 1,2-bis(oleoyloxy)-3-(trimethylammonio) propane (DOTAP).

In one embodiment, at least one anionic lipid (negatively charged lipid) is provided in the systems described herein. The negatively-charged lipids which can be used include phosphatidyl-glycerols (PGs), phosphatidic acids (PAs), phosphatidylinositols (PIs) and the phosphatidyl serines (PSs). Examples include DMPG, DPPG, DSPG, DMPA, DPPA, DSPA, DMPI, DPPI, DSPI, DMPS, DPPS and DSPS.

Without wishing to be bound by theory, phosphatidylcholines, such as DPPC, aid in the uptake of the aminoglycoside agent by the cells in the lung (e.g., the alveolar macrophages) and helps to maintain the aminoglycoside agent in the lung. The negatively charged lipids such as the PGs, PAs, PSs and PIs, in addition to reducing particle aggregation, are thought to play a role in the sustained activity characteristics of the inhalation formulation as well as in the transport of the formulation across the lung (transcytosis) for systemic uptake. The sterol compounds, without wishing to be bound by theory, are thought to affect the release characteristics of the formulation.

Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer) or a combination thereof. The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase.

Liposomes can be produced by a variety of methods (see, e.g., Cullis et al. (1987)). In one embodiment, one or more of the methods described in U.S. Patent Application Publication No. 2008/0089927 are used herein to produce the aminoglycoside encapsulated lipid formulations (liposomal dispersion). The disclosure of U.S. Patent Application Publication No. 2008/0089927 is incorporated by reference in its entirety for all purposes. For example, in one embodiment, at least one lipid and an aminoglycoside are mixed with a coacervate (i.e., a separate liquid phase) to form the liposome formulation. The coacervate can be formed to prior to mixing with the lipid, during mixing with the lipid or after mixing with the lipid. Additionally, the coacervate can be a coacervate of the active agent.

In one embodiment, the liposomal dispersion is formed by dissolving one or more lipids in an organic solvent forming a lipid solution, and the aminoglycoside coacervate forms from mixing an aqueous solution of the aminoglycoside with the lipid solution. In a further embodiment, the organic solvent is ethanol. In even a further embodiment, the one or more lipids comprise a phospholipid and a sterol.

In one embodiment, liposomes are produces by sonication, extrusion, homogenization, swelling, electroformation, inverted emulsion or a reverse evaporation method. Bangham's procedure (J. Mol. Biol. (1965)) produces ordinary multilamellar vesicles (MLVs). Lenk et al. (U.S. Pat. Nos. 4,522,803, 5,030,453 and 5,169,637), Fountain et al. (U.S. Pat. No. 4,588,578) and Cullis et al. (U.S. Pat. No. 4,975,282) disclose methods for producing multilamellar liposomes having substantially equal interlamellar solute distribution in each of their aqueous compartments. Paphadjopoulos et al., U.S. Pat. No. 4,235,871, discloses preparation of oligolamellar liposomes by reverse phase evaporation. Each of the methods is amenable for use with the present invention.

Unilamellar vesicles can be produced from MLVs by a number of techniques, for example, the extrusion techniques of U.S. Pat. No. 5,008,050 and U.S. Pat. No. 5,059,421. Sonication and homogenization cab be so used to produce smaller unilamellar liposomes from larger liposomes (see, for example, Paphadjopoulos et al. (1968); Deamer and Uster (1983); and Chapman et al. (1968)).

The liposome preparation of Bangham et al. (J. Mol. Biol. 13, 1965, pp. 238-252) involves suspending phospholipids in an organic solvent which is then evaporated to dryness leaving a phospholipid film on the reaction vessel. Next, an appropriate amount of aqueous phase is added, the 60 mixture is allowed to "swell", and the resulting liposomes which consist of multilamellar vesicles (MLVs) are dispersed by mechanical means. This preparation provides the basis for the development of the small sonicated unilamellar vesicles described by Papahadjopoulos et al. (Biochim. Biophys. Acta. 135, 1967, pp. 624-638), and large unilamellar vesicles.

Techniques for producing large unilamellar vesicles (LUVs), such as, reverse phase evaporation, infusion procedures, and detergent dilution, can be used to produce liposomes for use in the pharmaceutical formulations provided herein. A review of these and other methods for producing liposomes may be found in the text Liposomes, Marc Ostro, ed., Marcel Dekker, Inc., New York, 1983, Chapter 1, which is incorporated herein by reference. See also Szoka, Jr. et al., (Ann. Rev. Biophys. Bioeng. 9, 1980, p. 467), which is also incorporated herein by reference in its entirety for all purposes.

Other techniques for making liposomes include those that form reverse-phase evaporation vesicles (REV), U.S. Pat. No. 4,235,871. Another class of liposomes that may be used is characterized as having substantially equal lamellar solute distribution. This class of liposomes is denominated as stable plurilamellar vesicles (SPLV) as defined in U.S. Pat. No. 4,522,803, and includes monophasic vesicles as described in U.S. Pat. No. 4,588,578, and frozen and thawed multilamellar vesicles (FATMLV) as described above.

A variety of sterols and their water soluble derivatives such as cholesterol hemisuccinate have been used to form liposomes; see, e.g., U.S. Pat. No. 4,721,612. Mayhew et al., PCT Publication No. WO 85/00968, described a method for reducing the toxicity of drugs by encapsulating them in liposomes comprising alpha-tocopherol and certain derivatives thereof. Also, a variety of tocopherols and their water soluble derivatives have been used to form liposomes, see PCT Publication No. 87/02219.

The pharmaceutical formulation, in one embodiment, pre-nebulization, comprises liposomes with a mean diameter, that is measured by a light scattering method, of approximately 0.01 microns to approximately 3.0 microns, for example, in the range about 0.2 to about 1.0 microns. In one embodiment, the mean diameter of the liposomes in the formulation is about 200 nm to about 300 nm, about 210 nm to about 290 nm, about 220 nm to about 280 nm, about 230 nm to about 280 nm, about 240 nm to about 280 nm, about 250 nm to about 280 nm or about 260 nm to about 280 nm. The sustained activity profile of the liposomal product can be regulated by the nature of the lipid membrane and by inclusion of other excipients in the composition.

In order to minimize dose volume and reduce patient dosing time, in one embodiment, it is important that liposomal entrapment of the aminoglycoside (e.g., the aminoglycoside amikacin) be highly efficient and that the L/D ratio be at as low a value as possible and/or practical while keeping the liposomes small enough to penetrate patient mucus and biofilms, e.g., *Pseudomonas* biofilms. In one embodiment, the L/D ratio in liposomes provided herein is 0.7 or about 0.7 (w/w). In a further embodiment, the liposomes provided herein are small enough to effectively penetrate a bacterial biofilm (e.g., *Pseudomonas* biofilm). In even a further embodiment, the mean diameter of the liposomes, as measured by light scattering is about 260 to about 280 nm.

The lipid to drug ratio in the pharmaceutical formulations provided herein, in one embodiment, is 3 to 1 or less, 2.5 to 1 or less, 2 to 1 or less, 1.5 to 1 or less, or 1 to 1 or less. The lipid to drug ratio in the pharmaceutical formulations provided herein, in another embodiment, is less than 3 to 1, less than 2.5 to 1, less than 2 to 1, less than 1.5 to 1, or less than 1 to 1. In a further embodiment, the lipid to drug ratio is about 0.7 to or less or about 0.7 to 1. In one embodiment, one of the lipids or lipid combinations in Table 1, below, is used in the pharmaceutical formulation of the invention.

TABLE 1

Lipids amenable for use with the invention

| Lipid(s) | Mole ratio | Lipid/aminoglycoside (w/w) |
|---|---|---|
| DPPC | — | 1.1 |
| DPPC/DOPG | 9:1 | 1.0 |
| DPPC/DOPG | 7:1 | 3.9 |
| DPPC/DOPG | 1:1 | 2.8 |
| DPPC/DOPG | 0.5:1 | 2.7 |
| DOPG | — | 2.6 |
| DPPC/Cholesterol | about 1:1 | about 0.7 |
| DPPC/Cholesterol | 1:1 | 0.7 |
| DPPC/Cholesterol | 19:1 | 1.0 |
| DPPC/Cholesterol | 9:1 | 1.2 |
| DPPC/Cholesterol | 4:1 | 1.7 |
| DPPC/Cholesterol | 1.86:1 | 2.1 |
| DPPC/Cholesterol | 1:1 | 2.7 |
| DPPC/DOPC/Cholesterol | 8.55:1:0.45 | 2.0 |
| DPPC/DOPC/Cholesterol | 6.65:1:0.35 | 3.0 |
| DPPC/DOPC/Cholesterol | 19:20:1 | 2.5 |
| DPPC/DOPC/Cholesterol | 8.55:1:0.45 | 3.8 |
| DPPC/DOPC/Cholesterol | 6.65:1:0.35 | 4.1 |
| DPPC/DOPC/Cholesterol | 19:20:1 | 4.2 |
| DPPC/DOPC/DOPG/Cholesterol | 42:4:9:45 | 3.7 |
| DPPC/DOPC/DOPG/Cholesterol | 59:5:6:30 | 3.7 |

In one embodiment, the system provided herein comprises an aminoglycoside formulation, for example, an amikacin formulation, e.g., amikacin base formulation. In one embodiment, the amount of aminoglycoside provided in the system is about 450 mg, about 500 mg, about 550 mg, about 560 mg, about 570 mg, about 580 mg, about 590 mg, about 600 mg or about 610 mg. In another embodiment, the amount of aminoglycoside provided in the system is from about 500 mg to about 600 mg, or from about 500 mg to about 650 mg, or from about 525 mg to about 625 mg, or from about 550 mg to about 600 mg. In one embodiment, the amount of aminoglycoside administered to the subject is about 560 mg and is provided in an 8 mL formulation. In one embodiment, the amount of aminoglycoside administered to the subject is about 590 mg and is provided in an 8 mL formulation. In one embodiment, the amount of aminoglycoside administered to the subject is about 600 mg and is provided in an 8 mL formulation. In one embodiment, the aminoglycoside is amikacin and the amount of amikacin provided in the system is about 450 mg, about 500 mg, about 550 mg, about 560 mg, about 570 mg, about 580 mg, about 590 mg, about 600 mg or about 610 mg. In another embodiment, the aminoglycoside is amikacin and the amount of amikacin provided in the system is from about 500 mg to about 650 mg, or from about 525 mg to about 625 mg, or from about 550 mg to about 600 mg. In one embodiment, the aminoglycoside is amikacin and the amount of amikacin administered to the subject is about 560 mg, and is provided in an 8 mL formulation. In one embodiment, the aminoglycoside is amikacin and the amount of amikacin administered to the subject is about 590 mg, and is provided in an 8 mL formulation. In one embodiment, the aminoglycoside is amikacin and the amount of aminoglycoside administered to the subject is about 600 mg and is provided in an 8 mL formulation.

In one embodiment, the system provided herein comprises an aminoglycoside formulation, for example, an amikacin (base formulation). In one embodiment, the aminoglycoside formulation provided herein comprises about 60 mg/mL aminoglycoside, about 65 mg/mL aminoglycoside, about 70 mg/mL aminoglycoside, about 75 mg/mL aminoglycoside, about 80 mg/mL aminoglycoside, about 85 mg/mL aminoglycoside, or about 90 mg/mL aminoglycoside. In a further embodiment, the aminoglycoside is amikacin.

In one embodiment, the system provided herein comprises an about 8 mL liposomal amikacin formulation. In one embodiment, the density of the liposomal amikacin formulation is about 1.05 gram/mL; and in one embodiment, approximately 8.4 grams of the liposomal amikacin formulation per dose is present in the system of the invention. In a further embodiment, the entire volume of the formulation is administered to a subject in need thereof.

In one embodiment, the pharmaceutical formulation provided herein comprises at least one aminoglycoside, at least one phospholipid and a sterol. In a further embodiment, the pharmaceutical formulation comprises an aminoglycoside, DPPC and cholesterol. In one embodiment, the pharmaceutical formulation is the formulation provided in Table 2, below.

TABLE 2

Pharmaceutical Formulations

| Component | Concentration | Component | Concentration |
|---|---|---|---|
| Formulation A (pH 6.0-7.0) | | Formulation D (pH ~6.5) | |
| Aminoglycoside | 60-80 mg/mL | Aminoglycoside | ~70 mg/mL |
| Phospholipid | 30-40 mg/mL | Phospholipid | ~32-35 mg/mL |
| Sterol | 10-20 mg/mL | Sterol | ~16-17 mg/mL |
| Salt | 0.5%-5.0% | Salt | ~1.5% |
| Formulation B (pH 6.0-7.0) | | Formulation E (pH ~6.5) | |
| Amikacin | 60-80 mg/mL | Amikacin | ~70 mg/mL |
| DPPC | 30-40 mg/mL | DPPC | ~32-35 mg/mL |
| Cholesterol | 10-20 mg/mL | Cholesterol | ~16-17 mg/mL |
| NaCl | 0.5%-5.0% | NaCl | ~1.5% |
| Formulation C (pH 6.0-7.0) | | Formulation F (pH ~6.5) | |
| Amikacin | 70-80 mg/mL | Amikacin | ~70 mg/mL |
| DPPC | 35-40 mg/mL | DPPC | ~30-35 mg/mL |
| Cholesterol | 15-20 mg/mL | Cholesterol | ~15-17 mg/mL |
| NaCl | 0.5%-5.0% | NaCl | ~1.5% |

It should be noted that increasing aminoglycoside concentration alone may not result in a reduced dosing time. For example, in one embodiment, the lipid to drug ratio is fixed, and as amikacin concentration is increased (and therefore lipid concentration is increased, since the ratio of the two is fixed, for example at ~0.7:1), the viscosity of the solution also increases, which slows nebulization time.

In one embodiment, prior to nebulization of the aminoglycoside formulation, about 70% to about 100% of the aminoglycoside present in the formulation is liposomal complexed. In a further embodiment, the aminoglycoside is an aminoglycoside. In even a further embodiment, the aminoglycoside is amikacin. In another embodiment, prior to nebulization, about 80% to about 99%, or about 85% to about 99%, or about 90% to about 99% or about 95% to about 99% or about 96% to about 99% of the aminoglycoside present in the formulation is liposomal complexed. In a further embodiment, the aminoglycoside is amikacin or tobramycin. In even a further embodiment, the aminoglycoside is amikacin. In another embodiment, prior to nebulization, about 98% of the aminoglycoside present in the formulation is liposomal complexed. In a further embodiment, the aminoglycoside is amikacin or tobramycin. In even a further embodiment, the aminoglycoside is amikacin.

In one embodiment, upon nebulization, about 20% to about 50% of the liposomal complexed aminoglycoside agent is released, due to shear stress on the liposomes. In a further embodiment, the aminoglycoside agent is an amikacin. In another embodiment, upon nebulization, about 25% to about 45%, or about 30% to about 40% of the liposomal complexed aminoglycoside agent is released, due to shear stress on the liposomes. In a further embodiment, the aminoglycoside agent is amikacin.

As provided herein, the present invention provides methods and systems for treatment of lung infections by inhalation of a liposomal aminoglycoside formulation via nebulization. The formulation, in one embodiment, is administered via a nebulizer, which provides an aerosol mist of the formulation for delivery to the lungs of a subject.

In one embodiment, the nebulizer described herein generates an aerosol (i.e., achieves a total output rate) of the aminoglycoside pharmaceutical formulation at a rate greater than about 0.53 g per minute, greater than about 0.54 g per minute, greater than about 0.55 g per minute, greater than about 0.58 g per minute, greater than about 0.60 g per minute, greater than about 0.65 g per minute or greater than about 0.70 g per minute. In another embodiment, the nebulizer described herein generates an aerosol (i.e., achieves a total output rate) of the aminoglycoside pharmaceutical formulation at about 0.53 g per minute to about 0.80 g per minute, at about 0.53 g per minute to about 0.70 g per minute, about 0.55 g per min to about 0.70 g per minute, about 0.53 g per minute to about 0.65 g per minute, or about 0.60 g per minute to about 0.70 g per minute. In yet another embodiment, the nebulizer described herein generates an aerosol (i.e., achieves a total output rate) of the aminoglycoside pharmaceutical formulation at about 0.53 g per minute to about 0.75 g per minute, about 0.55 g per min to about 0.75 g per minute, about 0.53 g per minute to about 0.65 g per minute, or about 0.60 g per minute to about 0.75 g per minute.

Upon nebulization, the liposomes in the pharmaceutical formulation leak drug. In one embodiment, the amount of liposomal complexed aminoglycoside post-nebulization is about 45% to about 85%, or about 50% to about 80% or about 51% to about 77%. These percentages are also referred to herein as "percent associated aminoglycoside post-nebulization". As provided herein, in one embodiment, the liposomes comprise an aminoglycoside, e.g., amikacin. In one embodiment, the percent associated aminoglycoside post-nebulization is from about 60% to about 70%. In a further embodiment, the aminoglycoside is amikacin. In another embodiment, the percent associated aminoglycoside post-nebulization is about 67%, or about 65% to about 70%. In a further embodiment, the aminoglycoside is amikacin.

In one embodiment, the percent associated aminoglycoside post-nebulization is measured by reclaiming the aerosol from the air by condensation in a cold-trap, and the liquid is subsequently assayed for free and encapsulated aminoglycoside (associated aminoglycoside).

In one embodiment, the MMAD of the aerosol of the pharmaceutical formulation is less than 4.9 µm, less than 4.5 µm, less than 4.3 µm, less than 4.2 µm, less than 4.1 µm, less than 4.0 µm or less than 3.5 µm, as measured by the ACI at a gas flow rate of about 28 L/minute, or by the Next Generation Impactor NGI at a gas flow rate of about 15 L/minute.

In one embodiment, the MMAD of the aerosol of the pharmaceutical formulation is about 1.0 µm to about 4.2 µm, about 3.2 µm to about 4.2 µm, about 3.4 µm to about 4.0 µm, about 3.5 µm to about 4.0 µm or about 3.5 µm to about 4.2 µm, as measured by the ACI. In one embodiment, the MMAD of the aerosol of the pharmaceutical formulation is about 2.0 µm to about 4.9 µm, about 4.4 µm to about 4.9 µm, about 4.5 µm to about 4.9 µm, or about 4.6 µm to about 4.9 µm, as measured by the NGI.

In another embodiment, the nebulizer described herein generates an aerosol of the aminoglycoside pharmaceutical formulation at a rate greater than about 0.53 g per minute, greater than about 0.55 g per minute, or greater than about 0.60 g per minute or about 0.60 g per minute to about 0.70 g per minute. In a further embodiment, the FPF of the aerosol is greater than or equal to about 64%, as measured by the ACI, greater than or equal to about 70%, as measured by the ACI, greater than or equal to about 51%, as measured by the NGI, or greater than or equal to about 60%, as measured by the NGI.

In one embodiment, the system provided herein comprises a nebulizer selected from an electronic mesh nebulizer, pneumonic (jet) nebulizer, ultrasonic nebulizer, breath-enhanced nebulizer and breath-actuated nebulizer. In one embodiment, the nebulizer is portable.

The principle of operation of a pneumonic nebulizer is generally known to those of ordinary skill in the art and is described, e.g., in Respiratory Care, Vol. 45, No. 6, pp. 609-622 (2000). Briefly, a pressurized gas supply is used as the driving force for liquid atomization in a pneumatic nebulizer. Compressed gas is delivered, which causes a region of negative pressure. The solution to be aerosolized is then delivered into the gas stream and is sheared into a liquid film. This film is unstable and breaks into droplets because of surface tension forces. Smaller particles, i.e., particles with the MMAD and FPF properties described above, can then be formed by placing a baffle in the aerosol stream. In one pneumonic nebulizer embodiment, gas and solution is mixed prior to leaving the exit port (nozzle) and interacting with the baffle. In another embodiment, mixing does not take place until the liquid and gas leave the exit port (nozzle). In one embodiment, the gas is air, $O_2$ and/or $CO_2$.

In one embodiment, droplet size and output rate can be tailored in a pneumonic nebulizer. However, consideration should be paid to the formulation being nebulized, and whether the properties of the formulation (e.g., % associated aminoglycoside) are altered due to the modification of the nebulizer. For example, in one embodiment, the gas velocity and/or pharmaceutical formulation velocity is modified to achieve the output rate and droplet sizes of the present invention. Additionally or alternatively, the flow rate of the gas and/or solution can be tailored to achieve the droplet size and output rate of the invention. For example, an increase in gas velocity, in one embodiment, decreased droplet size. In one embodiment, the ratio of pharmaceutical formulation flow to gas flow is tailored to achieve the droplet size and output rate of the invention. In one embodiment, an increase in the ratio of liquid to gas flow increases particle size.

In one embodiment, a pneumonic nebulizer output rate is increased by increasing the fill volume in the liquid reservoir. Without wishing to be bound by theory, the increase in output rate may be due to a reduction of dead volume in the nebulizer. Nebulization time, in one embodiment, is reduced by increasing the flow to power the nebulizer. See, e.g., Clay et al. (1983). Lancet 2, pp. 592-594 and Hess et al. (1996). Chest 110, pp. 498-505.

In one embodiment, a reservoir bag is used to capture aerosol during the nebulization process, and the aerosol is subsequently provided to the subject via inhalation. In another embodiment, the nebulizer provided herein includes a valved open-vent design. In this embodiment, when the patient inhales through the nebulizer, nebulizer output is increased. During the expiratory phase, a one-way valve diverts patient flow away from the nebulizer chamber.

In one embodiment, the nebulizer provided herein is a continuous nebulizer. In other words, refilling the nebulizer with the pharmaceutical formulation while administering a dose is not needed. Rather, the nebulizer has at least an 8 mL capacity or at least a 10 mL capacity.

In one embodiment, a vibrating mesh nebulizer is used to deliver the aminoglycoside formulation of the invention to a patient in need thereof. In one embodiment, the nebulizer membrane vibrates at an ultrasonic frequency of about 100 kHz to about 250 kHz, about 110 kHz to about 200 kHz, about 110 kHz to about 200 kHz, about 110 kHz to about 150 kHz. In one embodiment, the nebulizer membrane vibrates at a frequency of about 117 kHz upon the application of an electric current.

In one embodiment, the nebulizer provided herein does not use an air compressor and therefore does not generate an air flow. In one embodiment, aerosol is produced by the aerosol head which enters the mixing chamber of the device. When the patient inhales, air enters the mixing chamber via one-way inhalation valves in the back of the mixing chamber and carries the aerosol through the mouthpiece to the patient. On exhalation, the patient's breath flows through the one-way exhalation valve on the mouthpiece of the device. In one embodiment, the nebulizer continues to generate aerosol into the mixing chamber which is then drawn in by the subject on the next breath—and this cycle continues until the nebulizer medication reservoir is empty.

Although not limited thereto, the present invention, in one embodiment, is carried out with one of the aerosol generators (nebulizers) depicted in FIGS. 1, 2, 3 and 4. Additionally, the systems of the invention, in one embodiment, include a nebulizer described in European Patent Applications 11169080.6 and/or 10192385.2. These applications are incorporated by reference in their entireties.

FIG. 1 shows a therapeutic aerosol device 1 with a nebulizing chamber 2, a mouthpiece 3 and a membrane aerosol generator 4 with an oscillating membrane 5. The oscillating membrane may, for example, be brought to oscillation by annular piezo elements (not shown), examples of which are described in WO 1997/29851.

Figure 2:
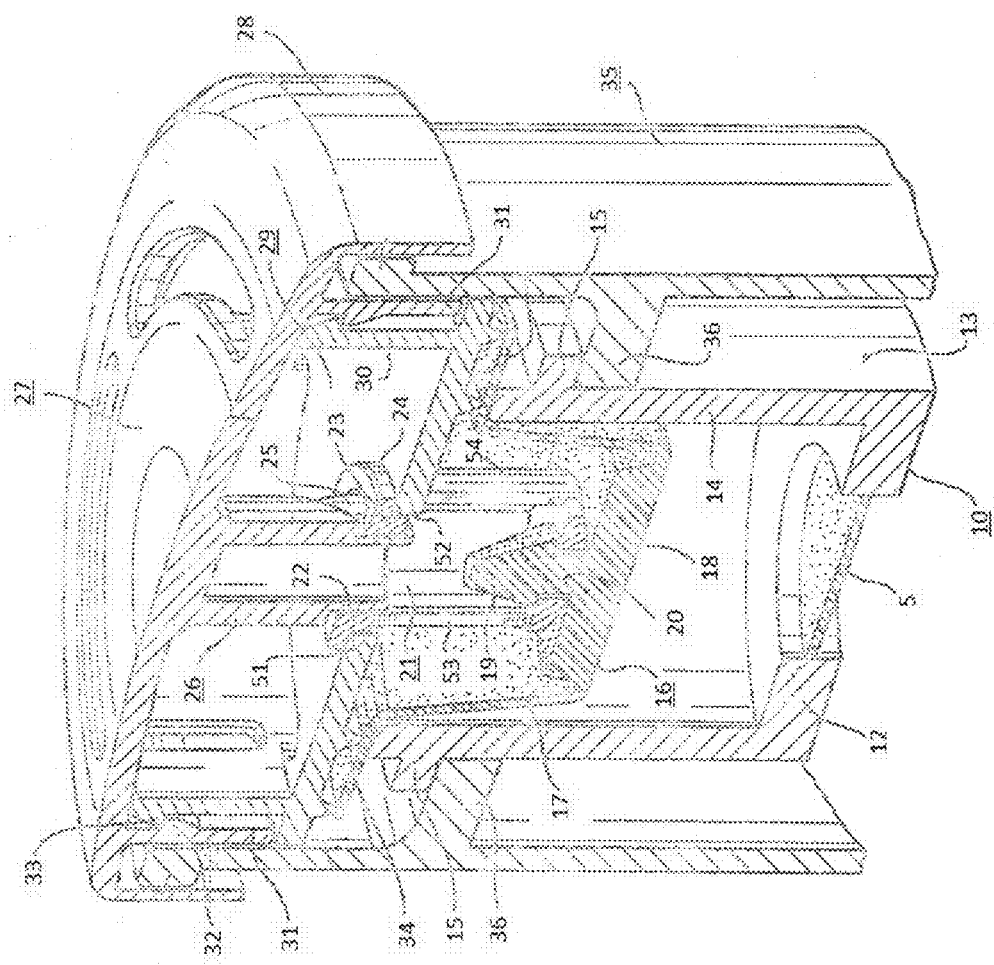
FIG. 2 is an enlarged representation of the nebulizer diagram shown in FIG. 1.
Figure 4:
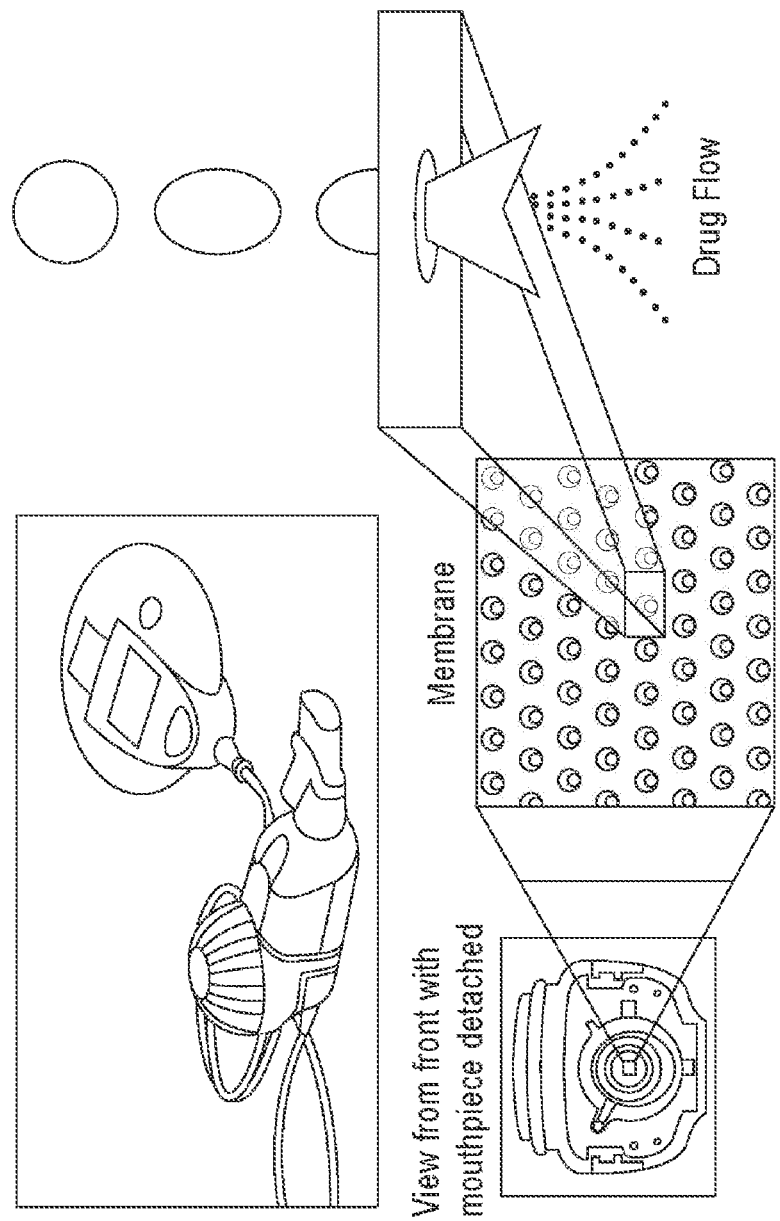
FIG. 4 is an image of a PARI eFlow® nebulizer, modified for use with the aminoglycoside formulations described herein, and a blown up diagram of the nebulizer's membrane.

When in use, the pharmaceutical formulation is located on one side of the oscillating membrane 5, see FIGS. 1, 2 and 4, and this liquid is then transported through openings in the oscillating membrane 5 and emitted on the other side of the oscillating membrane 5, see bottom of FIG. 1, FIG. 2, as an aerosol into the nebulizing chamber 2. The patient is able to breathe in the aerosol present in the nebulizing chamber 2 at the mouthpiece 3.

The oscillating membrane 5 comprises a plurality of through holes. Droplets of the aminoglycoside formulation are generated when the aminoglycoside pharmaceutical formulation passes through the membrane. In one embodiment, the membrane is vibratable, a so called active electronic mesh nebulizer, for example the eFlow® nebulizer from PARI Pharma, HL100 nebulizer from Health and Life, or the Aeroneb Go® from Aerogen (Novartis). In a further embodiment, the membrane vibrates at an ultrasonic frequency of about 100 kHz to about 150 kHz, about 110 kHz to about 140 kHz, or about 110 kHz to about 120 kHz. In a further embodiment, the membrane vibrates at a frequency of about 117 kHz upon the application of an electric current. In a further embodiment, the membrane is fixed and the a further part of the fluid reservoir or fluid supply is vibratable, a so called passive electronic mesh nebulizer, for example the MicroAir Electronic Nebulizer Model U22 from Omron or the I-Neb I-neb AAD Inhalation System from Philips Respironics.

In one embodiment, the length of the nozzle portion of the through holes formed in the membrane (e.g., vibratable membrane) influences the total output rate (TOR) of the aerosol generator. In particular, it has been found that the length of the nozzle portion is directly proportional to the total output rate, wherein the shorter the nozzle portion, the higher the TOR and vice versa.

In one embodiment, the nozzle portion is sufficiently short and small in diameter as compared to the upstream portion of the through hole. In a further embodiment, the length of the portions upstream of the nozzle portion within the through hole does not have a significant influence on the TOR.

In one embodiment, the length of the nozzle portion influences the geometric standard deviation (GSD) of the droplet size distribution of the aminoglycoside pharmaceutical formulation. Low GSDs characterize a narrow droplet size distribution (homogeneously sized droplets), which is advantageous for targeting aerosol to the respiratory system, for example for the treatment of bacterial infections (e.g., *Pseudomonas* or *Mycobacteria*) in cystic fibrosis patients, or the treatment of nontuberculosis *mycobacteria*, bronchiectasis (e.g., the treatment of cystic fibrosis or non-cystic fibrosis patients), *Pseudomonas* or *Mycobacteria* in patients. That is, the longer the nozzle portion the lower the GSD. The average droplet size, in one embodiment is less than 5 µm, and has a GSD in a range of 1.0 to 2.2, or about 1.0 to about 2.2, or 1.5 to 2.2, or about 1.5 to about 2.2.

In one embodiment, as provided above, the system provided herein comprises a nebulizer which generates an aerosol of the aminoglycoside pharmaceutical formulation at a rate greater than about 0.53 g per minute, or greater than about 0.55 g per minute. In a further embodiment, the nebulizer comprises a vibratable membrane having a first side for being in contact with the fluid and an opposite second side, from which the droplets emerge.

The membrane, e.g., a stainless steel membrane, may be vibrated by means of a piezoelectric actuator or any other suitable means. The membrane has a plurality of through holes penetrating the membrane in an extension direction from the first side to the second side. The through holes may be formed as previously mentioned by a laser source, electroforming or any other suitable process. When the membrane is vibrating, the aminoglycoside pharmaceutical formulation passes the through holes from the first side to the second side to generate the aerosol at the second side. Each of the through holes, in one embodiment, comprises an entrance opening and an exit opening. In a further embodiment, each of the through holes comprises a nozzle portion extending from the exit opening over a portion of the through holes towards the entrance opening. The nozzle portion is defined by the continuous portion of the through hole in the extension direction comprising a smallest diameter of the through hole and bordered by a larger diameter of the through hole. In one embodiment, the larger diameter of the through hole is defined as that diameter that is closest to 3 times, about 3 times, 2 times, about 2 times, 1.5 times, or about 1.5 times, the smallest diameter.

The smallest diameter of the through hole, in one embodiment, is the diameter of the exit opening. In another embodiment, the smallest diameter of the through hole is a diameter about 0.5×, about 0.6×, about 0.7×, about 0.8× or about 0.9× the diameter of the exit opening.

In one embodiment, the nebulizer provided herein comprises through holes in which the ratio of the total length of at least one of the through holes in the extension direction to the length of the respective nozzle portion of the through hole in the extension direction is at least 4, or at least about 4, or at least 4.5, or at least about 4.5, or at least 5, or at least about 5, or greater than about 5. In another embodiment, the nebulizer provided herein comprises through holes in which the ratio of the total length of the majority of through holes in the extension direction to the length of the respective nozzle portion of the through holes in the extension direction is at least 4, or at least about 4, or at least 4.5, or at least about 4.5, or at least 5, or at least about 5, or greater than about 5.

The extension ratios set forth above provide, in one embodiment, an increased total output rate, as compared to previously known nebulizers, and also provides a sufficient GSD. The ratio configurations, in one embodiment, achieve shorter application periods, leading to greater comfort for the patient and effectiveness of the aminoglycoside compound. This is particularly advantageous if the aminoglycoside compound in the formulation, due to its properties, is prepared at a low concentration, and therefore, a greater volume of the aminoglycoside pharmaceutical formulation must be administered in an acceptable time, e.g., one dosing session.

According to one embodiment, the nozzle portion terminates flush with the second side. Therefore, the length of the nozzle portion, in one embodiment, is defined as that portion starting from the second side towards the first side up to and bordered by the diameter that it is closest to about triple, about twice, about 2.5×, or about 1.5× the smallest diameter. The smallest diameter, in this embodiment, is the diameter of the exit opening.

In one embodiment, the smallest diameter (i.e., one border of the nozzle portion) is located at the end of the nozzle portion in the extension direction adjacent to the second side. In one embodiment, the larger diameter of the through hole, located at the other border of the nozzle portion, is located upstream of the smallest diameter in the direction in which the fluid passes the plurality of through holes during operation.

According to one embodiment, the smallest diameter is smaller than about 4.5 µm, smaller than about 4.0 µm, smaller than about 3.5 µm, or smaller than about 3.0 µm.

In one embodiment, the total length of at least one through hole in the extension direction is at least about 50 µm, at least about 60 µm, at least about 70 µm, or at least about 80 µm. In a further embodiment, the total length of at least one of the plurality of through holes is at least about 90 µm. In one embodiment, the total length of a majority of the plurality of through holes in the extension direction is at least about 50 µm, at least about 60 µm, at least about 70 µm, or at least about 80 µm. In a further embodiment, the total length of a majority of the plurality of through holes is at least about 90 µm.

The length of the nozzle portion, in one embodiment, is less than about 25 µm, less than about 20 µm or less than about 15 µm.

According to one embodiment, the through holes are laser-drilled through holes formed in at least two stages, one stage forming the nozzle portion and the remaining stage(s) forming the remainder of the through holes.

In another embodiment, the manufacturing methods used lead to a nozzle portion which is substantially cylindrical or conical with a tolerance of less than +100% of the smallest diameter, less than +75% of the smallest diameter, less than +50% of the smallest diameter, less than +30% of the smallest diameter, less than +25% of the smallest diameter, or less than +15% of the smallest diameter.

Alternatively or additionally, the through holes are formed in an electroforming process. In one embodiment, the through holes have a first funnel-shaped portion at the first side and a second funnel-shaped portion at the second side with the nozzle portion in-between the first and the second funnel-shaped portions and defined between the exit opening and the larger diameter. In this instance, the total length of the through holes may as well be defined by the distances from the first side to the exit opening (smallest diameter) only.

In addition, the total output rate (TOR) may be further increased by increasing the number of through holes provided in the membrane. In one embodiment, an increase in number of through holes is achieved by increasing the active perforated surface of the membrane and maintaining the distance of the through holes relative to each other at the same level. In another embodiment, the number of through holes is increased by reducing the distance of the through holes relative to each other and maintaining the active area of the membrane. In addition, a combination of the above strategies may be used.

In one embodiment, the total output rate of the nebulizer described herein is increased by increasing the density of through holes in the membrane. In one embodiment, the average distance between through holes is about 70 µm, or about 60 µm, or about 50 µm.

In one embodiment, the membrane comprises between about 200 and about 8,000 through holes, between about 1,000 and about 6,000 through holes, between about 2,000 and about 5,000 through holes or about 2,000 and about 4,000 through holes. In one embodiment, the number of through holes described above increases the TOR, and the TOR is increased regardless of whether the nozzle parameters are implemented as described above. In one embodiment, the nebulizer provided herein comprises about 3,000 through holes. In a further embodiment, the through holes are located in a hexagonal array, e.g., at about the center of the membrane (e.g., stainless steel membrane). In a further embodiment, the average distance between through holes is about 70 µm.

Figure 3:
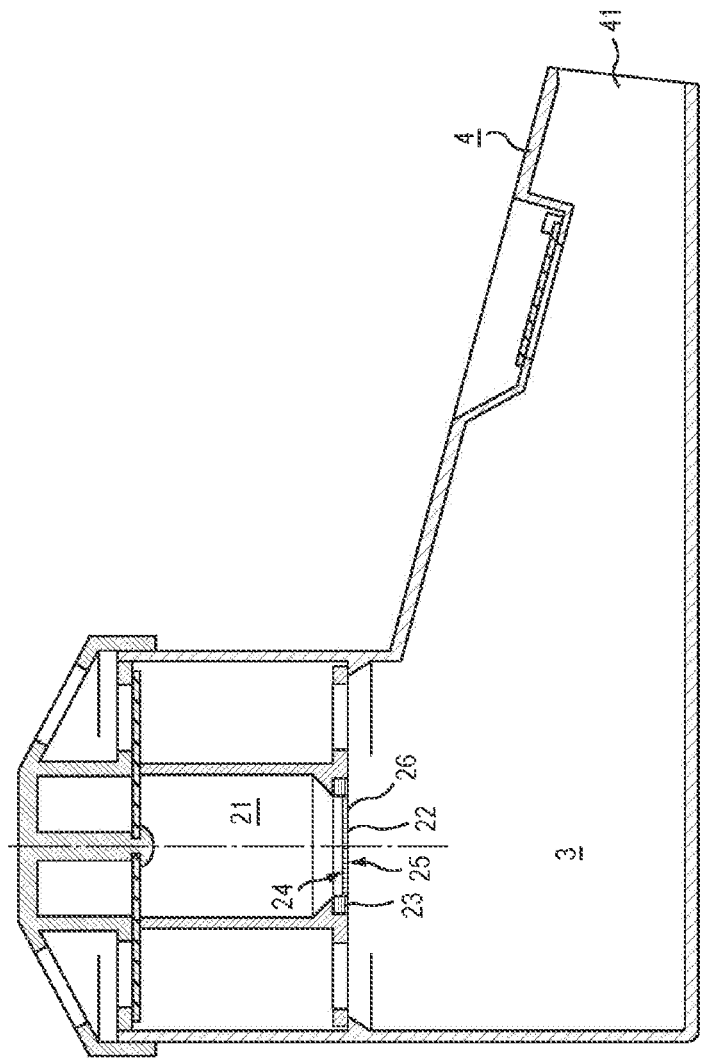
FIG. 3 shows a cross-sectional view of a generally known aerosol generator, as described in WO 2001/032246.

FIG. 3 shows an aerosol generator (nebulizer) as disclosed in WO 2001/032246, which is hereby incorporated by reference in its entirety. The aerosol generator comprises a fluid reservoir 21 to contain the pharmaceutical formulation, to be emitted into the mixing chamber 3 in the form of an aerosol and to be inhaled by means of the mouth piece 4 through the opening 41.

The aerosol generator comprises a vibratable membrane 22 vibrated by means of a piezoelectric actuator 23. The vibratable membrane 22 has a first side 24 facing the fluid container 21 and a second opposite side 25 facing the mixing chamber 3. In use, the first side 24 of the vibratable membrane 22 is in contact with the fluid contained in the fluid container 21. A plurality of through holes 26 penetrating the membrane from the first side 24 to the second side 25 are provided in the membrane 22. In use, the fluid passes from the fluid container 21 through the through holes 26 from the first 24 to the second side 25 when the membrane 22 is vibrated for generating the aerosol at the second side 25 and emitting it into the mixing chamber 3. This aerosol may then be drawn by inhalation of a patient from the mixing chamber 3 via the mouth piece 4 and its inhalation opening 41.

Figure 5:
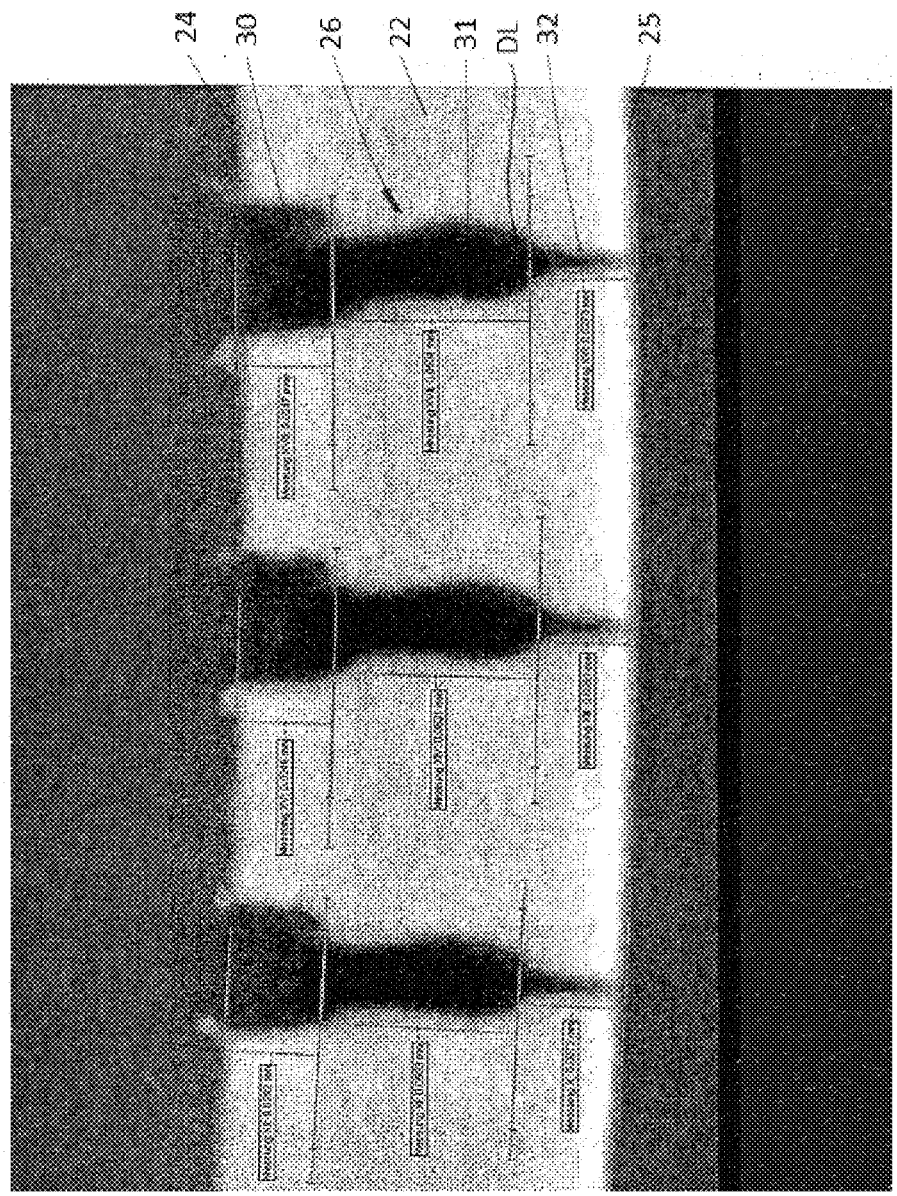
FIG. 5 is a cross-sectional computed tomography (CT) image showing a membrane having a relatively long nozzle portion.

FIG. 5 shows a cross-sectional computed tomography scan showing three of the through holes 26 of such a vibratable membrane 22. The through holes 26 of this particular embodiment are formed by laser drilling using three stages of different process parameters, respectively. In a first stage, the portion 30 is formed. In a second stage the portion 31 is formed and in a third stage the nozzle portion 32 is formed. In this particular embodiment, the length of the nozzle portion 32 is about 26 µm, whereas the portion 31 has a length of about 51 µm. The first portion 30 has a length of about 24.5 µm. As a result, the total length of each through hole is the sum of the length of the portion 30, the portion 31 and the nozzle portion 32, that is in this particular example, about 101.5 µm. Thus, the ratio of the total length of each through hole 26 in the extension direction E to the length of a respective one of the nozzle portions 32 in the extension direction E is approximately 3.9.

Figure 6:
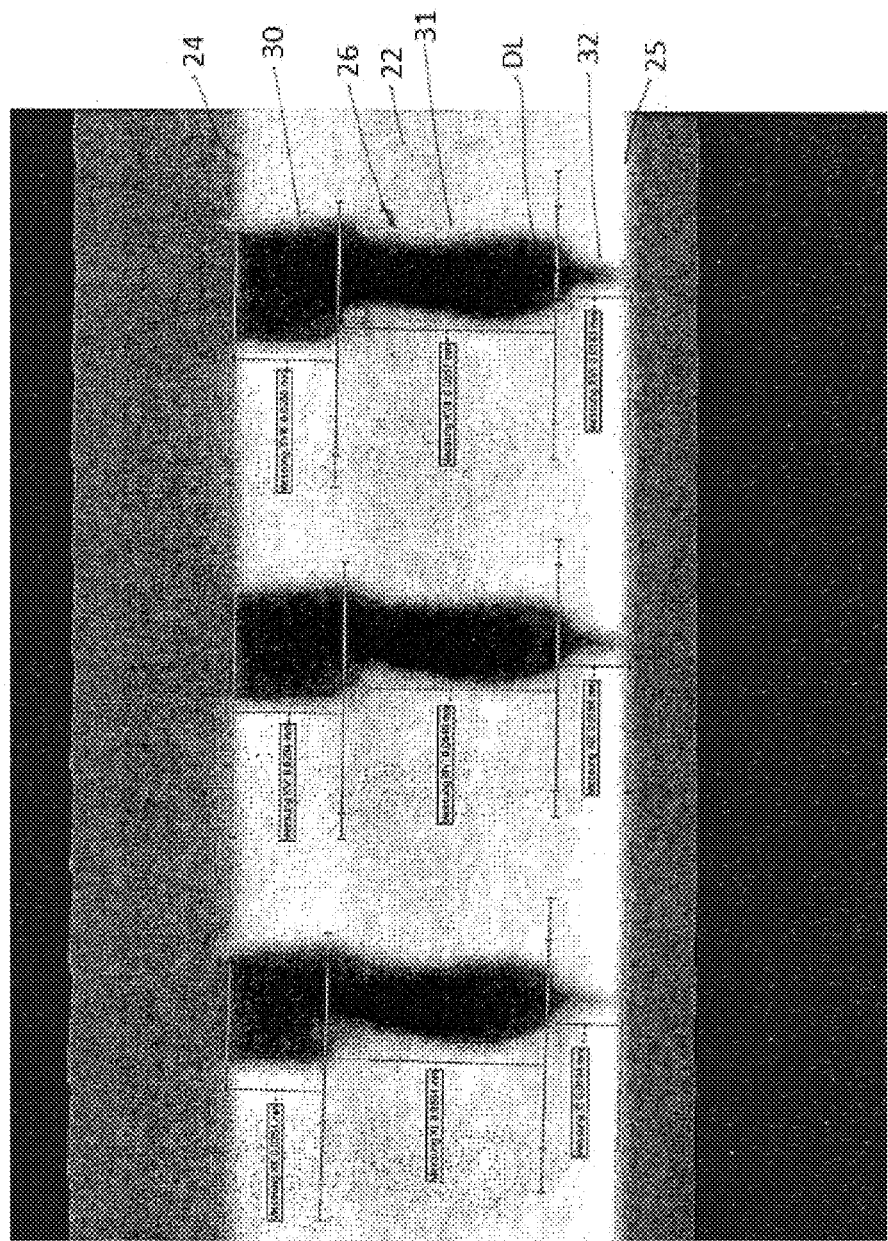
FIG. 6 is a cross-sectional computed tomography (CT) image of a stainless steel membrane having a relatively short nozzle portion.

In the embodiment in FIG. 6, the first portion 30 has a length of about 27 µm, the portion 31 a length of about 55 µm and a nozzle portion a length of about 19 µm. As a result, the total length of the through hole 26 is about 101 µm. Thus, the ratio of the total length of the through hole 26 to the length of the corresponding nozzle portion 32 in this embodiment is approximately 5.3.

Both the vibratable membranes in FIGS. 5 and 6 were manufactured with 6,000 through holes 26. The below table (Table 3) indicates the mass median diameter (MMD), as determined by laser diffraction, of the particles emitted at the second side of the membrane, the time required for completely emitting a certain amount of liquid (Nebulization time) as well as the TOR. The tests were performed with a liposomal formulation of amikacin.

TABLE 3

Properties of nebulizer membranes.

| Membrane | MMD (µm) | Nebulization time (min) | TOR (g/min.) | # of through holes 26 |
|---|---|---|---|---|
| 1 (shown in FIG. 5 with a nozzle portion of 26 µm) | 4.2 | 14.6 | 0.57 | 6,000 |
| 2 (shown in FIG. 6 with a nozzle portion of 19 µm) | 4.3 | 9.3 | 0.89 | 6,000 |
| 3 (similar to FIG. 6) | 4.4 | 13.4 | 0.62 | 3,000 |
| 4 (similar to FIG. 6, nozzle shorter than membrane 3) | 4.4 | 11.9 | 0.7 | 3,000 |

Table 3 shows that the membrane 2 with the shorter nozzle portion provides for an increased TOR and a reduced nebulization time by 5.3 minutes, which is approximately 36% less as compared to the membrane 1. Table 3 also shows that the MMD did not vary significantly for each membrane tested. This is in contrast to the differences in TOR observed for each membrane. Thus, in one embodiment, the nebulization time for the nebulizer described herein is reduced significantly as compared to prior art nebulizers, without affecting the droplet size, as measured by MMD.

In addition to the membrane shown in FIGS. 5 and 6, membranes were manufactured having the nozzle portion further reduced, and with 3,000 through holes 26 (membranes 3 and 4, Table 3). In particular, a membrane 3 was laser-drilled with a shorter nozzle portion, whereas membrane 4 was manufactured using a shorter nozzle portion than membrane 3. Table 3 indicates that even with 3,000 holes (membrane 3 and 4) a reduction in the length of the nozzle portion results in an increased TOR compared to membrane 1 with 6,000 holes. The comparison of the membrane 3 and 4 as compared to the membrane 2 further shows that a combination of a higher number of holes (6,000 as compared to 3,000) and a reduced length of the nozzle portion increases the TOR for the nebulizer.

In one embodiment, it is advantageous to use a laser drilling process as compared to electroforming for manufacturing the through holes. The through holes shown in FIGS. 5 and 6, manufactured by laser drilling, are substantially cylindrical or conical as compared to the funnel-shaped entrance and exit of electro-formed through holes, e.g., as disclosed in WO 01/18280. The vibration of the membrane, that is its vibration velocity, may be transferred to the pharmaceutical formulation over a larger area by means of friction when the through holes are substantially cylindrical or conical as compared to the funnel-shaped entrance and exit of electro-formed through holes. The pharmaceutical formulation, because of its own inertia, is then ejected from the exit openings of the through holes resulting in liquid jets collapsing to form the aerosol. Without wishing to be bound by theory, it is thought that because an electro-formed membrane comprises extremely bent surfaces of the through holes, the surface or area for transferring the energy from the membrane to the liquid is reduced.

However, the present invention may also be implemented in electro-formed membranes, wherein the nozzle portion is defined by the continuous portion of the through hole in the extension direction starting from the smallest diameter of the through hole towards the first side until it reaches a diameter 2× or 3× of the smallest diameter of the hole. In one embodiment, the total length of the through hole is measured from the smallest diameter to the first side.

Referring again to FIG. 1, so that the patient does not have to remove or to put down the therapeutic device from his mouth after inhaling the aerosol, the mouthpiece 3 has an opening 6 sealed by an elastic valve element 7 (exhalation valve). If the patient exhales into the mouthpiece 3 and hence into the nebulizing chamber 2, the elastic valve element 7 opens so that the exhaled air is able to escape from the interior of the therapeutic aerosol. On inhalation, ambient air flows through the nebulizing chamber 2. The nebulizing chamber 2 has an opening sealed (not shown) by a further elastic valve element (inhalation valve). If the patient inhales through the mouthpiece 3 and sucks from the nebulizing chamber 2, the elastic valve element opens so that the ambient air is able to enter into the nebulizing chamber and mixed with the aerosol and leave the interior of the nebulizing chamber 2 to be inhaled. Further description of this process is provided in U.S. Pat. No. 6,962,151, which is incorporated by reference in its entirety for all purposes.

The nebulizer shown in FIG. 2 comprises a cylindrical storage vessel 10 to supply a liquid that is fed to the membrane 5. As shown in FIG. 2, the oscillating membrane 5 may be arranged in an end wall 12 of the cylindrical liquid reservoir 10 to ensure that the liquid poured into the liquid reservoir comes into direct contact with the membrane 5 when the aerosol generator is held in the position shown in FIG. 1. However, other methods may also be used to feed the liquid to the oscillating membrane without any change being necessary to the design of the device according to the invention for the generation of a negative pressure in the liquid reservoir.

On the side facing the end wall 12, the cylindrical liquid container 10 is open. The opening is used to pour the liquid into the liquid reservoir 10. Slightly below the opening on the external surface 13 of the peripheral wall 14 there is a projection 15 which serves as a support when the liquid container is inserted in an appropriately embodied opening in a housing 35.

The open end of the liquid container 10 is closed by a flexible sealing element 16. The sealing element 16 lies on the end of the peripheral wall 14 of the liquid container 10 and extends in a pot-shaped way into the interior of the liquid container 10 whereby a conically running wall section 17 is formed in the sealing element 16 and closed off by a flat wall section 18 of the sealing element 16. As discussed further below, forces act via the flat wall section 18 on the sealing element 16 and so in one embodiment the flat wall section 18 is thicker than the other sections of the sealing element 16. On the perimeter of the flat wall section 18, there is a distance to the conical wall section 17 so that the conical wall section 17 may be folded when the flat wall section 18 is moved upwards, relative to the representation in FIG. 2.

On the side of the flat wall section 18 facing away from the interior of the liquid container, there is a projection comprising a truncated cone section 19 and a cylindrical section 20. This design enables the projection to be introduced and latched into an opening adapted to match the cylindrical section since the flexible material of the sealing element 16 permits the deformation of the truncated cone section 19.

In one embodiment, the aerosol generator 4 comprises a slidable sleeve 21 equipped with an opening of this type which is substantially a hollow cylinder open on one side. The opening for the attachment of the sealing element 16 is embodied in an end wall of the slidable sleeve 21. When the truncated cone 19 has latched into place, the end wall of the slidable sleeve 21 containing the opening lies on the flat sealing element wall section 18. The latching of the truncated cone 19 into the slidable sleeve enables forces to be transmitted from the slidable sleeve 21 onto the flat wall section 18 of the sealing element 16 so that the sealing section 18 follows the movements of the slidable sleeve 21 in the direction of the central longitudinal axis of the liquid container 10.

In a generalized form, the slidable sleeve 21 may be seen as a slidable element, which may, for example, also be implemented as a slidable rod which may be stuck-on or inserted in a drill hole. Characteristic of the slidable element 21 is the fact that it may be used to apply a substantially linearly directed force onto the flat wall element 18 of the sealing element 16. Overall, the decisive factor for the mode of operation of the aerosol generator according to the invention is the fact that a slidable element transmits a linear movement onto the sealing element so that an increase in volume occurs within the liquid reservoir 10. Since the liquid reservoir 10 is otherwise gas-tight, this causes a negative pressure to be generated in the liquid reservoir 10.

The sealing element 16 and the slidable element 21 may be produced in one piece, i.e., in one operation, but from different materials. The production technology for this is available so that a one-piece component for the nebulizer is created, e.g., in a fully automatic production step.

In one embodiment, the slidable sleeve 21 is open on the end facing the drill hole for the truncated cone but at least two diametrically opposite lugs 22 and 23 protrude radially into the interior of the slidable sleeve 21. A collar 24 encircling the slidable sleeve extends radially outwards. While the collar 24 is used as a support for the slidable sleeve 21 in the position shown in FIG. 5, the projections 22 and 23 protruding into the interior of the slidable sleeve 21 are used to absorb the forces acting on the slidable sleeve 21 in particular parallel to the central longitudinal axis. In one embodiment, these forces are generated by means of two spiral grooves 25 which are located on the outside of the peripheral wall of a rotary sleeve 26.

In one embodiment, the nebulizer may be implemented with one of the projections 22 or 23 and one groove 25. In a further embodiment, a uniformly distributed arrangement of two or more projections and a corresponding number of grooves is provided.

In one embodiment, the rotary sleeve 26 is also a cylinder open on one side whereby the open end is arranged in the slidable sleeve 21 and is hence facing the truncated cone 19 enabling the truncated cone 19 to penetrate the rotary sleeve 26. In addition, the rotary sleeve 26 is arranged in the slidable sleeve 21 in such a way that the projections 22 and 23 lie in the spiral grooves 25. The inclination of the spiral groove 25 is designed so that, when the rotary sleeve 26 is rotated in relation to the slidable sleeve 21, the projections 22 and 23 slide along the spiral grooves 25 causing a force directed parallel to the central longitudinal axis to be exerted on the sliding projections 22 and 23 and hence on the slidable sleeve 21. This force displaces the slidable sleeve 21 in the direction of the central longitudinal axis so that the sealing element 16 which is latched into the slidable sleeve's drill hole by means of the truncated cone is also substantially displaced parallel to the central longitudinal axis.

The displacement of the sealing element 16 in the direction of the central longitudinal axis of the liquid container 10 generates a negative pressure in the liquid container 10, determined inter alia by the distance by which the slidable sleeve 21 is displaced in the direction of the central longitudinal axis. The displacement causes the initial volume $V_{R1}$ of the gas-tight liquid container 10 to increase to the volume $V_{RN}$ and thereby a negative pressure to be generated. The displacement is in turn defined by the design of the spiral grooves 25 in the rotary sleeve 26. In this way, the aerosol generator according to the invention ensures that the negative pressure in the liquid reservoir 10 may be generated in the relevant areas by means of simple structural measures.

To ensure that the forces to be applied to generate the negative pressure when handling the device remain low, the rotary sleeve 26 is embodied in one piece with a handle 27 whose size is selected to enable the user to rotate the handle 27, and hence the rotary sleeve 26, manually without great effort. The handle 27 substantially has the shape of a flat cylinder or truncated cone which is open on one side so that a peripheral gripping area 28 is formed on the external periphery of the handle 27 which is touched by the user's hand to turn the handle 27.

Due to the design of the spiral grooves 25 and the overall comparatively short distance to be traveled by the slidable sleeve 21 in the longitudinal direction to generate a sufficient negative pressure, in one embodiment, it is sufficient to turn the handle 27 and hence the rotary sleeve 26 through a comparatively small angle of rotation. In one embodiment, the angle of rotation lies within a range from 45 to 360 degrees. This embodiment allows for the ease of handling of the device according to the invention and the therapeutic aerosol generator equipped therewith.

In order to create a unit which may be operated simply and uniformly from the slidable sleeve 21 and the rotary sleeve 26 including the handle 27, in one embodiment, the aerosol generator described here has a bearing sleeve 29 for bearing the slidable sleeve 21, which substantially comprises a flat cylinder open on one side. The diameter of the peripheral wall 30 of the bearing sleeve 29 is smaller than the internal diameter of the handle 27 and, in the example of an embodiment described, is aligned on the internal diameter of a cylindrical latching ring 31 which is provided concentrically to the gripping area 28 of the handle 27 but with a smaller diameter on the side of the handle 27 on which the rotary sleeve 26 is also arranged. Embodied on the side of the cylindrical latching ring 31 facing the rotary sleeve is a peripheral latching edge 32 which may be brought into engagement with latching lugs 33 situated at intervals on the peripheral wall 30 of the bearing sleeve 29. This allows the handle 27 to be located on the bearing sleeve 29 whereby, as shown in FIG. 5, the handle 27 is placed on the open end of the bearing sleeve 29 and the latching edge 32 is interlatched with the latching lugs 33.

To hold the slidable sleeve 21, an opening is provided in the centre of the sealed end of the bearing sleeve 29 in which the slidable sleeve 21 is arranged, as may be identified in FIG. 2. The collar 24 of the slidable sleeve 21 lies in the position shown in FIG. 2 on the surface of the end wall of the bearing sleeve 29 facing the handle. Extending into the bearing opening are two diametrically opposite projections 51 and 52, which protrude into two longitudinal grooves 53 and 54 on the peripheral surface of the slidable sleeve 21. The longitudinal grooves 53 and 54 run parallel to the longitudinal axis of the slidable sleeve 21. The guide projections 51 and 52 and the longitudinal grooves 53 and 54 provide anti-rotation locking for the slidable sleeve 21 so that the rotational movement of the rotary sleeve 26 results not in rotation but in the linear displacement of the slidable sleeve 21. As is evident from FIG. 2, this ensures that the slidable sleeve 21 is held in the combination of the handle 27 and the bearing sleeve 29 in an axially displaceable way but locked against rotation. If the handle 27 is rotated in relation to the bearing sleeve 29, the rotary sleeve 26 also rotates in relation to the slidable sleeve 21 whereby the sliding projections 22 and 23 move along the spiral grooves 25. This causes the slidable sleeve 21 to be displaced in an axial direction in the opening of the bearing sleeve 29.

It is possible to dispense with the guide projections 51 and 52 in the bearing opening and the longitudinal grooves 53 and 54 in the slidable sleeve 21. In one embodiment, the guide projections 51 and 52 and the longitudinal grooves 53 and 54 are not present in the aerosol generator, and the truncated cone 19, the cylinder sections 20 of the sealing elements 16 and the large-area support for the slidable sleeve 21 holding the truncated cone on the flat sealing element section 18 achieves anti-rotation locking of the slidable sleeve 21 by means of friction. In a further embodiment, the sealing element 16 is fixed so it is unable to rotate in relation to the bearing sleeve 29.

In one embodiment, provided on the surface of the sealed end of the bearing sleeve 19 facing away from the handle, is an annular first sealing lip 34 concentric to the opening holding the slidable sleeve. The diameter of the first sealing lip 34 corresponds to the diameter of the peripheral wall 14 of the liquid container 10. As provided in FIG. 2, this ensures that the first sealing lip 34 presses the sealing element 16 on the end of the peripheral wall against the liquid reservoir 10 in such a way that the liquid reservoir 10 is sealed. In addition, the first sealing lip 34 may also fix the sealing element 16 so that it is unable to rotate in relation to the liquid reservoir 10 and the bearing sleeve 29. In one embodiment, excessive force need not be applied in order to ensure that the aforesaid components of the device are unable to rotate in relation to each other.

In one embodiment, the forces required are generated at least to some extent by means of an interaction between the handle 27 and the housing 35 in which the pharmaceutical formulation reservoir is embodied as one piece or in which the pharmaceutical formulation (liquid) reservoir 10 is inserted as shown in FIG. 2. In this case, the pharmaceutical formulation reservoir 10 inserted in the casing with the peripheral projection 15 lies at intervals on a support 36 in the housing 35 which extends radially into the interior of the housing 35. This allows the liquid reservoir 10 to be easily removed from the housing 35 for purposes of cleaning. In the embodiment shown in FIG. 2, support is only provided at intervals, and therefore, openings are provided for ambient air when the patient inhales, described in more detail below.

Identifiable in FIG. 2 is the rotary lock, which is implemented by means of the handle 27 on the one hand and the housing 35 on the other. Shown are the locking projections 62 and 63 on the housing 35. However, there are no special requirements with regard to the design of the rotary lock as far as the device according to invention is concerned for the generation of the negative pressure in the liquid reservoir 10.

In one embodiment, the liquid reservoir 10 is configured to have a volume $V_{RN}$ of at least at least 16 mL, at least about 16 mL, at least 18 mL, at least about 18 mL, at least 20 mL or at least about 20 mL so that when for example, an amount of 8 mL of liquid (e.g., aminoglycoside pharmaceutical formulation) to be emitted in the form of an aerosol is contained in (filled or poured into) the liquid reservoir 10, an air cushion of 8 mL or about 8 mL is provided. That is, the ratio of the volume $V_{RN}$ to the initial volume of liquid $V_L$ within the liquid reservoir 10 is at least 2.0 and the ratio between the volume $V_A$ of a gas and $V_L$ of the liquid is at least 1.0. It has been shown that a liquid reservoir having a volume $V_{RN}$ of about 15.5 mL, about 19.5 mL and about 22.5 mL are efficient, and that efficiency increases with the increase in $V_{RN}$.

In one embodiment, the ratio between $V_{RN}$ and $V_L$ is at least 2.0, at least about 2.0, at least 2.4, at least about 2.4, at least 2.8 or at least about 2.8. In one embodiment, the ratio between $V_A$ and $V_L$ is at least 1.0, at least 1.2, at least 1.4, at least 1.6 or at least 1.8. In another embodiment, the ratio between $V_A$ and $V_L$ is at least about 1.0, at least about 1.2, at least about 1.4, at least about 1.6 or at least about 1.8.

The volume of the air cushion, in one embodiment, is at least 2 mL, at least about 2 mL, at least 4 mL, at least about 4 mL, is at least 6 mL, at least about 6 mL, at least 8 mL, at least about 8 mL, at least 10 mL, at least about 10 mL, at least 11 mL, at least about 11 mL, at least 12 mL, at least about 12 mL, at least 13 mL, at least about 13 mL, at least 14 mL or at least about 14 mL. In one embodiment, the volume of the air cushion is at least about 11 mL or at least about 14 mL. In one embodiment, the volume of the air cushion is from about 6 mL to about 15 mL, and the ratio between $V_{RN}$ and $V_L$ is at least about 2.0 to at least about 3.0. In a further embodiment, the between $V_{RN}$ and $V_L$ is at least about 2.0 to about at least about 2.8.

The volume of the air cushion, in one embodiment, is about 2 mL, about 4 mL, about 6 mL, about 8 mL, about 10 mL, about 11 mL, about 12 mL, about 13 mL, or about 14 mL.

In one embodiment, the ratio of the volume $V_{RN}$ to the initial volume of liquid $V_L$ is at least 2.0. Theoretically an unlimited enlargement of the increased volume $V_{RN}$ of the liquid reservoir 10 will result in a nearly stable negative pressure range. In one embodiment, the ratio of the volume $V_{RN}$ to the initial volume of liquid $V_L$ is within the range between 2.0 and 4.0 and in a further embodiment is between 2.4 and 3.2. Two examples of the ratio ranges ($V_{RN}/V_L$) for different initial volume of liquid $V_L$ between 4 mL and 8 mL are given in Table 4, below.

TABLE 4

| Nebulizer Reservoir specifications | | |
|---|---|---|
| $V_L$ | $V_{RN}$ | Ratio ($V_{RN}/V_L$) |
| 4 mL | 8.0-16.0 | 2.0-4.0 |
| 4 mL | 9.5-12.8 | 2.4-3.2 |
| 5 mL | 10.0-20.0 | 2.0-4.0 |
| 5 mL | 12.0-16.0 | 2.4-3.2 |
| 6 mL | 12.0-24.0 | 2.0-4.0 |
| 6 mL | 14.5-19.2 | 2.4-3.2 |
| 8 mL | 16.0-32.0 | 2.0-4.0 |
| 8 mL | 19.5-25.6 | 2.4-3.2 |

The systems provided herein may be used to treat a variety of pulmonary infections in subjects in need thereof. Among the pulmonary infections (such as in cystic fibrosis patients) that can be treated with the methods of the invention are gram negative infections. In one embodiment, infections caused by the following bacteria are treatable with the systems and formulations provided herein: *Pseudomonas* (e.g., *P. aeruginosa, P. paucimobilis, P. putida, P. fluorescens*, and *P. acidovorans*), *Burkholderia* (e.g., *B. pseudomallei, B. cepacia, B. cepacia complex, B. dolosa, B. fungorum, B. gladioli, B. multivorans, B. vietnamiensis, B. pseudomallei, B. ambifaria, B. andropogonis, B. anthina, B. brasilensis, B. calcdonica, B. caribensis, B. caryophylli*), *Staphylococcus* (e.g., *S. aureus, S. auricularis, S. carnosus, S. epidermidis, S. lugdunensis*), Methicillin-resistant *Staphylococcus aureus* (MRSA), *Streptococcus* (e.g., *Streptococcus pneumoniae*), *Escherichia coli, Klebsiella, Enterobacter, Serratia, Haemophilus, Yersinia pestis, Mycobacterium*, nontuberculous *mycobacterium* (e.g., *M. avium, M. avium* subsp. *hominissuis* (MAH), *M. abscessus, M. chelonae, M. bolletii, M. kansasii, M. ulcerans, M. avium, M. avium complex* (MAC) (*M. avium* and *M. intracellulare*), *M. conspicuum, M. kansasii, M. peregrinum, M. immunogenum, M. xenopi, M. marinum, M. malmoense, M. marinum, M. mucogenicum, M. nonchromogenicum, M. scrofulaceum, M. simiae, M. smegmatis, M. szulgai, M. terrae, M. terrae* complex, *M. haemophilum, M. genavense, M. asiaticum, M. shimoidei, M. gordonae, M. nonchromogenicum, M. triplex, M. lentiflavum, M. celatum, M. fortuitum, M. fortuitum* complex (*M. fortuitum* and *M. chelonae*)).

In one embodiment, the systems described herein are used to treat an infection caused by a nontuberculous mycobacterial infection. In one embodiment, the systems described herein are used to treat an infection caused by *Pseudomonas aeruginosa, Mycobacterium* abscessus, *Mycobacterium avium* or *M. avium* complex. In a further embodiment, a patient with cystic fibrosis is treated for a *Pseudomonas aeruginosa, Mycobacterium* abscessus, *Mycobacterium avium*, or *Mycobacterium avium* complex infection with one or more of the systems described herein. In even a further embodiment, the *Mycobacterium avium* infection is *Mycobacterium avium* subsp. *hominissuis.*

In one embodiment, a patient with cystic fibrosis is treated for a pulmonary infection with one of the systems provided herein. In a further embodiment, the pulmonary infection is a *Pseudomonas* infection. In yet a further embodiment, the *Pseudomonas* infection is *P. aeruginosa*. In a further embodiment, the aminoglycoside in the system is amikacin.

In one embodiment, the system provided herein is used for the treatment or prophylaxis of *Pseudomonas aeruginosa, Mycobacterium* abscessus, *Mycobacterium avium* or *Mycobacterium avium* complex lung infection in a cystic fibrosis patient or a non-cystic fibrosis patient. In a further embodiment, the system provided herein comprises a liposomal aminoglycoside formulation. In a further embodiment, the aminoglycoside is selected from amikacin, apramycin, arbekacin, astromicin, capreomycin, dibekacin, framycetin, gentamicin, hygromycin B, isepamicin, kanamycin, neomycin, netilmicin, paromomycin, rhodestreptomycin, ribostamycin, sisomicin, spectinomycin, streptomycin, tobramycin, verdamicin or a combination thereof. In even a further embodiment, the aminoglycoside is amikacin, e.g., amikacin sulfate.

Figure 7:
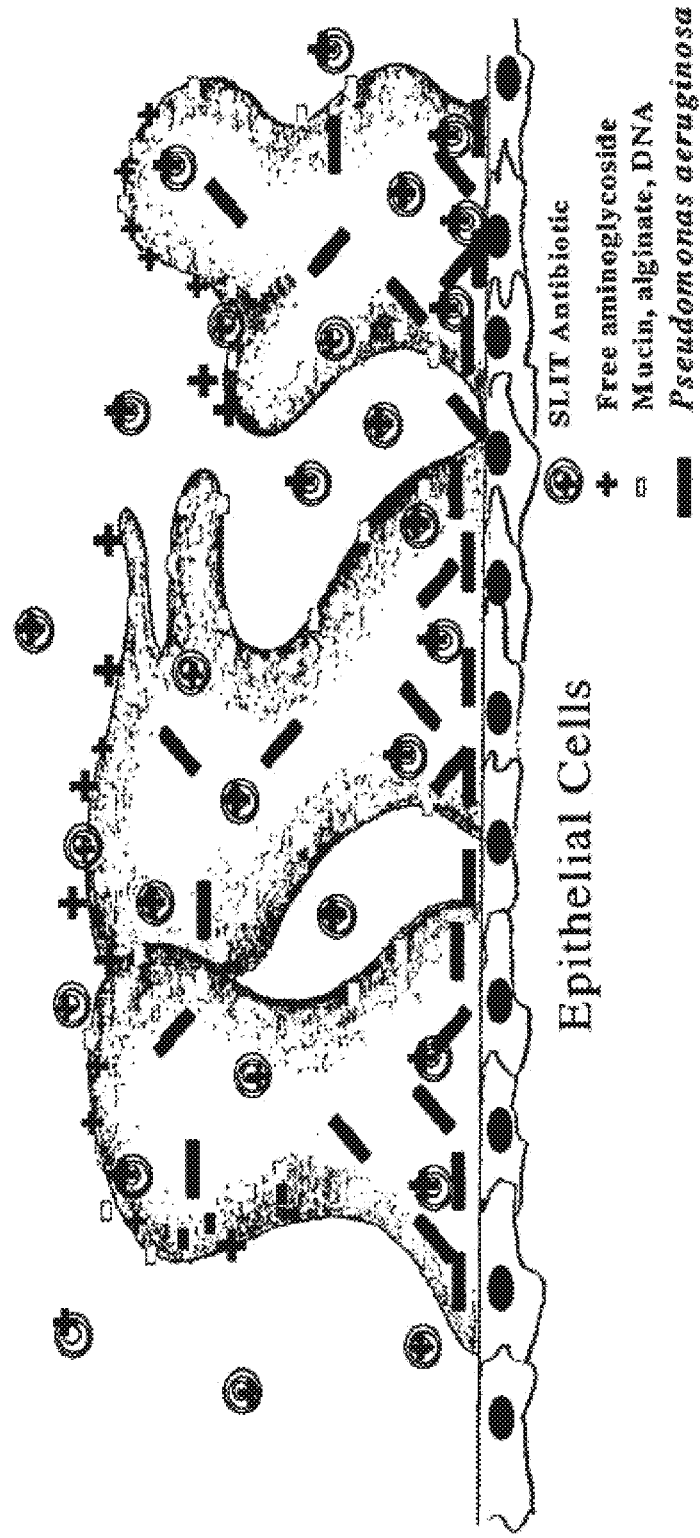
FIG. 7 is a cross sectional cartoon depiction of the sputum/biofilm seen, for example, in patients with cystic fibrosis.
Figure 8:
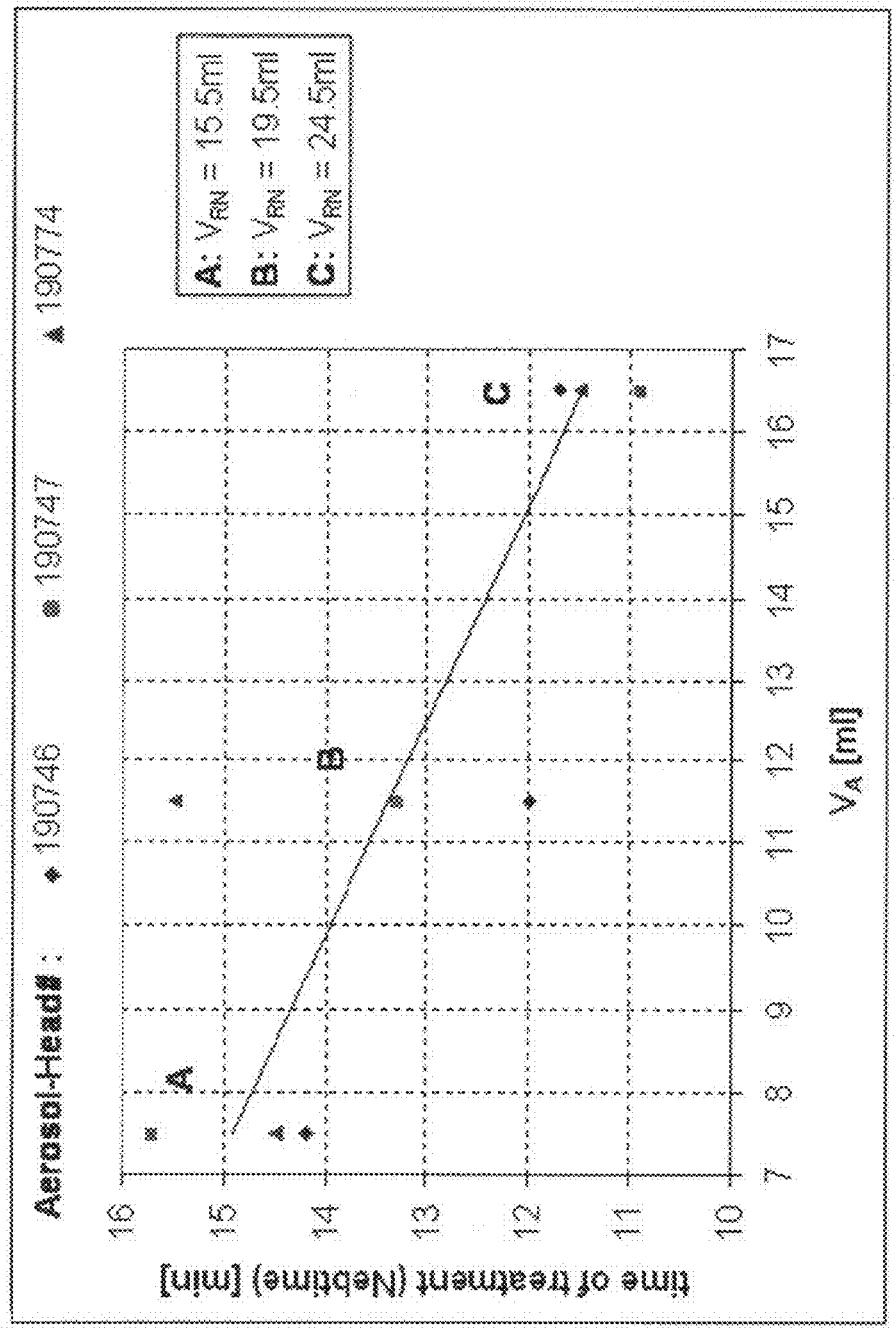
FIG. 8 is a graph of the time period of aerosol generation upon complete emission of the liquid within the liquid reservoir (Nebulization time) as a function of the initial gas cushion within the liquid reservoir ($V_A$).
Figure 9:
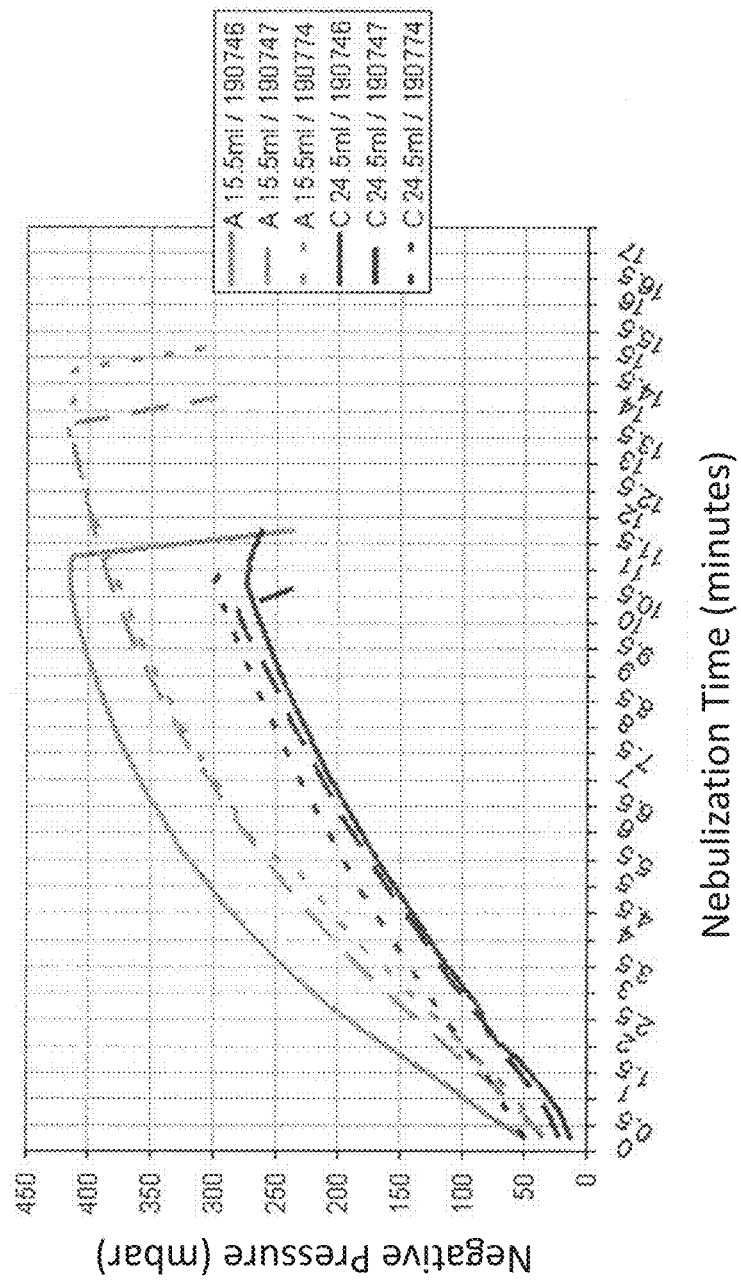
FIG. 9 is a graph of negative pressure in the nebulizer as a function of the time of aerosol generation until complete emission of the pharmaceutical formulation from the liquid reservoir (nebulization time).
Figure 10:
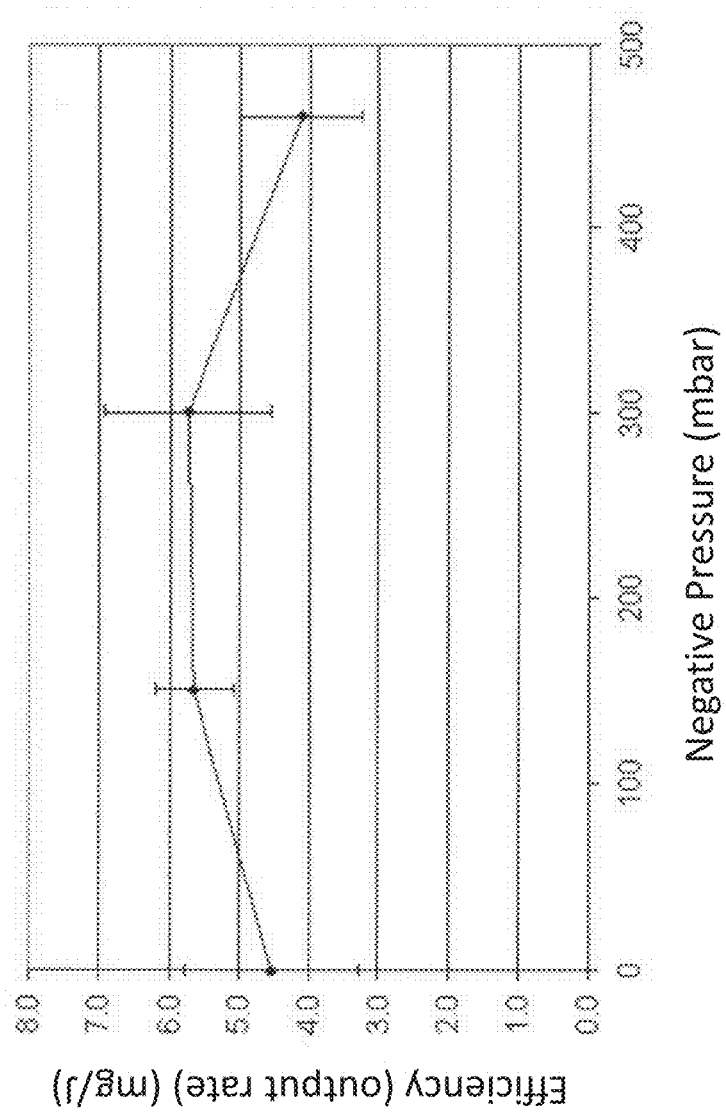
FIG. 10 is a graph of aerosol generation efficiency as a function of the negative pressure in the nebulizer.

An obstacle to treating infectious diseases such as *Pseudomonas aeruginosa*, the leading cause of chronic illness in cystic fibrosis patients is drug penetration within the sputum/biofilm barrier on epithelial cells (FIG. 7). In FIG. 7, the donut shapes represent liposomal/complexed aminoglycoside, the "+" symbol represents free aminoglycoside, the "−" symbol mucin, alginate and DNA, and the solid bar symbol represents *Pseudomonas aeruginosa*. This barrier comprises both colonized and planktonic *P. aeruginosa* embedded in alginate or exopolysaccharides from bacteria, as well as DNA from damaged leukocytes, and mucin from lung epithelial cells, all possessing a net negative charge. The negative charge binds up and prevents penetration of positively charged drugs such as aminoglycosides, rendering them biologically ineffective (Mendelman et al., 1985). Without wishing to be bound by theory, entrapment of aminoglycosides within liposomes or lipid complexes shields or partially shields the aminoglycosides from non-specific binding to the sputum/biofilm, allowing for liposomes or lipid complexes (with entrapped aminoglycoside) to penetrate (FIG. 7).

In another embodiment, a patient is treated for nontuberculous *mycobacteria* lung infection with one of the systems provided herein. In a further embodiment, the system provided herein comprises a liposomal amikacin formulation.

In another embodiment, the system provided herein is used for the treatment or prophylaxis of one or more bacterial infections in a cystic fibrosis patient. In a further embodiment, the system provided herein comprises a liposomal aminoglycoside formulation. In a further embodiment, the aminoglycoside is amikacin.

In another embodiment, the system provided herein is used for the treatment or prophylaxis of one or more bacterial infections in a patient with bronchiectasis. In a further embodiment, the system provided herein comprises a liposomal aminoglycoside formulation. In a further embodiment, the aminoglycoside is amikacin or amikacin sulfate.

In yet another embodiment, the system provided herein is used for the treatment or prophylaxis of *Pseudomonas aeruginosa* lung infections in non-CF bronchiectasis patients. In a further embodiment, the system provided herein comprises a liposomal aminoglycoside formulation. In a further embodiment, the aminoglycoside is amikacin.

As provided herein, the present invention provides aminoglycoside formulations administered via inhalation. In one embodiment, the MMAD of the aerosol is about 3.2 µm to about 4.2 µm, as measured by the Anderson Cascade Impactor (ACI), or about 4.4 μm to about 4.9 μm, as measured by the Next Generation Impactor (NGI).

In one embodiment, the nebulization time of an effective amount of an aminoglycoside formulation provided herein is less than 20 minutes, less than 18 minutes, less than 16 minutes or less than 15 minutes. In one embodiment, the nebulization time of an effective amount of an aminoglycoside formulation provided herein is less than 15 minutes or less than 13 minutes. In one embodiment, the nebulization time of an effective amount of an aminoglycoside formulation provided herein is about 13 minutes.

In one embodiment, the formulation described herein is administered once daily to a patient in need thereof.

EXAMPLES

The present invention is further illustrated by reference to the following Examples. However, it should be noted that these Examples, like the embodiments described above, are illustrative and are not to be construed as restricting the scope of the invention in any way.

Example 1

Comparison of Nebulizer Reservoir Volumes

In this example, the aerosol generator was an investigational eFlow® nebulizer, modified for use with liposomal aminoglycoside formulations provided herein, of Pari Pharma GmbH, Germany. A first aerosol generator had an initial volume of the liquid reservoir $V_{R1}$ of 13 ml, (A), a second one of 17 mL (B), a third one of 22 mL (C) and a fourth one of 20 mL (D). That is the increased volume $V_{RN}$ of the first one had 15.5 mL, the second one 19.5 mL, the third 24.5 mL and the fourth 22.5 mL.

8 mL of a liposomal amikacin formulation was poured into the liquid reservoir 10. As shown in FIG. 8, an air cushion of 8 mL resulted in an aerosol generation time period upon complete emission of 8 mL of the formulation in the liquid reservoir of between 14 and 16 minutes. An air cushion of 12 mL, however, decreased the aerosol generation time to a range between 12 and approximately 13 minutes. The air cushion of 17 mL further decreases the aerosol generation time to an amount between 10 and 12 minutes (FIG. 6).

Further, the first (A) and third (C) version of the aerosol generator had been used together with 8 mL of the liposomal amikacin formulation. An initial negative pressure of equal to or less than 50 mbar was generated within the liquid reservoir. In addition, the negative pressure was measured during the aerosol generation and is shown over the aerosol generation time in FIG. 9. In other words, FIG. 9 shows experimental data comparing the negative pressure range during the aerosol generation time for a liquid reservoir (C) having a volume $V_{RN}$ of 24.5 mL and a liquid reservoir (A) having a volume $V_{RN}$ of 15.5 mL. The initial amount of amikacin formulation $V_L$ was 8 mL and the initial negative pressure was about 50 mbar. The graph indicates that a larger air cushion prevents the negative pressure from increasing above a critical value of 300 mbar.

The dependence of aerosol generator efficiency (proportional to liquid output rate or total output rate) on different negative pressures was measured with the nebulizer described above. A liposomal amikacin formulation having a viscosity in the range of 5.5 to 14.5 mPa×s at sheer forces between 1.1 and 7.4 Pa (thixotrope) was used in the experiment. As shown in FIG. 10, the efficiency is optimum in a negative pressure range between 150 mbar and 300 mbar. As also shown in FIG. 10, the efficiency decreases at a negative pressure below approximately 150 mbar and at a negative pressure of above 300 mbar.

Furthermore, the same liposomal amikacin formulation as in FIG. 8 was used in four different aerosol generators based on the modified eFlow®, wherein the first aerosol generator (A) is a modified eFlow® with an increased volume $V_{RN}$ of the liquid reservoir of 19.5 mL and filled with 8 mL of the liposomal amikacin formulation.

The second aerosol generator (B) had a reservoir with an increased volume $V_{RN}$ of 16 mL filled with 8 mL of the mentioned liposomal amikacin formulation, the third aerosol generator (C) one had an increased volume $V_{RN}$ of 24.5 mL, filled with 8 mL of the mentioned liquid. The fourth aerosol generator had an increased volume $V_{RN}$ of the liquid reservoir of 22.5 mL, and was filled with 8 mL of the aforementioned liposomal amikacin formulation.

Figure 11:
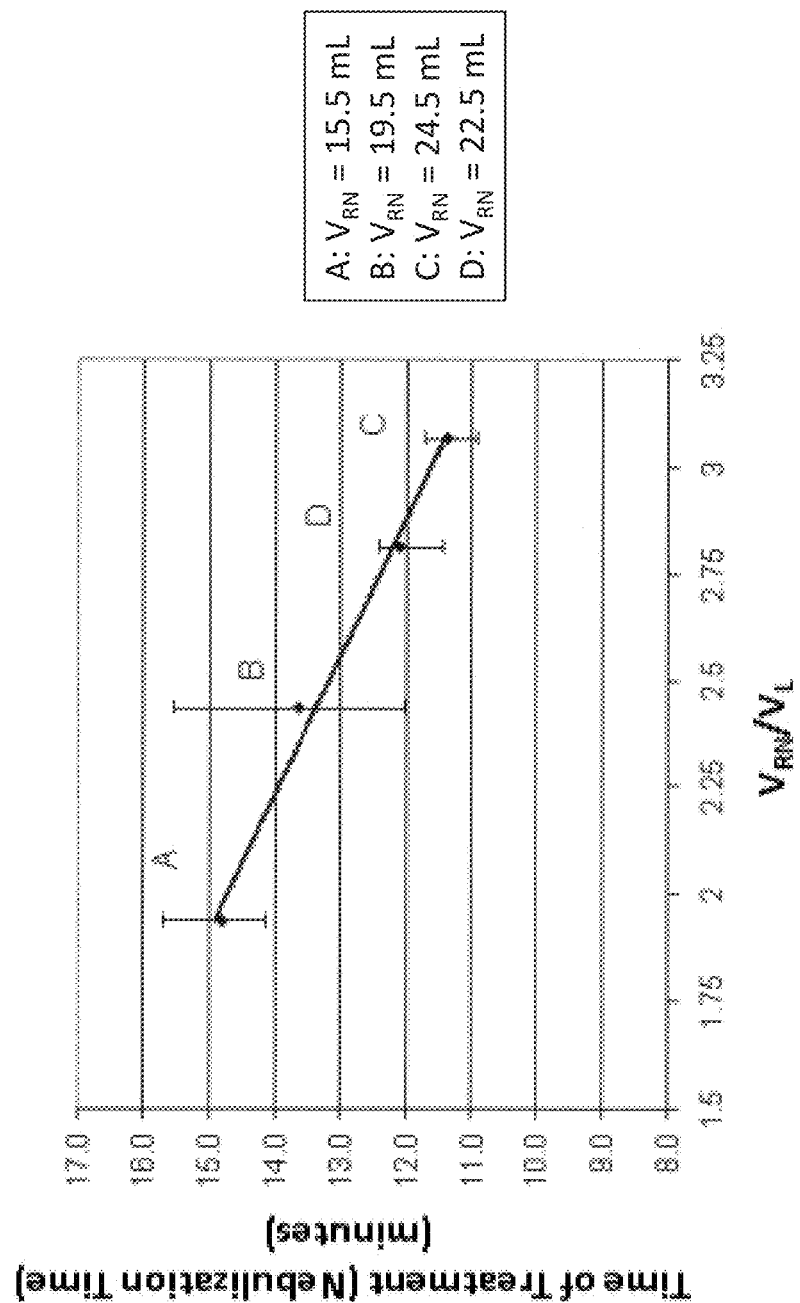
FIG. 11 is a graph of the period of time for aerosol generation upon complete emission of the liquid (nebulization time) as a function of the ratio between the increased volume $V_{RN}$ of the liquid reservoir and the initial volume of liquid within the liquid reservoir ($V_L$) ($V_{RN}/V_L$).

FIG. 11 shows experimental data of these four aerosol generators filled with 8 mL of the liposomal amikacin formulation. The results show the aerosol generation time for complete emission of the liposomal amikacin formulation within the liquid reservoir in relation to the ratio of the increased volume of the liquid reservoir ($V_{RN}$) to the initial volume of liquid in the liquid reservoir before use ($V_L$). FIG. 11 indicates that with the modified aerosol generator device (A) an aerosol generation time of approximately 16 minutes was required, whereas the aerosol generation time decreased with an increased ratio $V_{RN}/V_L$. The data also shows that the aerosol generation time could be reduced by approximately 4 minutes to below 12 minutes with the third aerosol generator device (C).

The data provided in Example 1 therefore indicates that a larger air cushion enables the operation of the aerosol generator for a longer time in an efficient negative pressure range so that the total aerosol generation time may significantly be reduced. Therefore, even large amounts of liquid such as 8 mL may be nebulized (emitted in form of aerosol) in a period of time below 12 minutes.

Example 2

Aerosol Properties of Amikacin Formulation

Eleven different lots of the liposomal amikacin formulation were examined with the modified eFlow® nebulizer (i.e., modified for use with the liposomal aminoglycoside formulations described herein) having a modified 40 mesh membrane fabricated as described herein, and a reservoir with an 8 mL liquid capacity and aforementioned air cushion. Cascade impaction was performed using either the ACI (Anderson Cascade Impactor) or the NGI (Next Generation Impactor) to establish aerosol properties: mass median aerodynamic diameter (MMAD), geometric standard deviation (GSD), and Fine-Particle-Fraction (FPF).

Mass Median Aerodynamic Diameter (MMAD) Measurement with ACI

An Anderson Cascade Impactor (ACI) was used for MMAD measurements and the nebulization work was conducted inside a ClimateZone chamber (Westech Instruments Inc., GA) to maintain temperature and relative humanity % during nebulization. The ClimateZone was pre-set to a temperature of 18° C. and a relative humanity of 50%. The ACI was assembled and loaded inside the ClimateZone. A probe thermometer (VWR dual thermometer) was attached to the surface of ACI at stage 3 to monitor the temperature of ACI. Nebulization was started when the temperature of the ACI reached 18±0.5° C.

With the 8 mL handsets loaded with 8 mL, it was found that the ACI could not handle the whole 8 mL dose; i.e., amikacin liposomal formulation deposited on ACI plate 3 overflowed. It was determined that the percent drug distribution on each ACI stage was not affected by the amount of liposomal amikacin formulation collected inside the ACI as long as there was no liquid overflow at ACI stage 3 (data not shown). Therefore for nebulization, the nebulizer was either filled with 4 mL liposomal amikacin formulation and nebulized until empty or filled with 8 mL of liposomal amikacin formulation and nebulized for about 6 minutes of collection time (i.e., ~4 mL).

The nebulizate was collected at a flow rate of 28.3 L/min in the ACI which was cooled to 18° C. The nebulization time was recorded and the nebulization rate calculated based on the difference in weight (amount nebulized) divided by the time interval.

After the nebulizate was collected, ACI collection plates 0, 1, 2, 3, 4, 5, 6 and 7 were removed, and each was loaded into its own petri dish. An appropriate amount of extraction solution (20 mL for plates 2, 3, and 4, and 10 mL for plates 0, 1, 5, 6, and 7) was added to each Petri dish to dissolve the formulation deposited on each plate. Samples from plates 0, 1, 2, 3, 4, 5 and 6 were further diluted appropriately with mobile phase C for HPLC analysis. Sample from plate 7 was directly analyzed by HPLC without any further dilution. The ACI Filter was also transferred to a 20 mL vial and 10 mL extraction solution was added, and the capped vial vortexed to dissolve any formulation deposited on it. Liquid samples from the vial were filtered (0.2 µm) into HPLC vials for HPLC analysis. The induction port with connector was also rinsed with 10 mL extraction solution to dissolve the formulation deposited on it, and the sample was collected and analyzed by HPLC with 2 time dilution. Based on the amikacin amount deposited on each stage of the impactor, mass median aerodynamic diameter (MMAD), geometric standard deviation (GSD) and fine particle fraction (FPF) were calculated.

In the cases for nebulizers loaded with 8 mL and nebulized for 6 minutes fine particle dose (FPD) was normalized to the volume of formulation nebulized in order to compare FPD across all experiments. FPD (normalized to the volume of formulation nebulized) was calculated according to the following equation:

$$FPD \text{ (normalized to volume nebulized)} \left(\frac{mg}{mL}\right) = \frac{\text{Amikacin Recovered}_{ACI} \times FPF \text{ (mg)}}{\text{Arikace Nebulized (g)} \div \text{Density} \left(\frac{g}{mL}\right)}$$

Mass Median Aerodynamic Diameter (MMAD) Measurement with NGI

A Next Generation Impactor (NGI) was also used for MMAD measurements and the nebulization work was conducted inside a ClimateZone chamber (Westech Instruments Inc., GA) to maintain temperature and RH % during nebulization. The ClimateZone was pre-set to a temperature of 18° C. and a relative humanity of 50%. The NGI was assembled and loaded inside the ClimateZone. A probe thermometer (VWR dual thermometer) was attached to the surface of NGI to monitor the temperature of NGI. Nebulization was started when the temperature of the NGI reached 18±0.5° C.

8 mL of the liposomal amikacin formulation was added to the nebulizer and nebulized. When there was no more aerosol observed, the timer was stopped. The nebulizate was collected at a flow rate of 15 L/min in the NGI which was cooled to 18° C. The nebulization time was recorded and the nebulization rate calculated based on the difference in weight (amount nebulized) divided by the time interval.

After aerosol collection was done, the NGI tray with tray holder was removed from NGI. An appropriate amount of extraction solution was added to NGI cups 1, 2, 3, 4, 5, 6, 7 and MOC to dissolve the formulation deposited on these cups. This material was transferred to a volumetric flask respectively. For NGI cups 1, 2, and 6, 25 ml volumetric flasks were used; for NIG cups 2, 3, 4, 50 ml volumetric flasks were used. More extraction solution was added to the cups and again transferred to the volumetric flask. This procedure was repeated several times in order to transfer formulation deposited on the NGI cup to the volumetric flask completely. The volumetric flasks were topped up to bring the final volume to either 25 ml or 50 ml and shaken well before sampled. Samples from cups 1, 2, 3, 4, 5, 6 and 7 were further diluted appropriately with mobile phase C for HPLC analysis. Sample from MOC was directly analyzed by HPLC without any further dilution. The NGI Filter was also transferred to a 20 mL vial and 10 mL extraction solution was added, and the capped vial vortexed to dissolve any formulation deposited on it. Liquid samples from the vial were filtered (0.2 micron) into HPLC vials for HPLC analysis. The Induction port with connector was also rinsed with 10 mL extraction solution to dissolve the formulation deposited on it, and the sample was collected and analyzed by HPLC with 11 time dilution.

Based on the amikacin amount deposited on each stage of the impactor, MMAD, GSD and FPF were calculated.

FPD was normalized to the volume of formulation nebulized in order to compare FPD across all experiments. FPD (normalized to the volume of formulation nebulized) was calculated according to the following equation:

$$\text{FPD (normalized to volume nebulized)}\left(\frac{mg}{mL}\right) = \frac{\text{Amikacin Recovered}_{ACI} \times FPF \text{ (mg)}}{\text{Arikace Nebulized (g)} \div \text{Density}\left(\frac{g}{mL}\right)}$$

Figure 12:
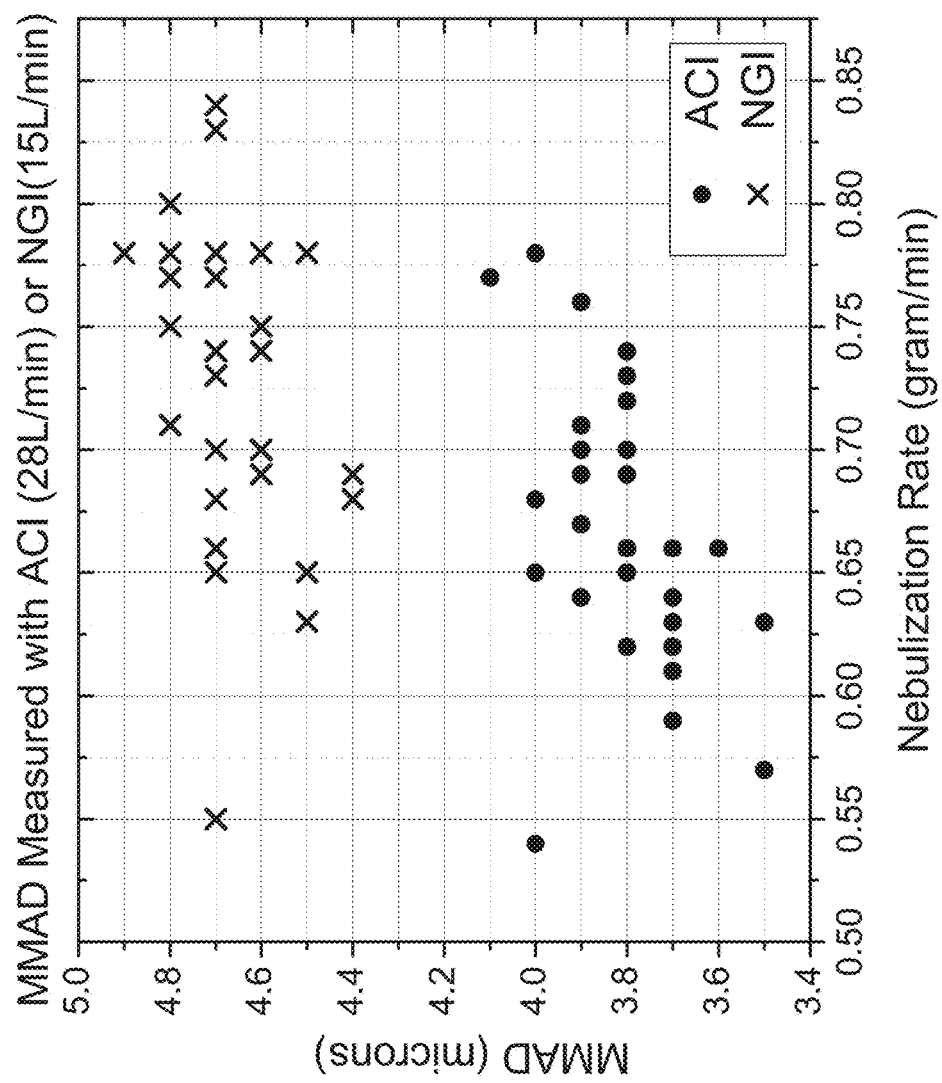
FIG. 12 is a graph showing the MMAD of aerosolized formulations as a function of nebulization rate of the respective formulation.
Figure 13:
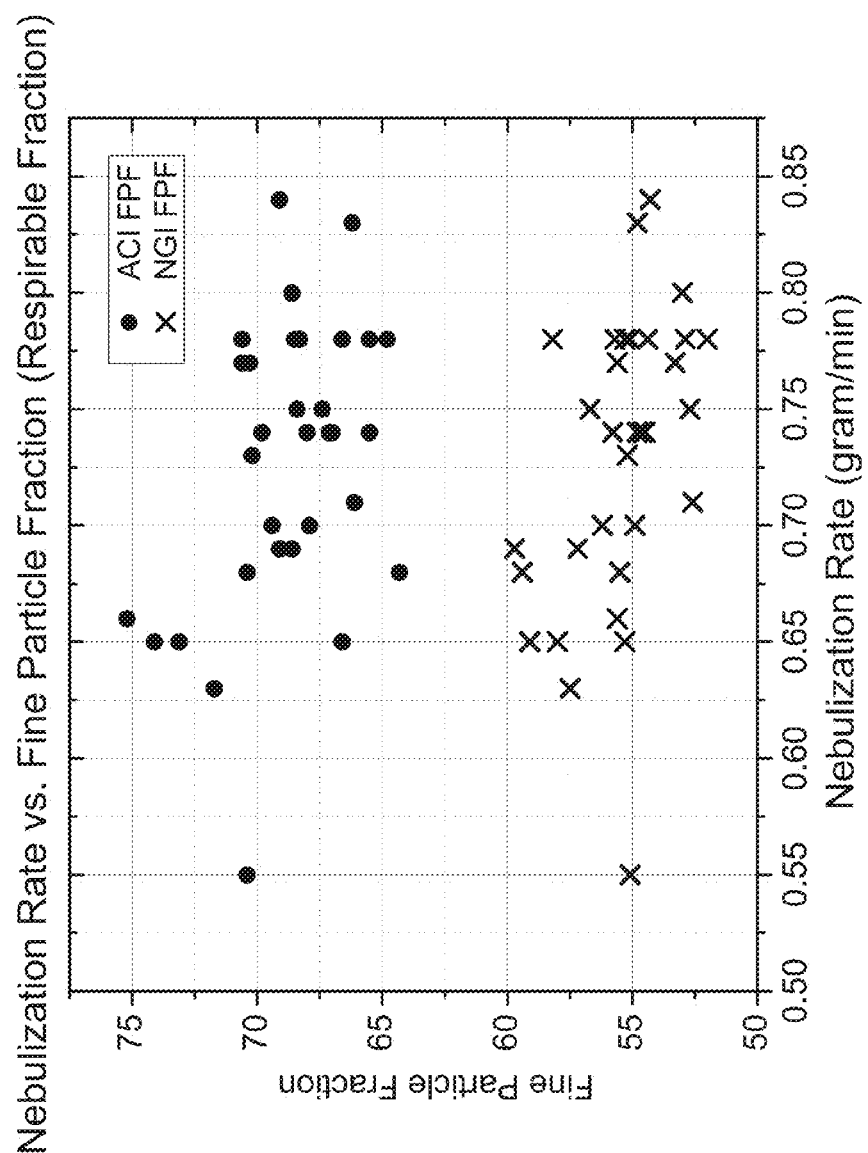
FIG. 13 is a graph showing the FPF of aerosolized formulations as a function of the nebulization rate of the respective formulation.

The results of these experiments are provided in FIGS. 12 and 13 and Table 5, below.

TABLE 5

Aerosol Characteristics

| Amikacin Conc. | Run | ACI APSD Data | | | | | NGI APSD Data | | | | | Nebulization Data | | |
|---|---|---|---|---|---|---|---|---|---|---|---|---|---|---|
| | | Aerosol Head ID | Neb. Rate (g/min) | MMAD (μm) | GSD | FPF <5 μm (%) | Aerosol Head ID | Neb. Rate (g/min) | MMAD (μm) | GSD | FPF <5 μm (%) | Aerosol Head ID | Neb. Rate (g/min) | % Assoc. Amikacin Post-Neb |
| 66.9 mg/mL | 1 | J | 0.66 | 3.7 | 1.7 | 70.4 | J | 0.68 | 4.7 | 1.7 | 55.5 | A | 0.63 | 69.1 |
| | 2 | K | 0.62 | 3.7 | 1.7 | 71.7 | K | 0.63 | 4.5 | 1.7 | 57.5 | B | 0.60 | 68.2 |
| | 3 | L | 0.65 | 4.0 | 1.8 | 66.1 | L | 0.71 | 4.8 | 1.7 | 52.6 | C | 0.56 | 69.9 |
| 70.8 mg/mL | 1 | M | 0.64 | 3.9 | 1.7 | 67.1 | M | 0.74 | 4.7 | 1.7 | 54.8 | M | 0.65 | 64.5 |
| | 2 | N | 0.68 | 4.0 | 1.8 | 64.8 | N | 0.78 | 4.9 | 1.7 | 52.0 | N | 0.67 | 66.3 |
| | 3 | O | 0.69 | 3.9 | 1.7 | 67.4 | O | 0.75 | 4.8 | 1.7 | 52.7 | O | 0.64 | 69.4 |
| 64.6 mg/mL | 1 | C | 0.78 | 4.0 | 1.8 | 65.5 | A | 0.74 | 4.7 | 1.7 | 54.6 | G | 0.72 | 71.9 |
| | 2 | D | 0.64 | 3.7 | 1.7 | 70.2 | B | 0.73 | 4.7 | 1.7 | 55.2 | H | 0.64 | 71.5 |
| | 3 | H | 0.62 | 3.7 | 1.7 | 70.6 | C | 0.78 | 4.7 | 1.7 | 54.4 | J | 0.68 | 71.8 |
| 68.5 mg/mL | 1 | E | 0.69 | 3.8 | 1.7 | 69.4 | E | 0.70 | 4.6 | 1.7 | 56.2 | E | 0.60 | 69.1 |
| | 2 | F | 0.78 | 4.0 | 1.8 | 66.2 | F | 0.83 | 4.7 | 1.7 | 54.8 | F | 0.67 | 70.4 |
| | 3 | G | 0.65 | 3.8 | 1.7 | 69.1 | G | 0.69 | 4.6 | 1.7 | 57.2 | G | 0.61 | 69.5 |
| 65.7 mg/mL | 1 | V | 0.74 | 3.8 | 1.7 | 69.1 | V | 0.84 | 4.7 | 1.7 | 54.3 | M | 0.64 | 69.2 |
| | 2 | W | 0.72 | 3.8 | 1.7 | 68.3 | W | 0.78 | 4.7 | 1.7 | 55.1 | N | 0.74 | 67.9 |
| | 3 | X | 0.70 | 3.9 | 1.7 | 68.0 | X | 0.74 | 4.7 | 1.7 | 54.5 | O | 0.63 | 68.6 |
| 66.8 mg/mL | 1 | J | 0.63 | 3.7 | 1.8 | 70.6 | A | 0.77 | 4.8 | 1.7 | 53.3 | A | 0.70 | 73.2 |
| | 2 | K | 0.59 | 3.7 | 1.8 | 70.4 | D | 0.55 | 4.7 | 1.7 | 55.1 | B | 0.70 | 72.4 |
| | 3 | L | 0.64 | 3.9 | 1.8 | 66.6 | H | 0.65 | 4.7 | 1.7 | 55.3 | C | 0.83 | 72.8 |
| 69.2 mg/mL | 1 | S | 0.66 | 3.8 | 1.7 | 68.6 | U | 0.80 | 4.8 | 1.7 | 53.0 | S | 0.69 | 70.7 |
| | 2 | T | 0.73 | 3.8 | 1.7 | 68.3 | V | 0.78 | 4.5 | 1.7 | 58.2 | T | 0.75 | 71.0 |
| | 3 | U | 0.54 | 4.0 | 1.8 | 65.5 | W | 0.78 | 4.7 | 1.7 | 55.3 | U | 0.80 | 71.1 |
| 71.4 mg/mL | 1 | Q | 0.66 | 3.8 | 1.7 | 68.4 | M | 0.75 | 4.6 | 1.7 | 56.7 | P | 0.71 | 72.4 |
| | 2 | R | 0.71 | 3.9 | 1.8 | 66.6 | N | 0.78 | 4.8 | 1.7 | 52.9 | Q | 0.68 | 70.0 |
| | 3 | S | 0.66 | 3.8 | 1.7 | 68.5 | O | 0.78 | 4.6 | 1.7 | 55.7 | R | 0.74 | 71.7 |
| 69.9 mg/mL | 1 | C | 0.77 | 4.1 | 1.8 | 64.3 | J | 0.68 | 4.4 | 1.7 | 59.4 | A | 0.68 | 73.8 |
| | 2 | D | 0.62 | 3.8 | 1.7 | 68.6 | K | 0.69 | 4.4 | 1.7 | 59.7 | B | 0.63 | 73.6 |
| | 3 | H | 0.61 | 3.7 | 1.7 | 70.3 | L | 0.77 | 4.7 | 1.7 | 55.6 | C | 0.70 | 75.7 |
| 72.2 mg/mL | 1 | T | 0.70 | 3.8 | 1.7 | 69.8 | T | 0.74 | 4.6 | 1.7 | 55.8 | M | 0.65 | 67.9 |
| | 2 | U | 0.76 | 3.9 | 1.7 | 67.0 | U | 0.74 | 4.7 | 1.7 | 54.8 | N | 0.71 | 70.3 |
| | 3 | X | 0.67 | 3.9 | 1.7 | 67.9 | X | 0.70 | 4.7 | 1.7 | 54.9 | P | 0.57 | 71.8 |
| 70.4 mg/mL | 1 | C | 0.66 | 3.6 | 1.7 | 73.1 | J | 0.65 | 4.5 | 1.7 | 58.0 | H | 0.59 | 60.1 |
| | 2 | D | 0.57 | 3.5 | 1.7 | 74.1 | K | 0.65 | 4.5 | 1.7 | 59.1 | J | 0.69 | 59.3 |
| | 3 | E | 0.63 | 3.5 | 1.7 | 75.2 | L | 0.66 | 4.7 | 1.7 | 55.6 | K | 0.63 | 58.5 |

Example 3

Nebulization Rate Study

Nebulization rate studies (grams of formulation nebulized per minute) were conducted in a biosafety cabinet (Model 1168, Type B2, FORMA Scientific). The assembled nebulizer (handset with mouth piece and aerosol head) was first weighed empty ($W_1$), then a certain volume of formulation was added and the nebulizer device was weighed again ($W_2$). The nebulizer and timer were started and the formulations nebulized were collected in a chilled impinger at a flow rate of ~8 L/min (see FIG. 14 for details of experimental setup). When there was no more aerosol observed, the timer was stopped. The nebulizer was weighed again ($W_3$), and the time of nebulization (t) was recorded. Total formulation nebulized was calculated as $W_2-W_3$ and total drug residue after nebulization was calculated as $W_3-W_1$. The nebulization rate of formulation was calculated according to the following equation:

$$\text{Nebulization Rate}\left(\frac{g}{\min}\right) = \frac{W_2 - W_3}{t}$$

Nebulization rates in g/min., as well as other related results, for liposomal amikacin nebulized using a nebulizer fabricated according to the specification (twenty four aerosol heads were selected and were used in these studies) are captured in Table 6.

TABLE 6

Formulation nebulization rates (g/min)

| Run | Aerosol Head # | Neb Time (min) | Formulation Nebulized (g) | Neb Rate (g/min) |
|---|---|---|---|---|
| 1 | 1 | 11.90 | 7.7346 | 0.65 |
| 2 | 2 | 11.58 | 8.0573 | 0.70 |
| 3 | 3 | 10.87 | 8.0029 | 0.74 |
| 4 | 4 | 13.63 | 7.9359 | 0.58 |
| 5 | 5 | 12.60 | 8.0577 | 0.64 |
| 6 | 6 | 12.62 | 8.0471 | 0.64 |
| 7 | 7 | 14.23 | 8.073 | 0.57 |
| 8 | 8 | 14.67 | 8.0872 | 0.55 |
| 9 | 9 | 13.58 | 7.9235 | 0.58 |
| 10 | 10 | 12.28 | 7.9649 | 0.65 |
| 11 | 11 | 12.33 | 8.1872 | 0.66 |
| 12 | 12 | 13.17 | 8.1694 | 0.62 |
| 13 | 1 | 11.22 | 7.9991 | 0.71 |
| 14 | 2 | 11.90 | 8.1392 | 0.68 |
| 15 | 3 | 12.17 | 8.0162 | 0.66 |
| 16 | 4 | 12.90 | 8.0174 | 0.62 |
| 17 | 5 | 11.22 | 7.893 | 0.70 |
| 18 | 6 | 10.23 | 8.0401 | 0.79 |
| 19 | 7 | 12.55 | 8.0988 | 0.65 |
| 20 | 8 | 14.88 | 7.8781 | 0.53 |
| 21 | 9 | 13.68 | 8.1678 | 0.60 |
| 22 | 10 | 12.33 | 8.2253 | 0.67 |
| 23 | 11 | 12.60 | 8.0783 | 0.64 |
| 24 | 12 | 11.83 | 7.946 | 0.67 |
| 25 | 1 | 11.92 | 8.1703 | 0.69 |
| 26 | 2 | 11.95 | 7.9837 | 0.67 |
| 27 | 3 | 13.63 | 8.1536 | 0.60 |
| 28 | 4 | 11.90 | 7.9376 | 0.67 |
| 29 | 5 | 12.27 | 8.1727 | 0.67 |
| 30 | 6 | 12.27 | 8.0875 | 0.66 |
| 31 | 7 | 13.65 | 8.0767 | 0.59 |
| 32 | 8 | 15.80 | 8.1183 | 0.51 |
| 33 | 9 | 13.65 | 8.1373 | 0.60 |
| 34 | 10 | 12.98 | 7.8864 | 0.61 |
| 35 | 11 | 11.63 | 8.1445 | 0.70 |
| 36 | 12 | 12.95 | 8.0232 | 0.62 |
| 37 | 13 | 12.80 | 7.9098 | 0.62 |
| 38 | 14 | 10.25 | 8.0328 | 0.78 |
| 39 | 15 | 12.13 | 7.9911 | 0.66 |
| 40 | 16 | 12.33 | 8.1756 | 0.66 |
| 41 | 17 | 12.47 | 7.9417 | 0.64 |
| 42 | 18 | 13.17 | 7.9046 | 0.60 |
| 43 | 19 | 13.92 | 7.5367 | 0.54 |
| 44 | 20 | 11.47 | 8.1466 | 0.71 |
| 45 | 21 | 11.67 | 7.9366 | 0.68 |
| 46 | 22 | 13.17 | 8.0613 | 0.61 |
| 47 | 23 | 12.77 | 7.8596 | 0.62 |
| 48 | 24 | 12.25 | 8.0552 | 0.66 |
| 49 | 13 | 13.67 | 7.9379 | 0.58 |
| 50 | 14 | 10.55 | 8.0221 | 0.76 |
| 51 | 15 | 11.80 | 8.0555 | 0.68 |
| 52 | 16 | 10.08 | 8.1639 | 0.81 |
| 53 | 17 | 11.08 | 7.9121 | 0.71 |
| 54 | 18 | 12.28 | 8.017 | 0.65 |
| 55 | 19 | 11.40 | 7.9415 | 0.70 |

TABLE 6-continued

Formulation nebulization rates (g/min)

| Run | Aerosol Head # | Neb Time (min) | Formulation Nebulized (g) | Neb Rate (g/min) |
|---|---|---|---|---|
| 56 | 20 | 12.17 | 8.211 | 0.67 |
| 57 | 21 | 11.45 | 8.18 | 0.71 |
| 58 | 22 | 12.03 | 7.8946 | 0.66 |
| 59 | 23 | 12.83 | 8.0771 | 0.63 |
| 60 | 24 | 11.97 | 7.9936 | 0.67 |
| 61 | 13 | 12.38 | 8.0054 | 0.65 |
| 62 | 14 | 10.53 | 8.0492 | 0.76 |
| 63 | 15 | 11.82 | 7.8161 | 0.66 |
| 64 | 16 | 11.83 | 8.1169 | 0.69 |
| 65 | 17 | 12.67 | 8.1778 | 0.65 |
| 66 | 18 | 12.03 | 8.2436 | 0.69 |
| 67 | 19 | 13.17 | 7.8821 | 0.60 |
| 68 | 20 | 12.17 | 8.2397 | 0.68 |
| 69 | 21 | 11.78 | 8.1814 | 0.69 |
| 70 | 22 | 11.78 | 8.3443 | 0.71 |
| 71 | 23 | 13.17 | 8.1699 | 0.62 |
| 72 | 24 | 11.50 | 8.0413 | 0.70 |
| Average | | 12.4 ± 1.1 | 8.0 ± 0.1 | 0.66 ± 0.06 |

Example 4

Percent of Associate Amikacin Post-Nebulization and Nebulizate Characterization

Figure 14:
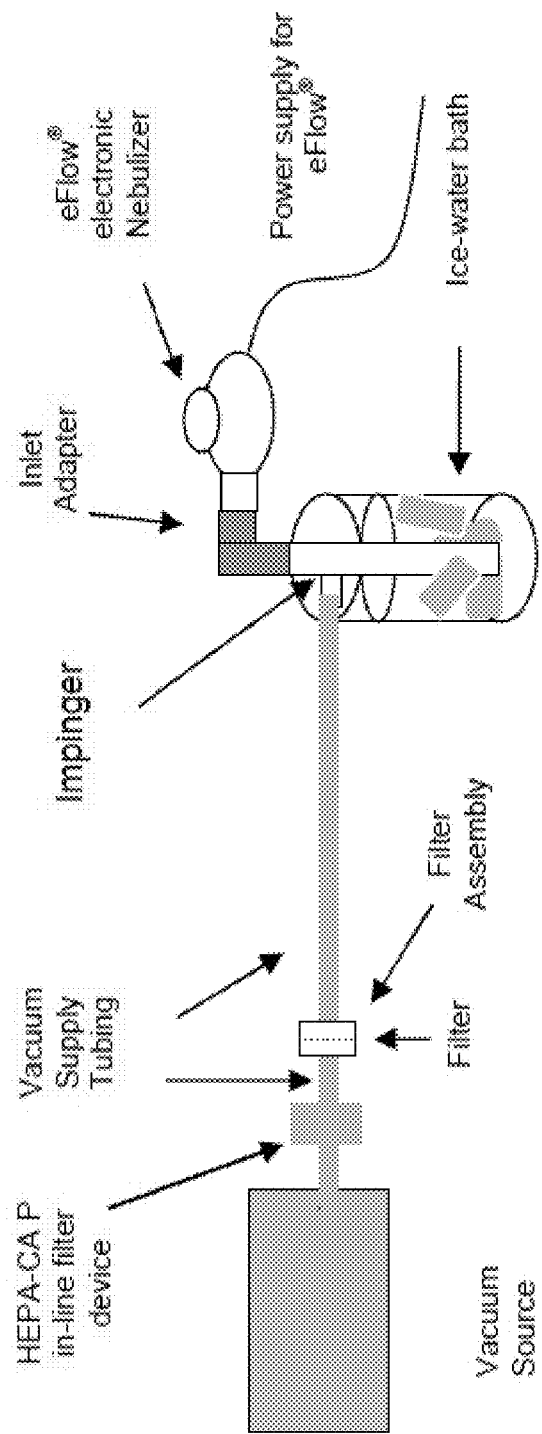
FIG. 14 is a schematic of the system used for the recovery of aerosol for post-nebulization studies.

The free and liposomal complexed amikacin in the nebulizate of Example 3 was measured. As mentioned in Example 3, the nebulizate was collected in a chilled impinger at a flow rate of 8 L/min (FIG. 14).

The nebulizate collected in the impinger was rinsed with 1.5% NaCl and transferred to a 100 mL or 50-mL volumetric flask. The impinger was then rinsed several times with 1.5% NaCl in order to transfer all the formulation deposited in the impinger to the flask. To measure the free amikacin concentration of the nebulizate, 0.5 mL of the diluted nebulizate inside the volumetric flask was taken and loaded to an Amicon® Ultra—0.5 mL 30K centrifugal filter device (regenerated cellulose, 30K MWCO, Millipore) and this device was centrifuged at 5000 G at 15° C. for 15 minutes. An appropriate amount of filtrate was taken and was diluted 51 times with mobile phase C solution. Amikacin concentration was determined by HPLC. To measure total amikacin concentration of the nebulizate, an appropriate amount of the diluted nebulizate inside the volumetric flask was taken and diluted (also dissolved) 101 times in extraction solution (perfluoropentanoic acid: 1-propanol:water (25:225:250, v/v/v)) and the amikacin concentration determined by HPLC.

The percent associated amikacin post-nebulization was calculated by the following equation:

$$\% \text{ Associated} = \frac{\text{Concentration}_{Total} - \text{Concentration}_{Free}}{\text{Concentration}_{Total}} \times 100$$

The percent associated amikacin post-nebulization and total dose recovery from nebulization experiments described in Table 6 are summarized in Table 7. Corresponding nebulization rates were also included in Table 7.

TABLE 7

Percent associated amikacin post-nebulization and total dose recovered

| Run | Aerosol Head # | % Associated | Recovered % | Neb Rate (g/min) |
|---|---|---|---|---|
| 1 | 1 | 65.7 | 104 | 0.65 |
| 2 | 2 | 65.1 | 97 | 0.70 |
| 3 | 3 | 64.5 | 96 | 0.74 |
| 4 | 4 | 66.1 | 97 | 0.58 |
| 5 | 5 | 62.1 | 92 | 0.64 |
| 6 | 6 | 65.5 | 95 | 0.64 |
| 7 | 7 | 63.5 | 94 | 0.57 |
| 8 | 8 | 60.4 | 92 | 0.55 |
| 9 | 9 | 65.0 | 93 | 0.58 |
| 10 | 10 | 72.7 | 102 | 0.65 |
| 11 | 11 | 64.9 | 92 | 0.66 |
| 12 | 12 | 66.7 | 97 | 0.62 |
| 13 | 1 | 67.1 | 102 | 0.71 |
| 14 | 2 | 64.2 | 97 | 0.68 |
| 15 | 3 | 68.8 | 98 | 0.66 |
| 16 | 4 | 65.5 | 94 | 0.62 |
| 17 | 5 | 66.1 | 98 | 0.70 |
| 18 | 6 | 65.7 | 94 | 0.79 |
| 19 | 7 | 65.5 | 100 | 0.65 |
| 20 | 8 | 64.8 | 95 | 0.53 |
| 21 | 9 | 60.3 | 94 | 0.60 |
| 22 | 10 | 59.1 | 95 | 0.67 |
| 23 | 11 | 63.3 | 95 | 0.64 |
| 24 | 12 | 66.3 | 98 | 0.67 |
| 25 | 1 | 66.4 | 104 | 0.69 |
| 26 | 2 | 63.5 | 93 | 0.67 |
| 27 | 3 | 62.9 | 93 | 0.60 |
| 28 | 4 | 64.2 | 93 | 0.67 |
| 29 | 5 | 64.9 | 99 | 0.67 |
| 30 | 6 | 68.2 | 98 | 0.66 |
| 31 | 7 | 61.0 | 96 | 0.59 |
| 32 | 8 | 59.9 | 96 | 0.51 |
| 33 | 9 | 63.0 | 95 | 0.60 |
| 34 | 10 | 58.1 | 95 | 0.61 |
| 35 | 11 | 66.1 | 98 | 0.70 |
| 36 | 12 | 64.2 | 98 | 0.62 |
| 37 | 13 | 65.6 | 100 | 0.62 |
| 38 | 14 | 68.9 | 96 | 0.78 |
| 39 | 15 | 63.7 | 97 | 0.66 |
| 40 | 16 | 64.7 | 97 | 0.66 |
| 41 | 17 | 69.1 | 97 | 0.64 |
| 42 | 18 | 70.2 | 94 | 0.60 |
| 43 | 19 | 61.2 | 93 | 0.54 |
| 44 | 20 | 63.4 | 91 | 0.71 |
| 45 | 21 | 67.7 | 99 | 0.68 |
| 46 | 22 | 66.7 | 96 | 0.61 |
| 47 | 23 | 67.2 | 93 | 0.62 |
| 48 | 24 | 69.6 | 98 | 0.66 |
| 49 | 13 | 66.2 | 102 | 0.58 |
| 50 | 14 | 66.9 | 97 | 0.76 |
| 51 | 15 | 66.7 | 96 | 0.68 |
| 52 | 16 | 64.7 | 96 | 0.81 |
| 53 | 17 | 65.1 | 96 | 0.71 |
| 54 | 18 | 67.6 | 98 | 0.65 |
| 55 | 19 | 66.7 | 97 | 0.70 |
| 56 | 20 | 63.6 | 99 | 0.67 |
| 57 | 21 | 68.1 | 101 | 0.71 |
| 58 | 22 | 64.8 | 99 | 0.66 |
| 59 | 23 | 66.2 | 97 | 0.63 |
| 60 | 24 | 67.4 | 103 | 0.67 |
| 61 | 13 | 64.2 | 99 | 0.65 |
| 62 | 14 | 68.7 | 101 | 0.76 |
| 63 | 15 | 66.0 | 100 | 0.66 |
| 64 | 16 | 67.7 | 103 | 0.69 |
| 65 | 17 | 66.4 | 100 | 0.65 |
| 66 | 18 | 66.2 | 98 | 0.69 |
| 67 | 19 | 68.3 | 100 | 0.60 |
| 68 | 20 | 67.9 | 101 | 0.68 |
| 69 | 21 | 67.1 | 98 | 0.69 |
| 70 | 22 | 66.2 | 101 | 0.71 |
| 71 | 23 | 67.0 | 97 | 0.62 |
| 72 | 24 | 68.0 | 100 | 0.70 |
| Average | | 65.5 ± 2.6 | 97 ± 3 | 0.66 ± 0.06 |

The total concentration of amikacin in the liposomal amikacin formulation was measured during this study with the rest of the samples using the same HPLC and amikacin standards. The value obtained was 64 mg/mL amikacin. The % associated amikacin post-nebulization values ranged from 58.1% to 72.7%, with an average value of 65.5±2.6%; for 8 mL liposomal amikacin formulation nebulized, the total recovered amount of amikacin ranged from 426 mg to 519 mg, with an average value of 476±17 mg; the calculated amount of amikacin nebulized (according to the weight of the liposomal amikacin formulation nebulized in Table 7) ranged from 471 mg to 501 mg, with an average value of 490±8 mg; the total amikacin recovery ranged from 91% to 104%, with an average value of 97±3% (n=72).

Liposome Size

The liposomal amikacin formulation (64 mg/mL amikacin), either pre-nebulized or post-nebulized, was diluted appropriately with 1.5% NaCl and the liposome particle size was measured by light scattering using a Nicomp 380 Submicron Particle Sizer (Nicomp, Santa Barbara, Calif.).

The liposome sizes post-nebulization of the liposomal amikacin formulation aerosolized with twenty four nebulizer aerosol heads with 8 mL reservoir handsets were measured. The liposome size ranged from 248.9 nm to 288.6 nm, with an average of 264.8±6.7 nm (n=72). These results are provided in Table 8. The pre-nebulization liposome mean diameter was approximately 285 nm (284.5 nm±6.3 nm).

TABLE 8

Liposome size post-nebulization

| Run | Aerosol Head # | Mean Diameter (nm) |
|---|---|---|
| 1 | 1 | 270.9 |
| 2 | 2 | 274.6 |
| 3 | 3 | 253.9 |
| 4 | 4 | 256.3 |
| 5 | 5 | 274.0 |
| 6 | 6 | 273.6 |
| 7 | 7 | 260.0 |
| 8 | 8 | 268.1 |
| 9 | 9 | 264.7 |
| 10 | 10 | 254.8 |
| 11 | 11 | 266.9 |
| 12 | 12 | 270.0 |
| 13 | 1 | 269.6 |
| 14 | 2 | 271.2 |
| 15 | 3 | 254.6 |
| 16 | 4 | 270.7 |
| 17 | 5 | 260.8 |
| 18 | 6 | 252.3 |
| 19 | 7 | 267.8 |
| 20 | 8 | 265.0 |
| 21 | 9 | 261.5 |
| 22 | 10 | 258.0 |
| 23 | 11 | 248.9 |
| 24 | 12 | 262.4 |
| 25 | 1 | 266.0 |
| 26 | 2 | 270.4 |
| 27 | 3 | 268.6 |
| 28 | 4 | 266.6 |
| 29 | 5 | 259.4 |
| 30 | 6 | 265.2 |
| 31 | 7 | 262.4 |
| 32 | 8 | 257.7 |
| 33 | 9 | 264.1 |
| 34 | 10 | 258.5 |
| 35 | 11 | 273.4 |
| 36 | 12 | 260.2 |
| 37 | 13 | 266.0 |
| 38 | 14 | 270.2 |
| 39 | 15 | 268.2 |

TABLE 8-continued

Liposome size post-nebulization

| Run | Aerosol Head # | Mean Diameter (nm) |
|---|---|---|
| 40 | 16 | 266.2 |
| 41 | 17 | 265.5 |
| 42 | 18 | 268.5 |
| 43 | 19 | 263.3 |
| 44 | 20 | 257.8 |
| 45 | 21 | 271.3 |
| 46 | 22 | 266.2 |
| 47 | 23 | 270.6 |
| 48 | 24 | 269.7 |
| 49 | 13 | 269.1 |
| 50 | 14 | 265.7 |
| 51 | 15 | 258.7 |
| 52 | 16 | 268.0 |
| 53 | 17 | 266.2 |
| 54 | 18 | 254.0 |
| 55 | 19 | 263.9 |
| 56 | 20 | 265.3 |
| 57 | 21 | 264.5 |
| 58 | 22 | 266.5 |
| 59 | 23 | 264.8 |
| 60 | 24 | 271.7 |
| 61 | 13 | 259.8 |
| 62 | 14 | 268.8 |
| 63 | 15 | 265.9 |
| 64 | 16 | 274.7 |
| 65 | 17 | 256.2 |
| 66 | 18 | 269.7 |
| 67 | 19 | 257.7 |
| 68 | 20 | 255.7 |
| 69 | 21 | 264.8 |
| 70 | 22 | 288.6 |
| 71 | 23 | 252.1 |
| 72 | 24 | 263.4 |
| Average |  | 264.8 ± 6.7 |

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A system for treating or providing prophylaxis against a pulmonary infection in a patient, comprising:
(a) a pharmaceutical formulation comprising an aqueous dispersion of liposomal complexed aminoglycoside, wherein the lipid component of the liposomal complexed aminoglycoside is present at 45-60 mg/mL and consists of dipalmitoylphosphatidylcholine (DPPC) and cholesterol, and
(b) a nebulizer comprising a vibrating mesh membrane, which generates an aerosol of the pharmaceutical formulation at a rate of 0.60 g per minute to 0.80 g per minute, wherein the fine particle fraction (FPF) of the aerosol is greater than or equal to about 64%, as measured by the Andersen Cascade Impactor (ACI), or greater than or equal to about 51%, as measured by the Next Generation Impactor (NGI) and the percent associated aminoglycoside of the aerosol is from 60% to 70%.

2. The system of claim 1, wherein the aminoglycoside is selected from amikacin, apramycin, arbekacin, astromicin, capreomycin, dibekacin, framycetin, gentamicin, hygromycin B, isepamicin, kanamycin, neomycin, netilmicin, paromomycin, rhodestreptomycin, ribostamycin, sisomicin, spectinomycin, streptomycin, tobramycin, verdamicin, or a combination thereof.

3. The system of claim 1, wherein the aminoglycoside is amikacin.

4. The system of claim 3, wherein the amikacin is amikacin sulfate.

5. The system of claim 1, wherein the liposomes of the liposomal aminoglycoside formulation are unilamellar vesicles, multilamellar vesicles, or a mixture thereof.

6. The system of claim 1, wherein the aminoglycoside is amikacin, and the liposomes of the liposomal aminoglycoside formulation are unilamellar vesicles, multilamellar vesicles, or a mixture thereof.

7. The system of claim 1, wherein the fine particle fraction (FPF) of the aerosolized pharmaceutical formulation is about 64% to about 80%, as measured by the ACI; or about 51% to about 65%, as measured by the NGI.

8. A method for treating or providing prophylaxis against a pulmonary infection in a patient, the method comprising:
aerosolizing with a nebulizer comprising a vibrating mesh membrane at a rate of 0.60 g per minute to 0.80 g per minute, a pharmaceutical formulation comprising an aqueous dispersion of liposomal complexed aminoglycoside, wherein the lipid component of the liposomal complexed aminoglycoside is present at 45-60 mg/mL and consists of dipalmitoylphosphatidylcholine (DPPC) and cholesterol, to form an aerosolized pharmaceutical formulation, and
administering the aerosolized pharmaceutical formulation to the lungs of the patient; wherein the aerosolized pharmaceutical formulation comprises a mixture of free aminoglycoside and liposomal complexed aminoglycoside, the fine particle fraction (FPF) of the aerosolized pharmaceutical formulation is greater than or equal to about 64%, as measured by the Andersen Cascade Impactor (ACI), or greater than or equal to about 51%, as measured by the Next Generation Impactor (NGI) and the percent liposomal complexed aminoglycoside of the aerosolized pharmaceutical formulation is from 60% to 70%.

9. The method of claim 8, wherein the aminoglycoside is selected from amikacin, apramycin, arbekacin, astromicin, capreomycin, dibekacin, framycetin, gentamicin, hygromycin B, isepamicin, kanamycin, neomycin, netilmicin, paromomycin, ribostamycin, sisomicin, rhodestreptomycin, spectinomycin, streptomycin, tobramycin, verdamicin, or a combination thereof.

10. The method of claim 8, wherein the aerosolized pharmaceutical formulation is administered once per day in a single dosing session.

11. The method of claim 8, wherein the aminoglycoside is amikacin.

12. The method of claim 11, wherein the amikacin is amikacin sulfate.

13. The method of claim 8, wherein the patient has cystic fibrosis.

14. The method of claim 8, wherein the pulmonary infection is a nontuberculous mycobacterial infection.

15. The method of claim 8, wherein the fine particle fraction (FPF) of the aerosolized pharmaceutical formulation is about 64% to about 80%, as measured by the ACI; or about 51% to about 65%, as measured by the NGI.

16. The method of claim 14, wherein the nontuberculous mycobacterial infection is *M. avium, M. avium* subsp. *hominissuis* (MAH), *M. abscessus, M. chelonae, M. bolletii, M. kansasii, M. ulcerans, M. avium, M. avium complex* (MAC), *M. conspicuum, M. kansasii, M. peregrinum, M. immunogenum, M. xenopi, M. marinum, M. malmoense, M. marinum, M. mucogenicum, M. nonchromogenicum, M. scrofulaceum, M. simiae, M. smegmatis, M. szulgai, M. terrae, M. terrae* complex, *M. haemophilum, M. genavense, M. asiaticum, M. shimoidei, M. gordonae, M. nonchromogenicum, M. triplex, M. lentiflavum, M. celatum, M. fortuitum* or *M. fortuitum* complex.

17. The method of claim 16, wherein the nontuberculous mycobacterial infection is *M. avium* complex (MAC).

18. The method of claim 17, wherein the aminoglycoside is amikacin.

19. The method of claim 18, wherein the amikacin is amikacin sulfate.

20. The method of claim 8, wherein the pulmonary infection is a nontuberculous mycobacterial infection and the aminoglycoside is amikacin sulfate.

21. The method of claim 8, wherein the pulmonary infection is a *M. avium* complex (MAC) infection, and the aminoglycoside is amikacin sulfate.

22. The system of claim 1, wherein the mass median aerodynamic diameter (MMAD) of the aerosol is < about 4.2 as measured by the ACI, or < about 4.9 as measured by the NGI.

23. The system of claim 22, wherein the MMAD of the aerosol is about 3.2 µm to about 4.2 as measured by the ACI; or about 4.4 µm to about 4.9 as measured by the NGI.

24. The method of claim 8, wherein the mass median aerodynamic diameter (MMAD) of the aerosol is < about 4.2 as measured by the ACI, or < about 4.9 as measured by the NGI.

25. The method of claim 24, wherein the MMAD of the aerosol is about 3.2 µm to about 4.2 as measured by the ACI; or about 4.4 µm to about 4.9 as measured by the NGI.

* * * * *

UNITED STATES PATENT AND TRADEMARK OFFICE
CERTIFICATE OF CORRECTION

| | | |
|---|---|---|
| PATENT NO. | : 9,566,234 B2 | Page 1 of 1 |
| APPLICATION NO. | : 13/899457 | |
| DATED | : February 14, 2017 | |
| INVENTOR(S) | : Walter R. Perkins et al. | |

It is certified that error appears in the above-identified patent and that said Letters Patent is hereby corrected as shown below:

In the Claims

Column 42, Claim 22, Line 8, please insert -- μm -- after 4.2.

Column 42, Claim 22, Line 9, please insert -- μm -- after 4.9.

Column 42, Claim 23, Line 12, please insert -- μm -- after 4.2.

Column 42, Claim 23, Line 13, please insert -- μm -- after 4.9.

Column 42, Claim 24, Line 15, please insert -- μm -- after 4.2.

Column 42, Claim 24, Line 16, please insert -- μm -- after 4.9.

Column 42, Claim 25, Line 19, please insert -- μm -- after 4.2.

Column 42, Claim 25, Line 20, please insert -- μm -- after 4.9.

Signed and Sealed this
First Day of November, 2022

Katherine Kelly Vidal
*Director of the United States Patent and Trademark Office*